US009249408B2

(12) United States Patent
Liu et al.

(10) Patent No.: US 9,249,408 B2
(45) Date of Patent: Feb. 2, 2016

(54) DIRECTED EVOLUTION USING PROTEINS COMPRISING UNNATURAL AMINO ACIDS

(75) Inventors: Chang Liu, San Diego, CA (US);
Meng-Lin Tsao, Merced, CA (US);
Vaughn Smider, San Diego, CA (US);
Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 802 days.

(21) Appl. No.: 12/734,416

(22) PCT Filed: Oct. 31, 2008

(86) PCT No.: PCT/US2008/012363
§ 371 (c)(1),
(2), (4) Date: Jul. 6, 2010

(87) PCT Pub. No.: WO2009/061369
PCT Pub. Date: May 14, 2009

(65) Prior Publication Data
US 2011/0065596 A1    Mar. 17, 2011

Related U.S. Application Data

(60) Provisional application No. 61/001,681, filed on Nov. 2, 2007, provisional application No. 61/127,262, filed on May 8, 2008, provisional application No. 61/194,773, filed on Sep. 29, 2008.

(51) Int. Cl.
*C40B 40/08* (2006.01)
*C12N 15/10* (2006.01)
*C12N 15/67* (2006.01)
*C40B 40/10* (2006.01)

(52) U.S. Cl.
CPC ........ *C12N 15/1037* (2013.01); *C12N 15/1058* (2013.01); *C12N 15/67* (2013.01); *C40B 40/08* (2013.01); *C40B 40/10* (2013.01)

(58) Field of Classification Search
None
See application file for complete search history.

(56) References Cited

U.S. PATENT DOCUMENTS

| 5,658,727 | A  | 8/1997  | Tsao et al.    |
| 6,323,004 | B1 | 11/2001 | Kang           |
| 6,927,042 | B2 | 8/2005  | Schultz et al. |
| 7,045,337 | B2 | 5/2006  | Schultz et al. |
| 7,083,970 | B2 | 8/2006  | Schultz et al. |

(Continued)

FOREIGN PATENT DOCUMENTS

| WO | WO 02/103012 A1  | 12/2002 |
| WO | WO 2004/029245 A1 | 4/2004  |
| WO | WO 2007/047301 A2 | 4/2007  |

OTHER PUBLICATIONS

Adams et al. (1998) "Potent and selective inhibitors of the proteasome: Dipeptyidyl boronic acids." *Bioorganic & Medicinal Chemistry Letters*, 8: 333-338.

(Continued)

*Primary Examiner* — Christian Boesen
(74) *Attorney, Agent, or Firm* — Quine Intellectual Property Law Group, P.C.

(57) ABSTRACT

The invention provides methods and compositions for screening polypeptide libraries that include variants comprising unnatural amino acids. In addition, the invention provides vector packaging systems and methods for packaging a nucleic acid in a vector. Compositions of vectors produced by the methods and systems are also provided.

29 Claims, 23 Drawing Sheets

(56) References Cited

U.S. PATENT DOCUMENTS

| | | | |
|---|---|---|---|
| 7,129,333 | B2 | 10/2006 | Schultz et al. |
| 7,183,082 | B2 | 2/2007 | Schultz et al. |
| 7,199,222 | B2 | 4/2007 | Shultz et al. |
| 7,217,809 | B2 | 5/2007 | Schultz et al. |
| 7,238,510 | B2 | 7/2007 | Schultz et al. |
| 7,262,040 | B2 | 8/2007 | Schultz et al. |
| 2003/0082575 | A1 | 5/2003 | Schultz et al. |
| 2004/0198637 | A1 | 10/2004 | Schultz et al. |
| 2004/0265952 | A1 | 12/2004 | Deiters et al. |
| 2005/0009049 | A1 | 1/2005 | Chin et al. |
| 2005/0136513 | A1 | 6/2005 | Zhang et al. |
| 2005/0208536 | A1 | 9/2005 | Schultz et al. |
| 2005/0227318 | A1 | 10/2005 | Alfonta et al. |
| 2005/0250183 | A1 | 11/2005 | Schultz et al. |
| 2005/0272121 | A1 | 12/2005 | Xie et al. |
| 2006/0063244 | A1 | 3/2006 | Schultz et al. |
| 2006/0073507 | A1 | 4/2006 | Deiters et al. |
| 2006/0110784 | A1 | 5/2006 | Deiters et al. |
| 2006/0110796 | A1 | 5/2006 | Schultz et al. |
| 2006/0134746 | A1 | 6/2006 | Deiters et al. |
| 2006/0160175 | A1 | 7/2006 | Anderson et al. |
| 2006/0177900 | A1 | 8/2006 | Anderson et al. |
| 2006/0246509 | A1 | 11/2006 | Deiters et al. |
| 2007/0009990 | A1 | 1/2007 | Alfonta et al. |
| 2007/0020634 | A1 | 1/2007 | Anderson et al. |
| 2007/0042461 | A1 | 2/2007 | Anderson et al. |
| 2007/0111193 | A1 | 5/2007 | Zhang et al. |
| 2007/0117184 | A1 | 5/2007 | Schultz et al. |
| 2007/0154952 | A1 | 7/2007 | Chin et al. |
| 2007/0166791 | A1 | 7/2007 | Chin et al. |
| 2007/0172915 | A1 | 7/2007 | Schultz et al. |
| 2007/0178448 | A1 | 8/2007 | Tsao et al. |
| 2007/0178554 | A1 | 8/2007 | Shiva et al. |
| 2007/0184517 | A1 | 8/2007 | Schultz et al. |
| 2007/0238152 | A1 | 10/2007 | Wang et al. |
| 2008/0132681 | A1 | 6/2008 | Hays et al. |
| 2009/0286279 | A1 | 11/2009 | Liu et al. |

OTHER PUBLICATIONS

Badone et al. (1997) "Highly Efficient Palladium-Catalyzed Boronic Acid Coupling Reactions in Water: Scope and Limitations." *Journal of Organic Chemistry*, 62(21): 7170-7173.

Broders et al. (2003) "Hyperphage. Improving antibody presentation on Phage display." *Methods of Molecular Biology*, 205: 295-302.

Brustad et al. (2008) "A Genetically Encoded Boronate-Containing Amino Acid." *Angewandte Chemie Int Ed*, 47(43): 8220-8223.

Cammidge and Crépy (2004) "Synthesis of chiral binaphthalenes using the asymmetric Suzuki reaction." *Tetrahedron*, 60: 4377-4386.

Chan et al. (2003) "Copper promoted C-N and C-O bond cross-coupling with phenyl and pyridylboronates." *Tetrahedron Letters*, 44: 3863-3865.

Chin et al. (2003) "An Expanded Eukaryotic Genetic Code." *Science*, 301: 964-967.

Chin, et al., (2002) "Addition of p-Azido-L-phenylalanine to the Genetic Code of *Escherichia coli*." *Journal of the American Chemistry Society*, 124: 9026-9027.

Deiters et al, (2005) "*In vivo* incorporation of an alkyne into proteins in *Escherichia coli*." *Bioorganic & Medicinal Chemistry Letters*, 15: 1521-1524.

Hoben and Soll (1985) Glutaminyl-tRNA Synthetase of *Escherichia coli*. *Methods in Enzymology*, 113: 55-59.

Huang et al. (2000) "Asymmetric reduction of acetophenone with borane catalyzed by chiral oxazaborolidinone derived from L-a-amino acids," *Synthetic Communications*, 30(13): 2423-2429.

Ishihara and Yamamoto (1999) "Aryiboron Compounds as Acid Catalysts in Organic Synthetic Transformations," *European Journal of Organic Chemistry*, 527-538.

James, et al. (1995) "Chiral discrimination of monosaccharides using a fluorescent molecular sensor," *Nature*, 374(6520): 345-347.

James, et al. (1996) "Saccharide Sensing with Molecular Receptors Based on Boronic Acid," *Angewandte Chemie-International Edition in English*, 35: 1910-1922.

Kemp and Roberts (1975) "New protective groups for peptide synthesis—II the Dobz group boron-derived affinity protection with the p-dihydroxyborylbenzyloxycarbonylamino function." *Tetrahedron Letters*, 52: 4629-4632.

Kinashi, et al. (2002) "Mutagenic effect of borocaptate sodium and boronophenylalanine in neutron capture therapy," *International Journal of Radiation Oncology Biology Physics*, 54(2): 562-567.

Kobayashi et al. (2005) "Structural basis of nonnatural amino acid recognition by an engineered aminoacyl-tRNA synthetase for genetic code expansion." *Proceedings of the National Academy of Sciences of the United States of America, USA*, 102(5): 1366-1371.

Kodama et al. (2006) "Regioselective Carbon-Carbon Bond Formation in Proteins with Palladium Catalysis; New Protein Chemistry by Organometallic Chemistry." *ChemBioChem*, 7: 134-139.

Liu et al. (2007) "Genetic incorporation of unnatural amino acids into proteins in mammalian cells." *Nature Methods*, 4(3): 239-244.

Liu et al. (2008) "Protein evolution with an expanded genetic code." *Proceeding of the National Academy of Science*, 105(46): 17688-17693.

Matthews, et al. (1975) "X-ray crystallographic study of boronic acid adducts with subtilisin BPN' (Novo). A model for the catalytic transition state," *Journal of Biological Chemistry*, 250(18): 7120-7126.

Miyaura and Suzuki (1995) "Palladium-Catalyzed Cross-Coupling Reactions of Organoboron Compounds," *Chemical Reviews*, 95(7): 2457-2483.

Mohler and Czarnik (1993) "Alpha-Amino-Acid Chelative Complexation by an Arylboronic Acid," *Journal of the American Chemical Society*, 115(15): 7037-7038.

Mohler and Czarnik (1994) "Alpha-Amino-Acid Chelative Complexation by an Arylboronic Acid," (erratum) *Journal of the American Chemical Society*, 116(5): 2233-2233.

Ojida et al. (2005) "Suzuki coupling for protein modification." *Tetrahedron Letters*, 46: 3301-3305.

Rondot et al. (2001) "A helper phage to improve single-chain antibody presentation in phage display." *Nature Biotechnology*, 19: 75-78.

Springsteen and Wang (2002) "A detailed examination of boronic acid-diol complexation." *Tetrahedron*, 58: 5291-5300.

Springsteen, et al. (2001) "The Development of Photometric Sensors for Boronic Acids," *Bioorganic Chemistry*, 29: 259-270.

Suzuki (1999) "Recent advances in the cross-coupling reactions of organoboron derivatives with organic electrophiles, 1995-1998," *Journal of Organometallic Chemistry*, 576: 147-168.

Tahtaoui et al. (2007) "Convenient Method to Access New 4,4-Dialkoxy- and 4,4- Diaryloxy-diaza-s-indacene Dyes: Synthesis and Spectroscopic Evaluation." *Journal of Organic Chemistry*, 72: 269-272.

Tian et al. (2004) "A Phage display system with unnatural amino acids." *Journal of the American Chemistry Society.* 126(49): 15962-15963.

Wang and Schultz (2005) "Expanding the Genetic Code," *Angewandte Chemie Int Ed* 44: 34-66.

Wang and Schultz (2002) "Expanding the genetic code." *Chemical Communications* 1-11.

Wang et al. (2000) "A New Functional Suppressor tRNA/Aminoacyl-tRNA Synthetase Pair for the in Vivo Incorporation of Unnatural Amino Acids into Proteins." *Journal of the American Chemical Society*, 122: 5010-5011.

Wang et al. (2001) "Expanding the Genetic Code of *Escherichia coli*." *Science*, 292: 498-500.

Wang et al. (2003) "Addition of the keto functional group to the genetic code of *Escherichia coli*." *Proceeding of the National Academy of Science, USA*, 100(1): 56-61.

Wang et al. (2002) "Boronic Acid-Based Sensors," *Current Organic Chemistry*, 6:1285-1317.

Wang et al. (2006) "Expanding the Genetic Code." *Annual Review of Biophysics and Biomolecular Structure*, 35: 225-249.

Webb and Levy (1995) "A facile oxidation of boronic acids and boronic esters." *Tetrahedron Letters*, 36(29): 5117-5118.

Weston et al. (1998) "Structure-Based Enhancement of Boronic Acid Inhibitors of AmpC b-Lactamase," *Journal of Medicinal Chemistry*, 41(23): 4577-4586.

(56) References Cited

OTHER PUBLICATIONS

Xie and Schultz (2005) "Adding Amino Acids to the Genetic Repertoire." *Current Opinion in Chemical Biology*, 9: 548-554.

Xie and Schultz (2005) "An Expanding Genetic Code." *Methods*, 36: 227-238.

Xie et al. (2007) "A genetically encoded bidentate, metal-binding amino acid." *Angewandte Chemie-International Edition in English*, 46(48): 9239-9242.

Yang et al. (2003) "Boronic Acid Compounds as Potential Pharmaceutical Agents," *Medicinal Research Reviews*, 23(3): 346-368.

Pastrnak et al. (2001) "Phage Selection for Site-Specific Incorporation of Unnatural Amino Acid into Proteins In Vivo." *Bioorganic & Medicinal Chemistry*, 9: 2373-2379.

Liu et al. (2009) "Evolution of Proteins with Genetically Encoded 'Chemical Warheads'" *The Journal of the American Chemical Society*, 131(25): 9616-9617.

Search Report dated Apr. 16, 2012 from EP Application No. 08847822.7.

| Library | CDR3 Encoding Oligo Sequence |
|---|---|
| Germline/TAG-CDR3 | SEQ ID NO: 1  GCGAAA GAN NGG TAG ARY KGG ARC KAC                                       NAC TACTTT<br>SEQ ID NO: 2  GCGAAA GAN <u>NNK</u> NGG TAG ARY KGG ARC KAC <u>NNK</u>                           NAC TACTTT<br>SEQ ID NO: 3  GCGAAA GAN NGG TAY ARY KGG ARC TAG                                       NAC TACTTT<br>SEQ ID NO: 4  GCGAAA GAN <u>NNK</u> NGG TAY ARY KGG ARC TAG <u>NNK</u>                           NAC TACTTT<br>SEQ ID NO: 5  GCGAAA GAN TAG TAY KAT DDY WBK RSK RGT TAT TAY WMC                       NAC TACTTT<br>SEQ ID NO: 6  GCGAAA GAN <u>NNK</u> TAG TAY KAT DDY WBK RSK RGT TAT TAY WMC <u>NNK</u> NAC TACTTT<br>SEQ ID NO: 7  GCGAAA GAN TAT TAG KAT DDY WBK RSK RGT TAT TAY WMC                       NAC TACTTT<br>SEQ ID NO: 8  GCGAAA GAN <u>NNK</u> TAT TAG KAT DDY WBK RSK RGT TAT TAY WMC <u>NNK</u> NAC TACTTT<br>SEQ ID NO: 9  GCGAAA GAN TAT TAY KAT DDY WBK RSK RGT TAG TAY WMC                       NAC TACTTT<br>SEQ ID NO: 10 GCGAAA GAN <u>NNK</u> TAT TAY KAT DDY WBK RSK RGT TAG TAY WMC <u>NNK</u> NAC TACTTT<br>SEQ ID NO: 11 GCGAAA GAN TAT TAY KAT DDY WBK RSK RGT TAT TAG WMC                       NAC TACTTT<br>SEQ ID NO: 12 GCGAAA GAN <u>NNK</u> TAT TAY KAT DDY WBK RSK RGT TAT TAG WMC <u>NNK</u> NAC TACTTT<br>SEQ ID NO: 13 GCGAAA GAN GAC TAG RGT RAC TMC                                           NAC TACTTT<br>SEQ ID NO: 14 GCGAAA GAN <u>NNK</u> GAC TAG RGT RAC TMC <u>NNK</u>                               NAC TACTTT<br>SEQ ID NO: 15 GCGAAA GAN GAC TAC RGT RAC TAG                                           NAC TACTTT<br>SEQ ID NO: 16 GCGAAA GAN <u>NNK</u> GAC TAC RGT RAC TAG <u>NNK</u>                               NAC TACTTT<br>SEQ ID NO: 17 GCGAAA GAN NGT RGA TAG RGY <u>KRY</u> RRT <u>TAC</u>                                   NAC TACTTT<br>SEQ ID NO: 18 GCGAAA GAN <u>NNK</u> NGT RGA TAG RGY <u>KRY</u> RRT <u>TAC NNK</u>                       NAC TACTTT<br>SEQ ID NO: 19 GCGAAA GAN NGT RGA <u>KAY</u> RGY TAG RRT <u>TAC</u>                                   NAC TACTTT<br>SEQ ID NO: 20 GCGAAA GAN <u>NNK</u> NGT RGA <u>KAY</u> RGY TAG RRT <u>TAC NNK</u>                       NAC TACTTT<br>SEQ ID NO: 21 GCGAAA GAN NGT RGA <u>KAY</u> RGY <u>KRY</u> RRT TAG                                   NAC TACTTT<br>SEQ ID NO: 22 GCGAAA GAN <u>NNK</u> NGT RGA <u>KAY</u> RGY <u>KRY</u> RRT TAG <u>NNK</u>                       NAC TACTTT<br>SEQ ID NO: 23 GCGAAA GAN GRGTAGAGCAGCAGCTSG<u>TMC</u>                                         NAC TACTTT<br>SEQ ID NO: 24 GCGAAA GAN <u>NNK</u> GRGTAGAGCAGCAGCTSG<u>TMC</u> <u>NNK</u>                             NAC TACTTT<br>SEQ ID NO: 25 GCGAAA GAN GRG<u>TA</u>TAGCAGCAGCTSGTAG                                         NAC TACTTT<br>SEQ ID NO: 26 GCGAAA GAN <u>NNK</u> GRG<u>TA</u>TAGCAGCAGCTSGTAG <u>NNK</u>                             NAC TACTTT |
| NNK/TAG-CDR3 | SEQ ID NO: 27 GCGAAA GAN TAG NNK NNK                     NAC TACTTT<br>SEQ ID NO: 28 GCGAAA GAN NNK TAG NNK                     NAC TACTTT<br>SEQ ID NO: 29 GCGAAA GAN NNK NNK TAG                     NAC TACTTT<br>SEQ ID NO: 30 GCGAAA GAN TAG NNK NNK NNK                 NAC TACTTT<br>SEQ ID NO: 31 GCGAAA GAN NNK TAG NNK NNK                 NAC TACTTT<br>SEQ ID NO: 32 GCGAAA GAN NNK NNK TAG NNK                 NAC TACTTT<br>SEQ ID NO: 33 GCGAAA GAN NNK NNK NNK TAG                 NAC TACTTT<br>SEQ ID NO: 34 GCGAAA GAN TAG NNK NNK NNK NNK             NAC TACTTT<br>SEQ ID NO: 35 GCGAAA GAN NNK TAG NNK NNK NNK             NAC TACTTT<br>SEQ ID NO: 36 GCGAAA GAN NNK NNK TAG NNK NNK             NAC TACTTT<br>SEQ ID NO: 37 GCGAAA GAN NNK NNK NNK TAG NNK             NAC TACTTT<br>SEQ ID NO: 38 GCGAAA GAN NNK NNK NNK NNK TAG             NAC TACTTT<br>SEQ ID NO: 39 GCGAAA GAN TAG NNK NNK NNK NNK NNK NAC TACTTT<br>SEQ ID NO: 40 GCGAAA GAN NNK TAG NNK NNK NNK NNK NAC TACTTT<br>SEQ ID NO: 41 GCGAAA GAN NNK NNK TAG NNK NNK NNK NAC TACTTT<br>SEQ ID NO: 42 GCGAAA GAN NNK NNK NNK TAG NNK NNK NAC TACTTT<br>SEQ ID NO: 43 GCGAAA GAN NNK NNK NNK NNK TAG NNK NAC TACTTT<br>SEQ ID NO: 44 GCGAAA GAN NNK NNK NNK NNK NNK TAG NAC TACTTT |
| NNK-CDR3 | SEQ ID NO: 45 GCGAAA GAN NNK NNK NNK                         NAC TACTTT<br>SEQ ID NO: 46 GCGAAA GAN NNK NNK NNK NNK                     NAC TACTTT<br>SEQ ID NO: 47 GCGAAA GAN NNK NNK NNK NNK NNK             NAC TACTTT<br>SEQ ID NO: 48 GCGAAA GAN NNK NNK NNK NNK NNK NNK NAC TACTTT |

Fig. 5

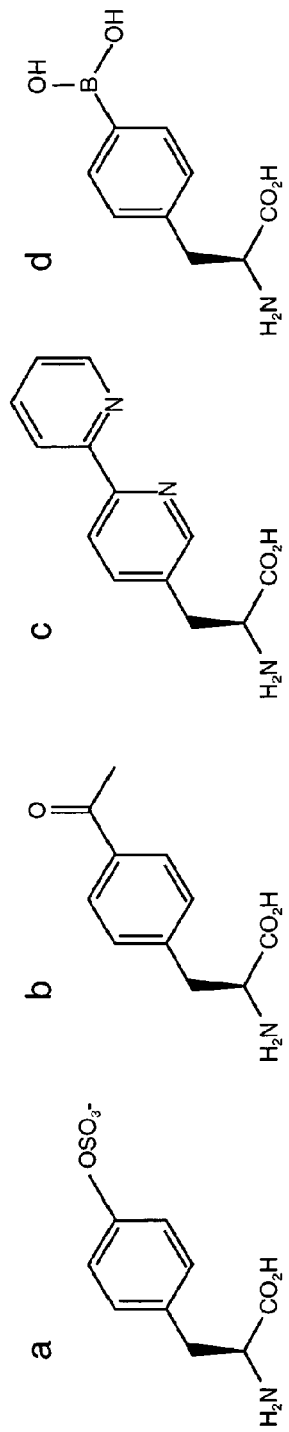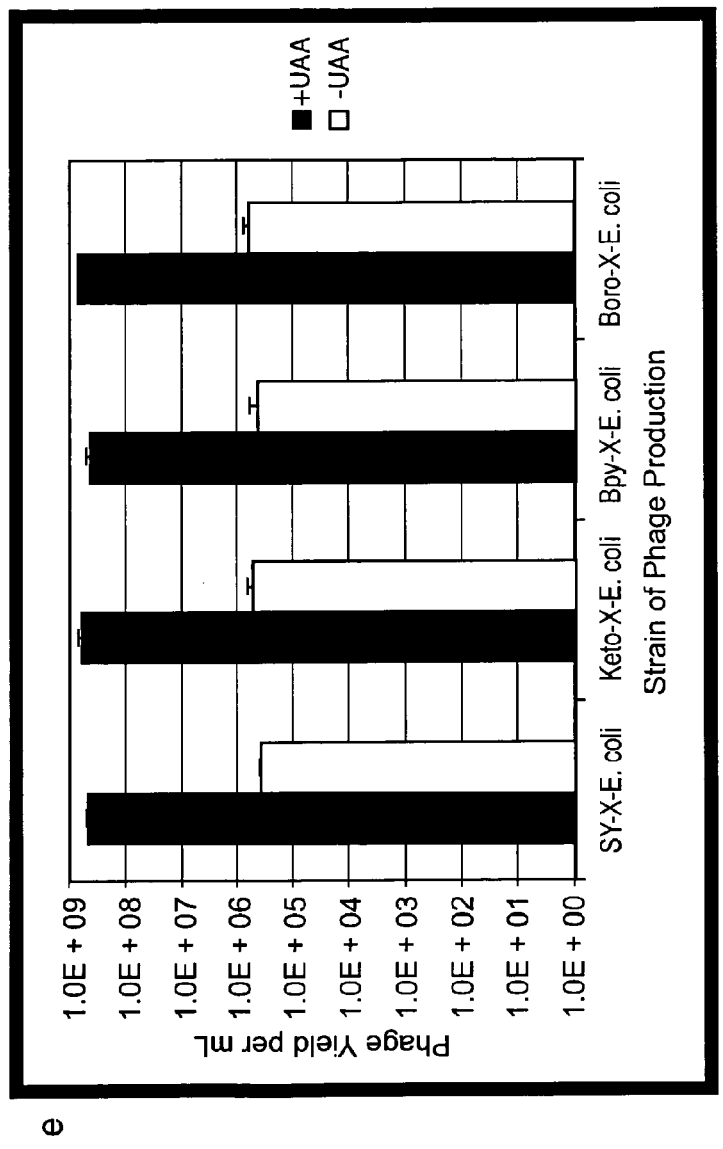
Fig. 7

DIRECTED EVOLUTION USING PROTEINS COMPRISING UNNATURAL AMINO ACIDS

CROSS-REFERENCE TO RELATED APPLICATIONS

This application claims priority to and benefit of U.S. Provisional Patent Application Ser. No. 61/001,681, entitled, "Directed evolution using proteins comprising unnatural amino acids", by Liu, et al., filed on Nov. 2, 2007, Provisional Patent Application Ser. No. 61/127,262, entitled, "Directed evolution using proteins comprising unnatural amino acids", by Liu, et al., filed on May 8, 2008, and U.S. Provisional Patent Application Ser. No. 61/194,773, entitled, "Directed evolution using proteins comprising unnatural amino acids", by Liu, et al., filed on Sep. 29, 2008, the contents of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support from the National Institutes of Health under Grant No. 5R01 GM62159 and from a National Science Foundation Predoctoral Fellowship. The government has certain rights to this invention.

FIELD OF THE INVENTION

This invention relates to the field of protein chemistry, e.g., translation biochemistry. The invention relates to methods and compositions for screening libraries of polypeptide variants comprising unnatural amino acids. The invention also relates to systems, compositions and methods for producing vectors that comprise vector proteins and/or heterologous proteins into which unnatural amino acids have been incorporated.

BACKGROUND OF THE INVENTION

Proteins carry out virtually all of the complex processes of life, from photosynthesis to signal transduction and the immune response. To understand these intricate activities, it would be useful to learn how proteins interact with other molecules to perform their functions. Polypeptide library screening techniques are extremely valuable tools in investigating and manipulating these molecular interactions. In general, screening a polypeptide library relies on the expression of a plurality of polypeptide variants followed by the isolation and amplification of those variants that exhibit a function of interest, e.g., variants that bind to a particular ligand. However, isolating such variants can be critically dependent upon maintaining library diversity.

Differential expression rates among the polypeptide variants in a library can be detrimental to the maintenance of library diversity, and, therefore, to the selection of functional sequences. For example, certain highly expressed variants can become enriched in a population following repeated cycles screening, isolation, and amplification not because they meet the screening criterion, but because they are overrepresented due solely to growth advantages. As a consequence, desirable variants that are expressed at lower levels can become underrepresented or can even become lost. This is particularly true of polypeptide variants comprising unnatural amino acids due to an inherent in vivo expression bias for proteins containing only natural amino acids.

What is needed in the art are new strategies for controlling the expression levels throughout a population of expressed polypeptide variants, especially populations that include variants comprising unnatural amino acids, while avoiding adverse effects on the diversity of variants in the population. The invention described herein fulfills these and other needs, as will be apparent upon review of the following disclosure.

SUMMARY

The incorporation of unnatural amino acids with unique functional groups into polypeptides in a site-specific manner has made it possible to generate polypeptides that exhibit enhanced or novel steric, chemical, or biological properties. Such desirable polypeptide candidates can be identified by screening polypeptide libraries that include variants that comprise unnatural amino acids. However, in the absence of controlled expression of all the polypeptide variants in a library, desirable variants, especially those comprising unnatural amino acids, can become underrepresented or lost.

There is a need for new strategies for regulating the expression levels throughout a population of expressed peptide variants. The present invention provides novel compositions for polypeptide libraries that include variants that comprise unnatural amino acids and novel methods for screening such libraries. In addition, the invention also provides methods and systems for the packaging of novel vectors that can be used to develop the above-mentioned polypeptide libraries.

The invention provides a method of screening a library of polypeptide variants for one or more functions of interest. The method includes normalizing expression of a plurality of polypeptide variants in a library such that the average ratio of expressed variants is 10:1 or less. Optionally, the ratio of expressed variants can be 5:1 or less, or 1:1. The method also includes selecting the variants exhibiting the function of interest from the plurality such that observed differences in the function of interest correlate with differences in activity of the variants. The library can include a plurality of polypeptide variants that includes at least one polypeptide variant that includes at least one unnatural amino acid. Optionally, the polypeptide variants in the plurality can each comprise at least one unnatural amino acid. Screening a library of polypeptide variants can optionally include screening a library of any one of the kinds of polypeptide variants as discussed herein.

In the method, the sensitivity of the selection can optionally be improved when expression of variants is normalized. Selecting the variants exhibiting the function of interest can include selecting differences in the function of interest that are detectable when the ratio of expressed variants is 1:10 or less. Optionally, selecting the variants exhibiting the function of interest can include selecting differences in the function of interest that are detectable when the ratio of expressed variants is 1:5 or less.

The present invention also provides a recombinant polypeptide expression library that includes a plurality of expressed polypeptide variants. The expressed polypeptide variants in the library can optionally include any one of the kinds of polypeptide variants as discussed herein. Each of the plurality of variants can optionally be present in the library at molar ratio of 10:1 or less, 5:1 or less, or 1:1. For example, the recombinant polypeptide expression library can comprise a plurality of recombinant M13-derived phage wherein each phage displays a recombinant polypeptide variant, e.g., an antibody fragment variant, on its outer surface. Optionally, the recombinant polypeptide expression library can comprise a plurality of multivalent recombinant M13-derived phage wherein each phage displays more than one of the same recombinant polypeptide variant, e.g., an antibody fragment variant, on its outer surface.

Optionally, at least one, at least two, at least three, or more than three of the variants can include at least one unnatural amino acid residue. At least one of the polypeptide variants can optionally comprise at least one unnatural amino acid residue, at least two different unnatural amino acid residues, or more than two different unnatural amino acid residues. The polypeptide variants can optionally include any of the unnatural amino acids discussed herein.

A nucleic acid expression library is also provided by the invention. The nucleic acid expression library includes a plurality of recombinant nucleic acid expression constructs that can be expressed such that polypeptide products of the constructs are present in the library at a ratio of 10:1 or less, 5:1 or less, or 1:1. The polypeptide products expressed by the constructs can optionally include any one of the kinds of polypeptide variants as discussed herein.

The coding region of at least one of the expression constructs can include at least one selector codon such that at least one unnatural amino acid residue is incorporated into at least one of the polypeptide products. The selector codon can include a stop codon, a four-base codon, a rare codon, or a non-coding codon. The unnatural amino acid residue incorporated into at least one of the polypeptide products expressed by the recombinant nucleic acid expression constructs can optionally include any of the unnatural amino acids discussed herein.

In addition, the invention provides a library of expression products that includes a plurality of polypeptide variants. The polypeptide variants can optionally include any one of the polypeptide variants as discussed herein. Each of the polypeptide variants can include at least one unnatural amino acid. The unnatural amino acids can optionally include any of the unnatural amino acids discussed herein. The variants can optionally be present in the library at a ratio of 10:1 or less, 5:1 or less, or 1:1.

One of the most widely used technologies for screening libraries of polypeptide variants is phage display, a technique that can readily be used with the methods and compositions described above. Phage display is an in vitro selection technique in which a gene encoding a polypeptide variant is fused to that of a bacteriophage coat, or capsid, protein. When expressed, the encoded fusion protein is displayed on the phage's exterior surface, while the nucleic acid encoding the fusion protein resides within the phage itself. The physical link between phenotype and genotype in phage display is advantageous not only because it allows selective isolation and amplification of those phages encoding a desired polypeptide variant, it also permits large numbers of variants to be screened in parallel. The aspects of the invention discussed below provide novel systems and methods for vector assembly and compositions for novel vectors that are useful for phage display.

A novel vector packaging system that includes a vector nucleic acid is provided by the invention. The vector nucleic acid includes or encodes a packaging site and encodes a target polypeptide that includes at least one selector codon. The vector packaging system also includes a complementation nucleic acid that encodes a packaging or specificity polypeptide that includes at least one selector codon. Optionally this selector codon can be the same as the selector codon encoded by the target polypeptide. The packaging or specificity polypeptide can be packaged with the vector nucleic acid, or with a copy or a transcript of the vector nucleic acid, during the assembly of the vector. In addition, the vector packaging system includes an orthogonal tRNA (O-tRNA) that is charged with an unnatural amino acid. The O-tRNA can recognize the selector codons encoded by the target polypeptide and/or packaging or specificity polypeptide and permits their translation.

The vector nucleic acid of the vector packaging system can encode target polypeptide comprising a fusion protein. The fusion protein can optionally include a ribosomally synthesized antibody fragment, or derivative thereof, and/or a complementarity determining region (CDR). The selector codon encoded by the target polypeptide and/or by the packaging or specificity polypeptide can optionally include a stop codon, a 4-base codon, a rare codon, or a non-coding codon. The packaging or specificity polypeptide of the vector packaging system can comprise a viral capsid or envelope protein, e.g., an M13 phage pIII capsid protein. The vector packaging system can optionally comprise an in vitro translation system. In another aspect, vector packaging system can optionally comprise a cell, e.g., a mammalian, insect, bacterial or E. coli cell. The system can include an orthogonal aminoacyl-tRNA synthetase capable of charging the orthogonal tRNA with an unnatural amino acid, e.g., bipyridyl alanine, and an unnatural amino acid, e.g., bipyridyl alanine, p-boronophenylalanine, sulfotyrosine, or para-acetylphenylalanine.

In one embodiment, the vector packaging system includes a phagemid comprising an M13 phage packaging sequence. The phagemid can encode a fusion protein which can include a selector codon, e.g., a fusion protein comprising an antibody fragment that includes at least one selector codon. The vector packaging system also includes a plasmid encoding a mutant pIII polypeptide that comprises at least one selector codon, optionally the same selector codon as the fusion protein. The mutant pIII polypeptide is packaged with a copy of the phagemid. In addition, the vector packaging system includes an orthogonal tRNA that is charged with an unnatural amino acid residue. The charged orthogonal tRNA recognizes the selector codon and permits the translation of the mutant pIII polypeptide and of the antibody fragment fusion protein by the vector packaging system.

In a related aspect, the invention provides a vector that includes a packaged nucleic acid encoding a target polypeptide and the target polypeptide encoded by the packaged nucleic acid. The vector can comprise a viral capsid and can be derived from a mammalian virus, an adenovirus, an adeno-associated virus, a retrovirus, a herpes virus, an insect virus, a baculovirus, or a bacteriophage, e.g., a recombinant M13-derived bacteriophage. The packaged nucleic acid can comprise or encode a packaging site, and the target polypeptide encoded by the packaged nucleic acid can comprise a fusion protein, e.g., a fusion protein comprising a ribosomally synthesized antibody fragment, a derivative thereof, and/or a complementarity determining region. The target polypeptide is optionally displayed on the outer surface of the vector. In addition, the vector includes a specificity polypeptide which confers host cell specificity to the vector and which comprises at least one unnatural amino acid residue. The specificity polypeptide can optionally comprise a viral capsid protein, e.g., an M13 phage pIII protein, or a viral envelope protein.

In another embodiment, a vector includes a packaged nucleic acid which encodes a target polypeptide that includes at least one selector codon and a target polypeptide encoded by the packaged nucleic acid which includes at least one unnatural amino acid. The target polypeptide is optionally displayed on the outer surface of the vector. In addition, the vector includes a packaging or specificity polypeptide that packages the nucleic acid, or that confers host cell specificity to the vector. The packaging or specificity polypeptide includes at least one unnatural amino acid, optionally the same unnatural amino acid as the target polypeptide.

For example, a vector can comprise a recombinant M13-derived phage that includes a phagemid encoding a fusion protein comprising an antibody fragment that comprises at least one selector codon. The vector can also include a fusion protein that includes an antibody fragment that contains at least one unnatural amino acid. The fusion protein can be displayed on the outer surface of the recombinant M13-derived phage. In addition, the vector can include a pIII polypeptide that includes at least one same unnatural amino acid, e.g., any unnatural amino acid described herein, as the fusion protein.

The present invention provides a method for packaging a vector nucleic acid. The method comprises expressing a vector nucleic acid to produce a target polypeptide including at least one unnatural amino acid and expressing a complementation nucleic acid to produce a packaging or specificity polypeptide including at least one same unnatural amino acid as the target polypeptide. The method also includes permitting the vector nucleic acid, or a copy or transcript thereof, to assemble with the packaging or specificity polypeptide and the target polypeptide, thereby packaging the vector nucleic acid.

In the method, the vector nucleic acid to be expressed can comprise or encode a packaging site and a target polypeptide which includes at least one selector codon. The complementation nucleic acid to be expressed can comprise a complementation nucleic acid that encodes a packaging or specificity polypeptide that comprises at least one same selector codon as the target polypeptide. The vector nucleic acid and/or the complementation nucleic acid can be expressed using any of a variety of approaches, including transforming, transducing, conjugating, stably transfecting or transiently transfecting a cell with the vector nucleic acid and/or the complementation nucleic acid. Expressing the vector nucleic acid to produce the target polypeptide or expressing the complementation nucleic acid to produce the packaging or specificity polypeptide includes inducing the synthesis of an RNA which encodes the target polypeptide and/or the packaging or specificity polypeptide.

Permitting the vector nucleic acid, or a copy or transcript thereof, to assemble with the packaging or specificity polypeptide and the target polypeptide can comprise, e.g., culturing an *E. coli* strain which carries the vector nucleic acid, expressing the vector nucleic acid carried by the *E. coli* strain to produce the target polypeptide, providing the complementation nucleic acid, e.g., by infecting the *E. coli* strain with a helper phage carrying the complementation nucleic acid, and expressing the complementation nucleic acid to produce the packaging or specificity polypeptide. Packaging the vector nucleic acid includes permitting the vector nucleic acid to assemble with an additional polypeptide, e.g., a polymerase, a viral matrix protein, or a viral core protein. The steps of the method are optionally performed in a cell, e.g., a mammalian cell, an insect cell, a bacterial cell, or an *E. coli* cell.

For example, in one embodiment, a method for packaging a vector plasmid the method comprises expressing the vector plasmid to produce a fusion protein comprising an antibody fragment. The fragment can comprise at least one unnatural amino acid. The method includes expressing a complementation plasmid to produce a mutant pIII protein that comprises at least one same unnatural amino acid as the fusion protein. A copy of the vector plasmid is permitted to assemble with the mutant pIII and the fusion protein, thereby packaging the vector plasmid.

Kits are also a feature of the invention. Kits can include any of the compositions herein, e.g., packaged in an appropriate container, along with instructional materials, e.g., to practice the methods of the invention.

Those of skill in the art will appreciate that the methods, kits, systems, and compositions provided by the invention can be used alone or in combination. For example, compositions comprising a library of normalized expression products that, e.g., each comprise at least one unnatural amino acid, can be screened by any of the methods described herein for a polypeptide variant for one or more function of interest. Alternately or additionally, these libraries can be produced by any of the vector packaging systems provided by the invention. One of skill will appreciate further combinations of the features of the invention noted herein.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an aminoacyl tRNA synthetase (RS)" includes a combination of two or more RS molecules, unless context dictates otherwise; reference to "bacteria" includes mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

Complementation nucleic acid: The term "complementation nucleic acid" refers to the nucleic acid that encodes the packaging or specificity polypeptide. An example of a complementation nucleic acid includes the genome of the recombinant M13-derived phage M13KO7, which encodes the pIII protein that permits M13 phage assembly and infectivity.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, a DNA molecule can encode an RNA molecule, e.g., by the process of transcription incorporating a DNA-dependent RNA polymerase enzyme. Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Fusion protein: As used herein, a "fusion protein" refers to the expression product of two or more nucleic acid molecules that are not natively expressed together as one expression product. For example, a native protein X comprising subunit A and subunit B, which are not natively expressed together as one expression product, is not a fusion protein. However, recombinant DNA methods known in the art may be used to express subunits A and B together as one expression product to yield a fusion protein comprising subunit A fused to subunit B. A fusion protein may comprise amino acid sequences that are heterologous, e.g., not of the same origin, not of the same protein family, not functionally similar, and the like.

Library: The term "library" is used according to its common usage in the art, to denote a collection of molecules of interest. For example, a polypeptide library is a collection of expressed polypeptides or polypeptide variants. The polypeptide variants of the invention optionally contain randomized or selectively modified residues, such that each library comprises or encodes a repertoire of related polypeptides, wherein individual polypeptides differ in sequence from each other. The same principle applies to libraries developed for selection, such as by phage display.

Normalized library: As used herein, the term "normalized library" refers to a library comprising a collection of molecules of interest in which the representation of each molecule is, on average, within a specified range, e.g. about 10:1, 9:1, 8:1, 7:1, 6:1, 5:1, 4:1, 3:1, 2:1, 1:1, or about 0.9:1, relative to the other molecules in the library.

Orthogonal: As used herein, the term "orthogonal" refers to a molecule, e.g., an orthogonal tRNA (O-tRNA) and/or an orthogonal aminoacyl-tRNA synthetase (O-RS), that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second "cognate" orthogonal molecule can be introduced into the cell that functions with the first orthogonal molecule. For example, an orthogonal tRNA/RS pair includes introduced complementary components that function together in the cell with an efficiency, e.g., 45% efficiency, 50% efficiency, 60% efficiency, 70% efficiency, 75% efficiency, 80% efficiency, 90% efficiency, 95% efficiency, or 99% or more efficiency, as compared to that of a control, e.g., a corresponding tRNA/RS endogenous pair, or an active orthogonal pair, e.g., a tyrosyl orthogonal tRNA/RS pair. Thus, an O-RS/O-tRNA pair work together with good efficiency, in that the O-RS aminoacylates the O-tRNA with reasonable efficiency, while the O-RS does not aminoacylate endogenous tRNAs or at least poorly aminoacylates endogenous tRNAs, while the O-tRNA is poorly or not at all aminoacylated by endogenous RS.

Packaging site: A packaging site is a cis regulatory element in the sequence of the vector nucleic acid that permits the efficient and specific incorporation of the vector nucleic acid into the interior of the assembling vector particle, e.g., a viral capsid.

Packaging or specificity polypeptide: As used herein, the term "packaging or specificity polypeptide" refers to a polypeptide that is an essential component of the architecture of the outermost structure the vector particle and/or that determines the vector's host range. Examples of packaging or specificity polypeptides include the M13 phage pIII polypeptide, which plays a central role in both M13 phage assembly and M13 infection of $F^+$ E. coli, lambda phage gpE, which plays a central role in lambda phage assembly, and herpesvirus VP5, which is essential for the stability of the herpesvirus capsid.

Polypeptide: A polypeptide is any oligomer of amino acid residues (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acid residues. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Specificity polypeptide: As used herein, the term "specificity polypeptide" refers to a polypeptide that determines a vector's host range. Examples of specificity polypeptides include the M13 phage pIII polypeptide, which permits M13 to infect E. coli, and lambda phage J protein, which permits lambda infection of E. coli.

Target polypeptide: As used herein, the term "target polypeptide" refers to the polypeptide(s) encoded by the vector nucleic acid (e.g., a pIII fusion protein in M13, a gp64 fusion protein in baculovirus, a 10b fusion protein in T7 phage, and a D fusion protein in lambda phage).

Unnatural amino acid: As used herein, the term "unnatural amino acid" refers to any amino acid, modified amino acid, and/or amino acid analogue that is not one of the 20 common naturally occurring amino acids or selenocysteine or pyrolysine. For example, the unnatural amino acids bipyridyl alanine and sulfotyrosine find use with the invention.

Vector: A "vector" is a composition of matter which comprises a nucleic acid and which optionally can be used to deliver the isolated nucleic acid to the interior of a host cell. Numerous vectors are known in the art including, but not limited to, linear polynucleotides, polynucleotides associated with ionic or amphiphilic compounds, bacteriophage, plasmids, and viruses. Thus, the term "vector" includes, but is not limited to, an autonomously replicating plasmid or a virus, which can be packaged or naked. Examples of virus vectors include, but are not limited to, adenoviral vectors, adeno-associated virus vectors, retrovirus vectors, and other recombinant viruses.

Vector Nucleic Acid: As used herein, a "vector nucleic acid" refers to the nucleic acid that encodes the target polypeptide, which nucleic acid, or a copy or transcript thereof, is packaged in the interior of the vector and is delivered by the vector to the interior of a host cell.

BRIEF DESCRIPTION OF THE DRAWINGS

FIG. 5 illustrates oligonucleotide sequences (SEQ ID NOs: 1-48) that were used to generate three libraries of Fab variants comprising unnatural amino acids.

FIG. 7a-d depict the structures of four unnatural amino acids that were used in experiments described in Example 2. FIG. 7e-f depict the results of experiments performed to confirm that scFv-pIII fusion proteins comprising unnatural amino acids can be displayed on the surfaces of the M13-derived phage used in Example 2.

DETAILED DESCRIPTION

Figure 1:
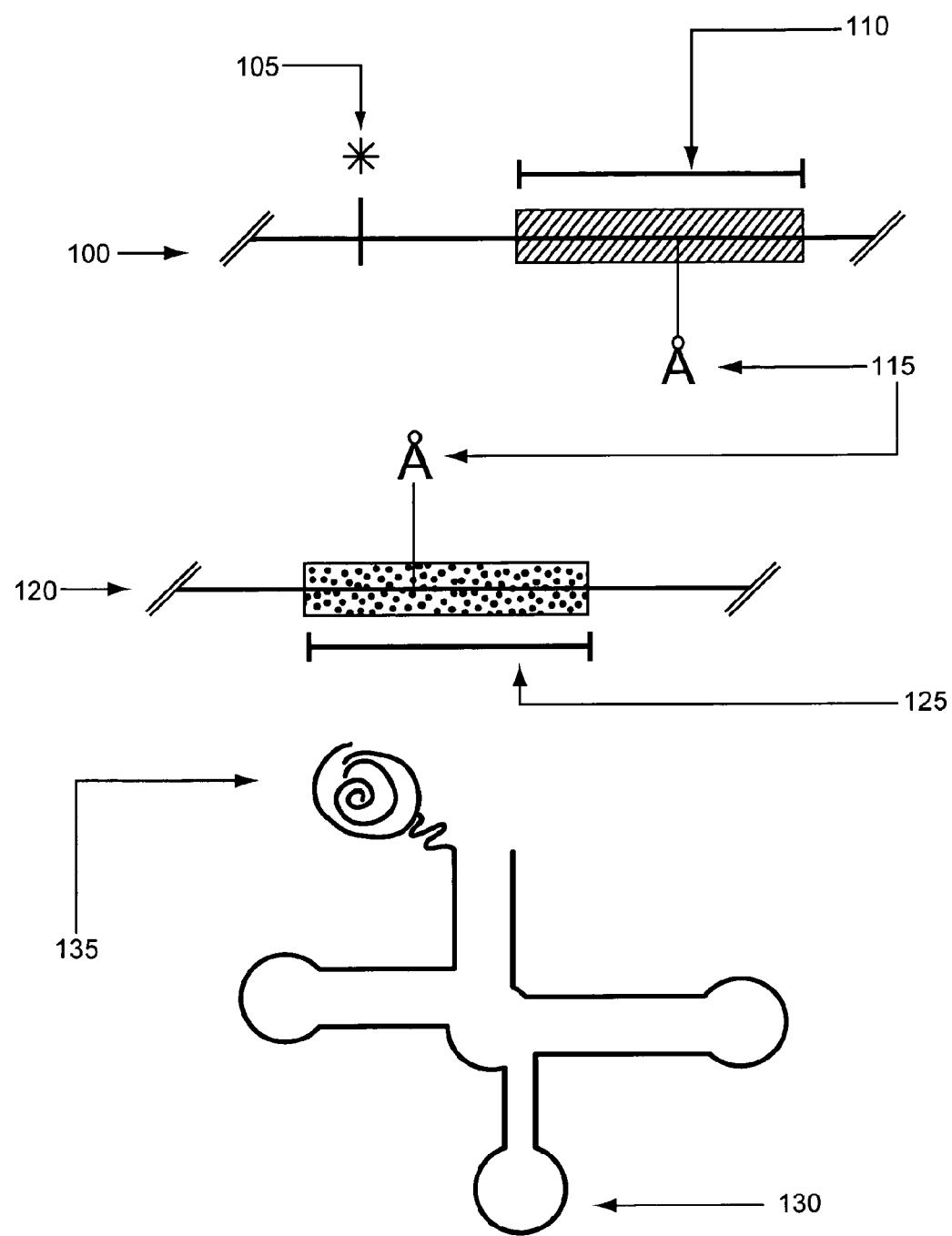
FIG. 1 is a schematic illustration of the vector packaging system provided by the invention.

The present invention facilitates the production of normalized polypeptide expression libraries by harnessing an inherent in vivo expression bias against polypeptides comprising unnatural amino acids. Due to this inherent bias, polypeptide variants in a library that comprise unnatural amino acids are ordinarily underrepresented, lost, or otherwise undetected by the assay used to screen for the function of interest. However, the invention relies on the incorporation of at least one same unnatural amino acid into a polypeptide required for viability as that incorporated into a screenable moiety to normalize the expression of all the variants in a library.

The methods and compositions provided by the invention can be useful in reducing the redundancy of abundant polypeptide variants in a library and in boosting the representation of rare variants, e.g., variants comprising unnatural amino acids that can possess enhanced properties of interest. Because maintaining library diversity is one of the major challenges of making and screening most polypeptide expression libraries, the invention is useful for and generally applicable to a wide range of prokaryotic, eukaryotic, and archaebacterial polypeptide library screening systems.

In a preferred embodiment described herein, the invention finds use with phage display libraries. These libraries include, e.g., an M13 phage pIII polypeptide comprising at least one same unnatural amino acid as the subset of the displayed pIII fusion polypeptide variants that comprise unnatural amino acids. Such libraries are typically screened via multiple selection rounds in which phage exhibiting a function of interest, e.g., binding to a ligand, are isolated and amplified in bacteria, e.g., *E. coli*. The invention provides methods and systems for the packaging of novel vectors that can be used to produce normalized polypeptide libraries.

Normalizing Polypeptide Libraries

In one aspect, the invention relates to normalizing the expression of the variants in a polypeptide library by incorporating at least one same unnatural amino acid into a polypeptide required for viability as that incorporated into a screenable variant. As a result, every member of the library is subject to the same growth disadvantage that would ordinarily only affect those variants comprising unnatural amino acid residues. The methods provided by the invention include normalizing the expression of a plurality of polypeptide variants in the library, wherein the average ratio of expressed variants is optionally about 10:1, 9:1, 8:1, 7:1, 6:1, 5:1, 4:1, 3:1, 2:1, 1:1, or, e.g., about 0.9:1. The methods can be used with protein probing systems, e.g., λgt11, surface display systems, e.g., phage display, baculovirus display, yeast cell surface display, mammalian cell surface display, insect cell surface display, E. coli cell surface display, yeast and mammalian two-hybrid systems, or the like.

In one preferred embodiment, phage display systems (Smith, G. P. (1985) "Filamentous fusion phage: novel expression vectors that display cloned antigens on the virion surface." Science; 228:1315-7, reviewed in Sergeeva, A., et al. (2006) "Display technologies: application for the discovery of drug and gene delivery agents." Adv. Drug Deliv. Rev. 58:1622-54) can be adapted according to the invention. In a preferred embodiment, the same unnatural amino acid residue that is incorporated into a subset of the polypeptide variants in a phage display library, e.g., a recombinant M13-derived phage display library, is also incorporated into a phage packaging or specificity polypeptide, e.g., an M13 pIII polypeptide. Because phage viability relies, in part, on the assembly of the packaging or specificity polypeptide, e.g., pIII, into the capsid, the polypeptide variants comprising only natural amino acids no longer have the growth advantage that would result in their being over-represented the library. A more extended discussion of phage display embodiments is presented separately below.

In another useful embodiment, the expression levels of the polypeptide variants produced by a λgt11 library (Young, R. A., et al. (1983) "Efficient isolation of genes by using antibody probes." Proc Natl. Acad. Sci. U.S.A. 80:1194-8) that comprise unnatural amino acids can be normalized with those of variants comprising only natural amino acids by the same principle. In one embodiment, this can be accomplished by replacing the λ phage gene encoding cI857, a temperature sensitive cI mutant, with an allele that encodes a functional temperature sensitive cI mutant that also comprises at least one same unnatural amino acid as that included in the variants in the library.

The expression levels of members of a yeast two-hybrid (Y2H) "prey" library comprising variants that include unnatural amino acids can be normalized by replacing the endogenous copy of an essential Saccharomyces cerevisiae gene, e.g., PDA1, with a mutant allele which complements the wild type gene's function and which produces a protein that comprises at least one same unnatural amino acid as that in the variants. (The yeast two-hybrid system is explicated in detail in Fields, S., et al. (1989) "A novel genetic system to detect protein-protein interactions." Nature. 340: 245-246; Armour, C. D., et al. (2005) "From drug to protein: using yeast genetics for high-throughput target discovery." Curr. Opin. Chem. Biol. 9:20-24; and Miller, J., et al. (2004) "Using the yeast two-hybrid system to identify interacting proteins." Methods Mol. Biol. 261: 247-262). In an alternate embodiment for the same system, normalization of the Y2H "prey" library members' expression levels can be achieved by replacing the endogenous copy of the metabolic gene URA1, which is essential for UMP synthesis, with a complementary allele comprising at least one same unnatural amino acid as found in the variants, and performing the library screen under conditions in which uracil auxotrophs cannot grow.

In a similar manner, normalizing the expression of polypeptide variants in, e.g., a mammalian cell surface display library (Wolkowicz, R., et al. (2005) "A random peptide library fused to CCR5 for selection of mimeotopes expressed on the mammalian cell surface via retroviral vectors." J. Biol. Chem., 280:15195-15201) can be accomplished by introducing a Neo allele which encodes a functional aminoglycoside 3'-phosphotransferase protein comprising at least one unnatural amino acid into the genome of an appropriate cell line. The cells can than be grown in appropriate medium supplemented with gentamicin. The cells' gentamicin resistance would rely on the incorporation of at least one same unnatural amino acid residue into aminoglycoside 3'-phosphotransferase as into the screenable polypeptide variants that comprise unnatural amino acids. In this manner, the growth rate, and, therefore, the expression levels, of each polypeptide variant in the library would be more homogenous.

This aspect of the invention is generally applicable and can be similarly adapted to other systems or techniques in which the normalization of the expression levels of polypeptide variants would be useful, including anchored and anchor-less periplasmic expression systems (U.S. Pat. No. 7,094,571). In this technique, a library of polypeptide variants can be constructed and expressed in Gram negative bacteria optionally as fusion proteins that can be anchored to the periplasmic face of the inner membrane or as polypeptides targeted to the periplasmic compartment. Permeabilization of the bacterial outer membrane, via chemical, physical, genetic, or other treatments renders the polypeptide variants anchored on the membrane or accessible to target molecules added to the external solution. When such a library comprises variants made up of unnatural amino acid residues, as in the present invention, the expression of all variants can be normalized, e.g., by introducing a gene encoding a functional β-lactamase comprising an unnatural amino acid into an appropriate bacterial strain, and performing the screen in media supplemented with ampicillin.

Normalizing Phage Display Libraries

In a preferred embodiment, the invention finds use with phage display, e.g., M13 phage display, a technique widely used in polypeptide library screening protocols. See, e.g., Smith, G. P. and Petrenko, V. A. (1997) "Phage Display." Chem. Rev. 97: 391-410; Sidhu, S. S. (2001) "Engineering M13 for phage display." Biomolecular Engineering, 18: 57-63; Rodi, D. J. and Malakowski, L. (1999) "Phage-display technology—finding a needle in a vast molecular haystack." Curr. Opin. Biotechnol. 10: 87-93; and Willats, W. G. T. (2002) "Phage display: practicalities and prospects." Plant Molecular Biology, 50: 837-854. Generally, the display of polypeptides variants in a phage display library is accomplished by fusing a polypeptide variant of interest with a phage capsid (coat) protein, or a fragment, mutant or other variant of a capsid protein. These capsid proteins can include pIII, pVI, pVII, pVIII and pIX. For the purpose of demonstrating the invention, the Example herein describes the generation of phage-displayed fusion polypeptides comprising the phage pIII coat protein amino acid sequence. However, it is not intended that the invention be limited to use of the pIII polypeptide sequence for the display of the polypeptide variants in a recombinant M13-derived phage display library.

As discussed previously, normalizing a recombinant M13-derived phage display library relies on subjecting every polypeptide variant in the library to the same growth disadvantage that would ordinarily only affect those variants comprising an unnatural amino acid residue. Accordingly, in a first aspect, the invention provides novel vector packaging systems, e.g., for the packaging of recombinant M13-derived phage, which allow the incorporation of at least one unnatural amino acid into a packaging or specificity polypeptide that is required for vector viability, e.g., a pIII protein, as into the target polypeptides, e.g., pIII-polypeptide variant fusion proteins, that comprise the library. An embodiment of a vector packaging system provided by the invention is illustrated in FIG. 1. The depicted embodiment includes vector nucleic acid (100), complementation nucleic acid (120), and orthogonal tRNA (O-tRNA) (130) that is charged with unnatural amino acid (135).

As shown in FIG. 1, the vector nucleic acid comprises or encodes packaging site (105), which allows the packaging of the vector nucleic acid into the interior of the vector during vector assembly. The vector nucleic acid can also include encoded target polypeptide (110) that can comprise a fusion protein, e.g., a fusion protein comprising a polypeptide variant. The encoded target polypeptide can optionally comprise at least one selector codon (115), such that the expressed target polypeptide optionally includes at least one unnatural amino acid residue.

As further shown in FIG. 1, complementation nucleic acid (120) of the vector packaging system encodes packaging or specificity polypeptide (125) that can optionally comprise a viral capsid or envelope protein, e.g., an M13 phage pIII protein, or other protein which is required for vector viability. The complementation nucleic acid comprises at least one selector codon (115), such that when expressed, the packaging or specificity polypeptide comprises at least one same unnatural amino acid as found in those target polypeptides comprising unnatural amino acids.

Accordingly, the vector packaging system, as depicted in FIG. 1, also includes orthogonal tRNA (O-tRNA) (130) charged with unnatural amino acid (135) which facilitates the incorporation of unnatural amino acids into the packaging or specificity polypeptide and, optionally, into the target polypeptide in response to encoded selector codons. The incorporation of the unnatural amino acid into the packaging or specificity polypeptide allows the normalization of the expression levels of all target polypeptides in a library of vectors, regardless of their amino acid compositions.

In a related aspect, the invention provides methods of using the vector packaging system to produce, e.g., a plurality of vectors, e.g., recombinant M13-derived phage, that comprise a phage display library. In general, the methods include expressing the vector nucleic acid to produce the target polypeptide, e.g., a pIII-polypeptide variant fusion protein, which can optionally include an unnatural amino acid and expressing the complementation nucleic acid to produce the packaging or specificity polypeptide, e.g., pIII, comprising an unnatural amino acid. The methods also include permitting a copy or a transcript of the vector nucleic acid to assemble with the target polypeptide and the packaging or specificity polypeptide comprising an unnatural amino acid residue, thereby producing a vector, e.g., a recombinant M13-derived phage. In this manner, all vectors produced by the provided methods are subject to the same growth disadvantage that would ordinarily only affect those vectors comprising target polypeptides that include unnatural amino acids.

Figure 2:
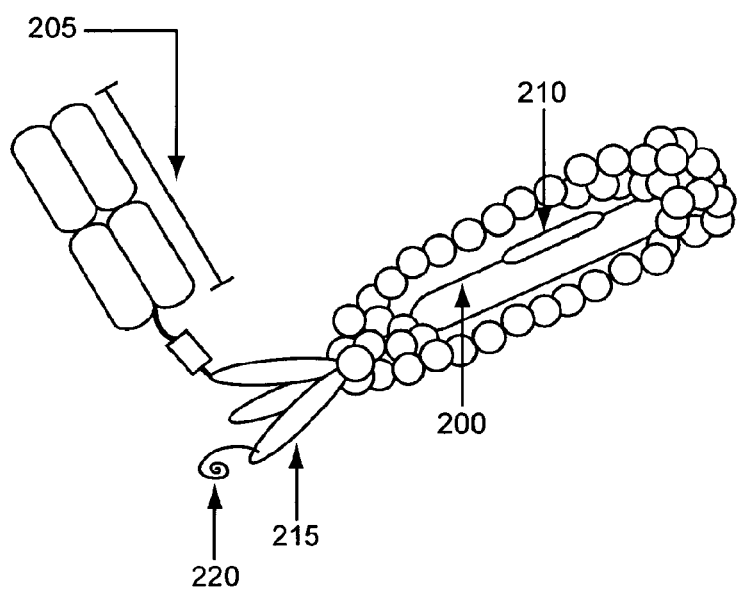
FIG. 2 illustrates an optional embodiment of a vector that can be produced by the method provided by the invention.
Figure 3:
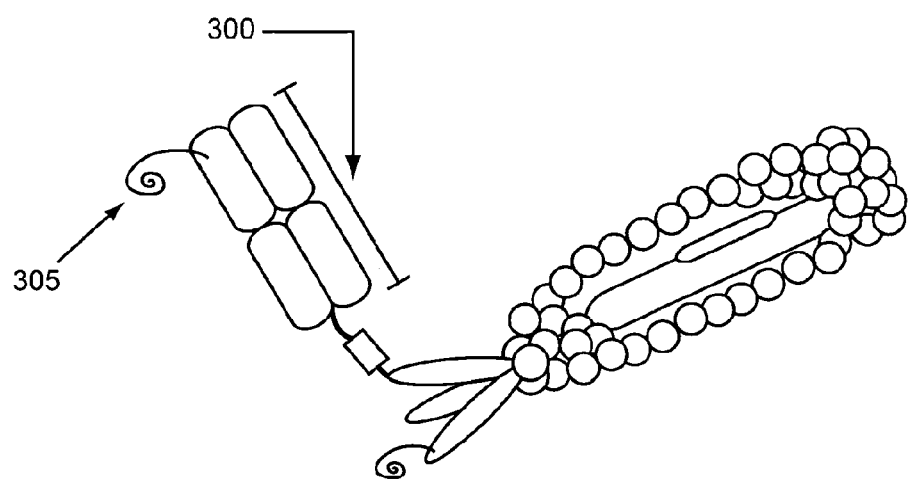
FIG. 3 illustrates a second optional embodiment of a vector that can be produced by the invention.

The invention also provides compositions for novel vectors that can be produced by the systems and methods described above. Depicted in FIGS. 2 and 3 are optional embodiments of vectors, e.g., phage, that comprise a normalized vector display library, e.g., a recombinant M13-derived phage display library. FIG. 2 illustrates a vector comprising packaged nucleic acid (200) that includes an encoded target polypeptide (210), and target polypeptide (205), e.g., a pIII-polypeptide variant fusion protein. In addition, the vector of FIG. 2 includes specificity polypeptide (215), e.g., pIII, which comprises at least one unnatural amino acid, residue (220). FIG. 3 depicts a vector that is identical to that in FIG. 2 in almost every respect, except that target polypeptide (300) of the vector in FIG. 3 comprises an unnatural amino acid residue (305).

Although the Example described below uses the M13KO7 phage system, it is not intended that the invention be limited to that particular system. The invention can similarly be used with other phage display systems, including T4 (Jiang, J., et al. (1997) "Display of a PorA peptide from *Neisseria meningitidis* on the bacteriophage T4 capsid surface." *Infect. Immun.* 65: 4770-4777), T7, (Danner, S., et al. (2001) "17 phage display: A novel genetic selection system for cloning RNA-binding proteins from cDNA libraries." *Proc. Natl. Acad. Sci. U.S.A.*, 98: 12954-19959), P4 (Lindqvist, B. H., et al. (1995) "Peptide presentation by bacteriophage P4." *FEMS Microbiol. Rev.,* 17: 33-39), and lambda phage (Kong, B., et al. (2006) "Display of aggregation-prone ligand binding domain of human PPAR gamma on surface of bacteriophage lambda." *Acta Pharmacol. Sin.* 27: 91-99). In addition this invention can also be used with eukaryotic viral display systems including baculovirus display systems (reviewed in Oker-Blom, C., et al. (2003) "Baculovirus display strategies: Emerging tools for eukaryotic libraries and gene delivery." *Brief Funct. Genomic Proteomic.* 2: 244-253, and Makela, A. R., et al. (2006) "Baculovirus display: a multifunctional technology for gene delivery and eukaryotic library development." *Adv. Virus Res.* 68: 91-112), adeno-associated virus display systems (Work, L. M., et al. (2006) "Vascular Bed-Targeted in Vivo Gene Delivery Using Tropism-Modified Adeno-associated Viruses." *Mol. Ther.* 13: 683-693) and newly emerging retroviral display systems (Urban, J. H., et al. (2005) "Selection of functional human antibodies from retroviral display libraries." *Nucleic Acids Res.* 33: e35).

Similarly, to demonstrate the present invention, the Example elaborated below demonstrates that the expression levels of ribosomally derived antibody fragments can be normalized in a recombinant M13-derived phage display library. It is not intended that the invention be limited to normalizing the expression levels of a library comprising variants of this model protein. The normalization of any phage-displayed polypeptide library of interest, including those enumerated in the present disclosure, is advantageous for screening any of a wide variety of proteins for use in therapeutic and research purposes.

Normalizing Multivalent Phage Display Libraries

The invention can also be adapted for use with multivalent phage display libraries, e.g., multivalent M13 phage display libraries. As discussed above, normalizing a recombinant M13-derived phage display library relies on removing the growth advantage that permits those variants comprising only natural amino acids to become over-represented. However, multivalent recombinant M13-derived phage do not comprise a packaging or specificity polypeptide, e.g., a wildtype pIII polypeptide. When multivalent M13 phage are packaged, the pIII-polypeptide variant fusion proteins are the sole source of pIII. Normalization of a multivalent phage display library can, therefore, be accomplished by, e.g., incorporating at least one same unnatural amino acid into the portion of the fusion protein common to all phage in the library, e.g., the portion comprising pIII, that can be incorporated into the variable portion of the fusion protein, e.g., the portion comprising the screenable polypeptide variant. In this manner, all polypeptide variants in multivalent phage display library will be subject to the same growth disadvantage that would ordinarily only affect those phage that display screenable polypeptide variants comprising unnatural amino acid residues.

Normalization of a multivalent phage display library can be achieved, e.g., by manipulating the growth conditions under which phage, e.g., multivalent recombinant M13-derived phage, are produced. For example, a normalized multivalent phage display library can be produced by transforming an appropriate *E. coli* strain carrying a plasmid encoding a six copies of an orthogonal tRNA (O-tRNA) and its cognate orthogonal aminoacyl-tRNA (O-RS) with a phagemid library, by infecting the strain with hyperphage, and by incubating the infected culture overnight at 30° C. in media containing an excess concentration, e.g., 1-15 mM, of unnatural amino acid, e.g., sulfotyrosine (15 mM), para-acetyl phenylalanine (6 mM), bipyridyl-alanine (1 mM). These growth conditions increase both the doubling time and the permeability of the *E. coli* strain, and allow the translational machinery, e.g., O-tRNAs charged with unnatural amino acid, to keep pace with the synthesis of target polypeptides. These growth conditions can produce a multivalent phage library, e.g., multivalent recombinant M13-derived phage library, with a normalization ratio of 5:1, as determined by comparing the expression of randomly selected phage displaying target polypeptides containing one or more selector unnatural amino acids to those phage displaying target polypeptides that contain no unnatural amino acids.

Orthogonal Translation System Components

In one aspect, the invention provides compositions, systems, and methods that produce vectors that include polypeptides, e.g., target polypeptides, e.g., pIII-polypeptide variant fusion proteins, and packaging or specificity polypeptides, e.g., pIII, that comprise unnatural amino acids. In another aspect, the invention provides compositions and methods for screening polypeptide libraries that include members that comprise unnatural amino acids. The incorporation of unnatural amino acids into these polypeptides is accomplished by adapting an orthogonal tRNA (O-tRNA) and an orthogonal aminoacyl-tRNA synthetase (O-RS) to recognize the desired unnatural amino acid and incorporate it into proteins in response to a selector codon (e.g., an amber nonsense codon, TAG). These orthogonal components do not cross-react with endogenous components of the translational machinery of the host cell, e.g., an *E. coli* cell, or with naturally occurring amino acids. The orthogonal components used in one Example herein include an O-RS, e.g., an O-RS derived from *Methanococcus jannaschii* tyrosyl tRNA-synthetase, and O-tRNA, e.g., the mutant tyrosyl tRNA$_{CUA}$ amber suppressor, which function as an orthogonal pair in host cells, e.g., *E. coli*.

As used herein, an unnatural amino acid refers to any amino acid, modified amino acid, or amino acid analogue other than selenocysteine and/or pyrolysine and the twenty genetically encoded alpha-amino acids. See, e.g., *Biochemistry by L. Stryer*, 3$^{rd}$ ed. 1988, Freeman and Company, New York, for structures of the twenty natural amino acids. Unnatural amino acids of the invention have side chain groups that distinguish them from the natural amino acids, although unnatural amino acids can be naturally occurring compounds other than the twenty proteinogenic alpha-amino acids. The unnatural amino acids finding use with the invention include an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

The invention optionally includes multiple O-tRNA/O-RS pairs. For example, the invention can further include an additional O-tRNA/O-RS pair where the second O-RS preferentially aminoacylates the second O-tRNA with a second unnatural amino acid, and the second O-tRNA recognizes a second selector codon. A number of different selector codons, e.g., a unique three base codon, a nonsense codon, such as a stop codon, e.g., an amber codon (UAG), or an opal codon (UGA), an unnatural codon, at least a four base codon, a rare codon, or the like, can be introduced into a gene, e.g., the coding sequence of a vector nucleic acid and/or a complementation nucleic acid. Multiple orthogonal tRNA/synthetase pairs can be used that allow the simultaneous site-specific incorporation of multiple unnatural amino acids, e.g., including at least one unnatural amino acid, using these different selector codons.

Although the orthogonal translation system components used with the invention can utilize cultured host cells to produce proteins having unnatural amino acids, it is not intended that the invention require an intact, viable host cell. For example, the orthogonal translation system components invention can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is within the scope of the invention.

Methods for producing and/or altering the specificity of O-tRNAs and/or O-RSs, unnatural amino acids, selector codons, and orthogonal translation systems that are suitable for making proteins that include one or more unnatural amino acids are generally described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. See also, Wang and Schultz "Expanding the Genetic Code," *Angewandte Chemie Int. Ed.*, 44(1):34-66 (2005); Deiters, et al. *Bioorganic & Medicinal Chemistry Letters* 15:1521-1524 (2005); Chin, et al. *J. Am. Chem. Soc.* 2002, 124, 9026-9027; and International Publication No. WO2006/034332, filed on Sep. 20, 2005, the contents of each of which are incorporated by reference in their entirety. Additional details are found in U.S. Pat. No. 7,045,337; U.S. Pat. No. 7,083,970; U.S. Pat. No. 7,238,510; U.S. Pat. No. 7,129,333; U.S. Pat. No. 7,262,040; U.S. Pat. No. 7,183,082; U.S. Pat. No. 7,199,222; and U.S. Pat. No. 7,217,809.

Proteins and Polypeptides of Interest

Methods for producing and screening normalized libraries of polypeptide variants that include members that comprise unnatural amino acids are a feature of this invention. The incorporation of an unnatural amino acid can be done to, e.g., modify polypeptide structure and/or function, e.g., to change size, acidity, nucleophilicity, hydrogen bonding, hydrophobicity, accessibility of protease target sites, incorporation of labels or reactive groups, etc. Polypeptides that include an unnatural amino acid can have enhanced or even entirely new catalytic or physical properties. For example, the following properties are optionally modified by inclusion of an unnatural amino acid into a polypeptide: toxicity, electrical properties, structural properties, spectroscopic properties, chemical and/or photochemical properties, catalytic ability, half-life, ability to react with other molecules, e.g., covalently or non-covalently, and the like. See, e.g., Dougherty, (2000) "Unnatural Amino Acids as Probes of Protein Structure and Function," *Current Opinion in Chemical Biology*, 4:645-652. Any of these can comprise a property or function of interest that can be identified by screening a normalized polypeptide library. However, the invention is not to be construed as being limited to the screening of only those properties listed above.

In some aspects, a variant in a polypeptide library can comprise at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. No attempt is made to identify the hundreds known polypeptide libraries, any member of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the interne.

Examples of therapeutic, diagnostic, and other screenable polypeptide variants comprising a library that can be modified to comprise one or more unnatural amino acid can be found, but not limited to, those in International Publications WO 2004/094593, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other polypeptide variants in a library that can be modified to comprise one or more unnatural amino acids include, but are not limited to, e.g., antibody variants, antibody fragment variants, Alpha-1 antitrypsin variants, Angiostatin variants, Antihemolytic factor variants, Apolipoprotein variants, Apoprotein variants, Atrial natriuretic factor variants, Atrial natriuretic polypeptide variants, Atrial peptide variants, C-X-C chemokine variants, T39765 variants, NAP-2 variants, ENA-78 variants, Gro-a variants, Gro-b variants, Gro-c variants, IP-10 variants, GCP-2 variants, NAP-4 variants, SDF-1 variants, PF4 variants, MIG variants, Calcitonin variants, c-kit ligand variants, cytokine variants, CC chemokine variants, Monocyte chemoattractant protein-1 variants, Monocyte chemoattractant protein-2 variants, Monocyte chemoattractant protein-3 variants, Monocyte inflammatory protein-1 alpha variants, Monocyte inflammatory protein-1 beta variants, RANTES variants, I309 variants, R83915 variants, R91733 variants, HCC1 variants, T58847 variants, D31065 variants, T64262 variants, CD40 variants, CD40 ligand variants, C-kit Ligand variants, Collagen variants, Colony stimulating factor (CSF) variants, Complement factor 5a variants, Complement inhibitor variants, Complement receptor 1 variants, cytokine variants, epithelial Neutrophil Activating Peptide-78 variants, GROα variants, MGSA variants, GROβ variants, GROγ variants, MIP1-α variants, MIP1-β variants, MCP-1 variants, Epidermal Growth Factor (EGF) variants, epithelial Neutrophil Activating Peptide variants, Erythropoietin (EPO) variants, Exfoliating toxin variants, Factor IX variants, Factor VII variants, Factor VIII variants, Factor X variants, Fibroblast Growth Factor (FGF) variants, Fibrinogen variants, Fibronectin variants, G-CSF variants, GM-CSF variants, Glucocerebrosidase variants, Gonadotropin variants, growth factor variants, growth factor receptor variants, Hedgehog protein variants, Hemoglobin variants, Hepatocyte Growth Factor (HGF) variants, Hirudin variants, Human serum albumin variants, ICAM-1 variants, ICAM-1 receptor variants, LFA-1 variants, LFA-1 receptor variants, Insulin variants, Insulin-like Growth Factor (IGF) variants, IGF-I variants, IGF-II variants, interferon variants, IFN-α variants, IFN-β variants, IFN-γ variants, interleukin variants, IL-1 variants, IL-2 variants, IL-3 variants, IL-4 variants, IL-5 variants, IL-6 variants, IL-7 variants, IL-8 variants, IL-9 variants, IL-10 variants, IL-11 variants, IL-12 variants, Keratinocyte Growth Factor (KGF) variants, Lactoferrin variants, leukemia inhibitory factor variants, Luciferase variants, Neurturin variants, Neutrophil inhibitory factor (NIF) variants, oncostatin M variants, Osteogenic protein variants, oncogene product variants, Parathyroid hormone variants, PD-ECSF variants, PDGF variants, peptide hormone variants, Human Growth Hormone variants, Pleiotropin variants, Protein A variants, Protein G variants, variants of Pyrogenic exotoxins A, B, or C, Relaxin variants, Renin variants, SCF/c-kit variants, Soluble complement receptor I variants, Soluble I-CAM 1 variants, Soluble interleukin receptor variants, Soluble TNF receptor variants, Somatomedin variants, Somatostatin variants, Somatotropin variants, Streptokinase variants, Superantigen variants, Staphylococcal enterotoxin variants, SEA variants, SEB variants, SEC1 variants, SEC2 variants, SEC3 variants, SED variants, SEE variants, steroid hormone receptor variants, Superoxide dismutase variants, Toxic shock syndrome toxin variants, Thymosin alpha 1 variants, Tissue plasminogen activator variants, tumor growth factor (TGF) variants, TGF-α variants, TGF-β variants, Tumor Necrosis Factor variants, Tumor Necrosis Factor alpha variants, Tumor necrosis factor beta variants, Tumor necrosis factor receptor (TNFR) variants, VLA-4 protein variants, VCAM-1 protein variants, Vascular Endothelial Growth Factor (VEGEF) variants, Urokinase variants, Mos variants, Ras variants, Raf variants, Met variants, p53 variants, Tat variants, Fos variants, Myc variants, Jun variants, Myb variants, Rel, estrogen receptor variants, progesterone receptor variants, testosterone receptor variants, aldosterone receptor variants, LDL receptor variants, variants of inflammatory molecules, variants of signal transduction molecules, variants of transcriptional activators, variants of a transcriptional suppressors, hyalurin variants, CD44 variants, and corticosterone variants.

A variety of purification/protein purification methods are well known in the art and can be applied to the purification and analysis of polypeptide variants identified based on a screen of a normalized polypeptide library. These techniques, and others that are necessary for the analysis of polypeptides, include those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag, et al. (1996) *Protein Methods,* 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Generating Mutational Derivatives of Polypeptides of Interest

Mutated derivatives of the proteins and polypeptides of interest described herein can be generated by standard methods, e.g., to produce a population of variants to comprise a normalized polypeptide library. Additional information on mutation formats is found in Sambrook and Ausubel, as well as in *PCR Protocols A Guide to Methods and Applications* (Innis, et al. eds) Academic Press Inc. San Diego, Calif. (1990) (Innis). The following publications and references provide additional detail on mutation formats: Arnold, et al. (1993) "Protein engineering for unusual environments." *Current Opinion in Biotechnology* 4:450-455; Bass, et al. (1988). "Mutant Trp repressors with new DNA-binding specificities." *Science* 242:240-245; Botstein & Shortle. (1985). "Strategies and applications of in vitro mutagenesis." *Science* 229:1193-1201; Carter (1985). "Improved oligonucleotide site-directed mutagenesis using M13 vectors." *Nucl. Acids Res.* 13: 4431-4443; Carter, et al. (1986). "Site-directed mutagenesis." *Biochem. J.* 237:1-7; Carter (1987). "Improved oligonucleotide-directed mutagenesis using M13 vectors." *Methods in Enzymol.* 154: 382-403; Dale, et al. (1996) "Oligonucleotide-directed random mutagenesis using the phosphorothioate method." *Methods Mol. Biol.* 57:369-374; Eghtedarzadeh & Henikoff, (1986) "Use of oligonucleotides to generate large deletions." *Nucl. Acids Res.* 14: 5115; Fritz, et al. (1985) "Oligonucleotide-directed construction of mutations: a gapped duplex DNA procedure without enzymatic reactions in vitro." *Nucl. Acids Res.* 16: 6987-6999; Grundström, et al. (1985) "Oligonucleotide-directed mutagenesis by microscale 'shot-gun' gene synthesis." *Nucl. Acids Res.* 13: 3305-3316; Kunkel, "The efficiency of oligonucleotide directed mutagenesis," in *Nucleic Acids & Molecular Biology* (Eckstein, F. and Lilley, D. M. J. eds., Springer Verlag, Berlin)) (1987); Kunkel, (1985) "Rapid and efficient site-specific mutagenesis without phenotypic selection." *Proc. Natl. Acad. Sci. U.S.A.* 82:488-492 (1985); Kunkel, et al. "Rapid and efficient site-specific mutagenesis without phenotypic selection," *Methods in Enzymol.* 154, 367-382 (1987); Kramer, et al. (1984) "The gapped duplex DNA approach to oligonucleotide-directed mutation construction." *Nucl. Acids Res.* 12: 9441-9456; Kramer & Fritz "Oligonucleotide-directed construction of mutations via gapped duplex DNA," *Methods in Enzymol.* 154:350-367 (1987); Kramer, et al. (1984) "Point Mismatch Repair." *Cell* 38:879-887; Kramer, et al. (1988) "Improved enzymatic in vitro reactions in the gapped duplex DNA approach to oligonucleotide-directed construction of mutations." *Nucl. Acids Res.* 16: 7207 (1988); Ling, et al. (1997) "Approaches to DNA mutagenesis: an overview." *Anal Biochem.* 254(2): 157-178; Lorimer and Pastan. (1995) *Nucleic Acids Res.* 23: 3067-8; Mandecki, (1986) "Oligonucleotide-directed double-strand break repair in plasmids of *Escherichia coli*: a method for site-specific mutagenesis." *Proc. Natl. Acad. Sci. U.S.A.* 83:7177-7181; Nakamaye & Eckstein, (1986) "Inhibition of restriction endonuclease Nci I cleavage by phosphorothioate groups and its application to oligonucleotide-directed mutagenesis." *Nucl. Acids Res.* 14: 9679-9698; Nambiar, et al. (1984) "Total synthesis and cloning of a gene coding for the ribonuclease S protein." *Science* 223: 1299-1301; Sakamar and Khorana, (1988) "Total synthesis and expression of a gene for the a-subunit of bovine rod outer segment guanine nucleotide-binding protein (transducin)." *Nucl. Acids Res.* 14: 6361-6372; Sayers, et al. (1988) "Y-T Exonucleases in phosphorothioate-based oligonucleotide-directed mutagenesis." *Nucl. Acids Res.* 16:791-802; Sayers, et al. (1988) "Strand specific cleavage of phosphorothioate-containing DNA by reaction with restriction endonucleases in the presence of ethidium bromide." *Nucl. Acids Res.* 16: 803-814; Sieber, et al. (2001) *Nature Biotechnology* 19:456-460; Smith, (1985) "In vitro mutagenesis." *Ann. Rev. Genet.* 19:423-462; *Methods in Enzymol.* 100: 468-500 (1983); *Methods in Enzymol.* 154: 329-350 (1987); Stemmer, *Nature* 370, 389-91 (1994); Taylor, et al. (1985) "The use of phosphorothioate-modified DNA in restriction enzyme reactions to prepare nicked DNA." *Nucl. Acids Res.* 13: 8749-8764; Taylor, et al. (1985) "The rapid generation of oligonucleotide-directed mutations at high frequency using phosphorothioate-modified DNA." *Nucl. Acids Res.* 13: 8765-8787; Wells, et al. (1986) "Importance of hydrogen-bond formation in stabilizing the transition state of subtilisin." *Phil. Trans. R. Soc. Lond. A* 317: 415-423; Wells, et al. (1985) "Cassette mutagenesis: an efficient method for generation of multiple mutations at defined sites." *Gene* 34:315-323; Zoller & Smith, (1982) "Oligonucleotide-directed mutagenesis using M13-derived vectors: an efficient and general procedure for the production of point mutations in any DNA fragment." *Nucleic Acids Res.* 10: 6487-6500; Zoller & Smith, (1983) "Oligonucleotide-directed mutagenesis of DNA fragments cloned into M13 vectors." *Methods in Enzymol.* 100: 468-500; and Zoller & Smith, (1987) "Oligonucleotide-directed mutagenesis: a simple method using two oligonucleotide primers and a single-stranded DNA template." *Methods in Enzymol.* 154: 329-350. The methods described in these references can be used to produce polypeptide variants via site-directed mutagenesis, via partially random mutagenesis, or via totally random mutagenesis. Additional details on many of the above methods can be found in *Methods in Enzymology* Volume 154, which also describes useful controls for trouble-shooting problems with various mutagenesis methods. Methods frequently used in mutagenesis for isolating, cloning, and amplifying nucleic acids are described more extensively below.

Providing and Expressing the Vector Nucleic Acid and/or Complementation Nucleic Acid of the Vector Packaging System A vector packaging system that produces vectors that can comprise a library of polypeptide variants that include unnatural amino acids is a feature of the invention. Also provided by the invention are methods for packaging vectors that include providing a vector nucleic acid and/or a complementation nucleic acid and expressing the vector nucleic acid and/or complementation nucleic acid to produce, respectively, a target polypeptide, e.g., a pIII fusion polypeptide, and a packaging or specificity polypeptide, e.g., pIII.

The vector nucleic acid and/or the complementation nucleic acid can be provided to the vector packaging system in a number of ways, including via transformation of a nucleic acid, e.g. a linear double-stranded DNA fragment, a circular DNA, or the like. In a prokaryotic system, this can include transforming a host cell, e.g., an E. coli cell, with a plasmid, phagemid, or the like, or via phage transduction or conjugation with an F' factor. In a eukaryotic system, the vector nucleic acid and/or the complementation nucleic acid can be provided to the vector packaging system via transformation of a plasmid, or by stable or transient transduction or the like. A purified vector nucleic acid and/or complementation nucleic acid can simply be added to an in vitro transcription/translation system.

Expressing the vector nucleic acid and/or complementation nucleic acid to produce their encoded polypeptides can be accomplished in a number of ways. However, the most widely used technique is to increase transcription levels of the mRNAs that encode the target polypeptide and/or packaging or specificity polypeptide. By cloning the sequences encoding the target polypeptide and/or packaging or specificity polypeptide downstream of an inducible promoter, the transcription levels of these genes will increase upon the addition of an appropriate inducer, e.g., IPTG, to a culture or in vitro transcription/translation system.

Procedures for isolating, cloning, and amplifying nucleic acids; and for providing nucleic acid constructs to and expressing nucleic acid constructs in cells and cell free systems are replete in the literature and can be used in the present invention to provide and express a vector nucleic acid and/or a complementation nucleic acid to a vector packaging system. Further details these techniques can be found in Berger and Kimmel, *Guide to Molecular Cloning Techniques, Methods in Enzymology* volume 152 Academic Press, Inc., San Diego, Calif. (Berger); Sambrook, et al. *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc (Rapley); *Current Protocols in Molecular Biology*, F. M. Ausubel, et al. eds., Current Protocols, a joint venture between Greene Publishing Associates, Inc. and John Wiley & Sons, Inc., (supplemented through 2007) ("Ausubel")); *PCR Protocols A Guide to Methods and Applications* (Innis, et al. eds) Academic Press Inc. San Diego, Calif. (1990) (Innis); Chen, et al. (ed) *PCR Cloning Protocols, Second Edition* (Methods in Molecular Biology, volume 192) Humana Press; in Viljoen, et al. (2005) *Molecular Diagnostic PCR Handbook* Springer; and Demidov and Broude (eds) (2005) *DNA Amplification: Current Technologies and* Applications. Horizon Bioscience, Wymondham, UK. Other useful references, e.g., for cell isolation and culture, e.g., for subsequent nucleic acid isolation, include Freshney (1994) *Culture of Animal Cells, a Manual of Basic Technique*, third edition, Wiley-Liss, New York and the references cited therein; Payne, et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A plethora of kits are also commercially available for the purification of plasmids or other relevant nucleic acids from cells, (see, e.g., EasyPrep™, FlexiPrep™, both from Pharmacia Biotech; StrataClean™, from Stratagene; QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Sambrook, Ausubel and Berger. In addition, essentially any nucleic acid can be custom or standard ordered from any of a variety of commercial sources, such as Operon Technologies Inc. (Huntsville, Ala.).

Kits

Kits are also a feature of the invention. For example, such kits can comprise components for using the composition herein, such as: a container to hold the kit components, instructional materials for practicing any method herein with the kit, or for producing a normalized polypeptide library, e.g., any of the libraries described herein, e.g., optionally produced by any of the vector packaging systems described herein. Kits for producing normalized polypeptide libraries wherein, for example, at least one polypeptide variant comprises at least one unnatural amino acid, can include a nucleic acid comprising a polynucleotide sequence encoding an O-tRNA, a nucleic acid comprising a polynucleotide encoding an O-RS, a suitable strain of prokaryotic, e.g., bacterial (e.g., E. coli) or eukaryotic (e.g., yeast or mammalian) host cells for expression of the O-tRNA/O-RS and expression of a normalized polypeptide library. Those of skill in the art will appreciate that the kits can optionally include any combination of systems, and compositions provided by the invention for use with any of the methods described herein.

EXAMPLES

The following examples are offered to illustrate, but not to limit the claimed invention.

Example 1

The Generation of Normalized Phage Display Libraries

This Example describes, e.g., compositions and methods for the generation of an example normalized phage display library. The approaches described herein can be adapted for use to screen any of a variety of classes of polypeptides in a variety of polypeptide library screening systems.

A phagemid that places the genes encoding an Fab comprising a germline $V_H3$-23/$D_H3$-10/$J_H4$-pIII fusion and a $V_\kappa A27$-$J_\kappa 1$ domain under the transcriptional control of the lac promoter was constructed. In addition, this phagemid included a TAG selector codon in CDR3. This phagemid was transformed into an E. coli strain carrying a plasmid encoding a six copies of an orthogonal tRNA (O-tRNA) capable of being charged with p-acetylphenylalanine and an orthogonal aminoacyl-tRNA (O-RS) capable of charging the O-tRNAs with p-acetylphenylalanine and into an E. coli strain carrying a plasmid encoding six copies of an O-tRNA capable of being charged with sulfotyrosine an O-RS capable of charging the encoded O-tRNAs with sulfotyrosine. The strains were grown in media supplemented with IPTG and the appropriate unnatural amino acid (UAA), e.g., p-acetylphenylalanine (keto) or sulfotyrosine (sulfo). Control cultures were grown in media supplemented only with IPTG.

Phages that display the Fab-pIII fusion protein were prepared by infecting the phagemid-transformed *E. coli* strains with an M13KO7-TAG helper phage, whose genome carries a mutant allele of a pIII gene that comprises the selector codon TAG. Since M13 phage assembly and infectivity relies on the availability of functional pIII, only those phage that incorporate a pIII derived from the M13KO7-TAG helper phage, e.g., a pIII comprising p-acetyl phenylalanine or sulfotyrosine, would be viable. Phage were produced by each of the four cultures for 18 hours and were then harvested.

When the supernatants from each of the four cultures was titered, it was found that the strains grown in media supplemented with the appropriate UAA produced 50-fold more phage than the strains grown in the absence of UAA. It is notable that a comparable titer of phage could be produced in a non-UAA system in less than 12 hours.

Figure 4:
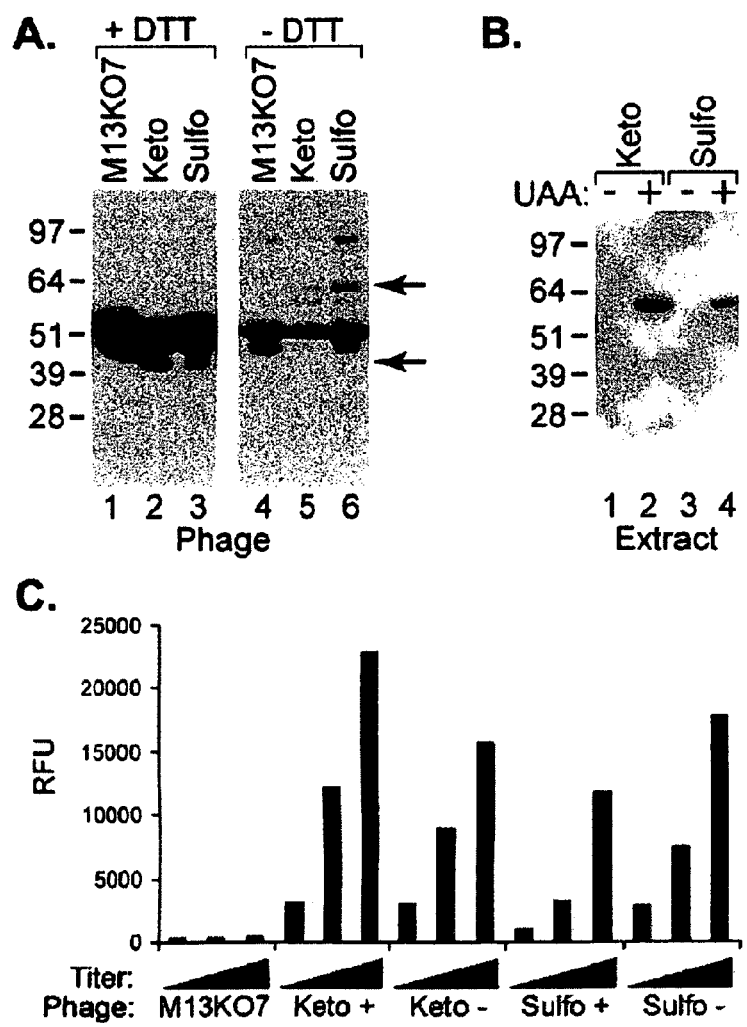
FIG. 4 depicts results from experiments that were performed to determine whether phage display Fab on their outer surfaces.

To determine whether the Fab encoded by the phagemid was displayed on the surface of the harvested phage, Western blots anti-pIII antibodies were performed. The results of the Western blots are shown in FIG. 4A. Since the Fab-pIII fusion protein contains only the carboxy-terminal portion of pIII, the fusion protein is expected, under reducing conditions, to migrate faster than wildtype (WT) pIII. Under reducing conditions, a new band corresponding to Fab-pIII was detected below WT pIII. This band was not detected in extracts derived from helper phage, indicating that this band's specificity to constructs expressing the Fab-pIII fusion (see, e.g., FIG. 4*a*, compare lane 1 to lanes 2 and 3).

Under non-reducing conditions, a slowly migrating band with an approximate molecular weight of 60 kDa was detected, but only in phagemid-containing preparations (see, e.g., FIG. 4*a*, lanes 5 and 6). The ~60 kDa bands in these lanes were also found to react with anti-kappa antibody, indicating the presence of fully assembled Fab on the surfaces of the harvested phage particles. The same ~60 kDa protein was detected in extracts derived from *E. coli* cells that express the Fab-pIII fusion protein that were not infected with the helper phage (see, e.g., FIG. 4*b*, lanes 2 and 4), indicating that the ~60 kDa pIII-reactive band was not derived from the helper phage. In addition, this band also reacted with anti-kappa antibodies. It is estimated that 1 in every 100 phage particles displays one Fab-pIII fusion.

Phage particles harvested from cultures grown in the absence of UAA could be detected and titered following concentration in an amicon 100 kDa MWCO filter. To determine whether these phages display Fab on their surfaces, e.g., by the incorporation of tyrosine, the natural amino acid from which the O-RS was evolved, or whether these phages are "bald", e.g., they do not display any Fab at all, equal titers of phages harvested from each of the four cultures, e.g., keto RS cells grown in media+p-acetylphenylalanine, keto RS cells grown in media−p-acetylphenylalanine, sulfo RS cells grown in media+sulfotyrosine, sulfo RS cells grown in media−sulfotyrosine, were analyzed via sandwich ELISA. Microtiter plates were coated with an anti-kappa antibody, blocked, and bound to increasing titers of phage. Antibody that reacts with the phage coat protein pVIII was used to detect the amount of phage bound to the microtiter plates. Specific detection of kappa-bound phage was found in all experimental groups, except for the negative control helper phage (see, e.g., FIG. 4C). Similarly, in a direct ELISA, a protein G-HRP reagent could detect Fab on all phage except the helper phage. Therefore, Fab appears to be presented on phage in the absence of UAA, albeit at a yield of 1/20 of that obtained when phage are grown in the presence of UAA. The mechanism of display in phage grown in the absence of UAA is likely to be incorporation of tyrosine by the O-RS. This result indicates that it will be useful to confirm that any library-selected Fabs require UAA for their phenotype.

Having determined that Fab are displayed appropriately on phage particles, the phagemid described above was then used to generate libraries of phagemids encoding Fab variants that comprise the selector codon in CDR3. Three different libraries were produced using a modified overlap extension PCR protocol. In the first, i.e., Germline/TAG-CDR3, tyrosine codons in the Fab gene sequences were mutated to TAG to produce a population of phagemid variants that each comprised one unnatural amino acid at a position into which a tyrosine residue would ordinarily be incorporated. Additional NNK codons were added between $V_H$-$D_H$ and $D_H$-$J_H$ to a subset of the Fab coding sequences in this library to mimic the N-region addition that occurs during V(D)J recombination in vivo. The second library, i.e., NNK/TAG-CDR3, provided Fab gene variants encoding three different lengths of CDR3, with a TAG codon incorporated at a different amino acid position in each library member. The third library, i.e., NNK-CDR3 provided Fab gene variants in which any of the 21 amino acids could incorporated at any position.

The oligonucleotides (SEQ ID NOs: 1-48) designed to generate each library are shown in FIG. 5. These sequences were derived from human DH1 though DH3 families, and designed to degenerately encode each entire family. Added codons at the V-D and D-J junctions are underlined. On the sequences near the CDR3 are shown. The actual oligonucleotides extend approximately 10 bases on both the 5' and 3' ends. For degenerate codons, N=A, T, C, G; B=C, G, T; D=A, G, T; H=A, C, T; V=A, C, G; R=A, G; Y=C, T; K=G, T; M=A, C; S=G, C, W=A, T.

At least 20 clones from each "naïve" library were sequenced to confirm that there existed no biases regarding codon representation among the variants and to confirm that the variants encoded full-length Fab fragments. The approximate theoretical diversity for each of the three libraries was $10^7$-$10^8$. Actual independent ligation events for each library were >$10^9$, based on transformation efficiency, indicating complete coverage of diversity by each library.

Each library of phagemid variants was transformed into an appropriate *E. coli* strain carrying a plasmid encoding six copies of the O-tRNA and the O-RS specific for bipyridyl alanine. The transformed strains were grown in media supplemented with bipyridyl alanine, an unnatural amino acid that is expected to possess efficient metal chelating properties.

Phages that display the Fab-pIII fusion proteins were prepared by infecting the phagemid-transformed *E. coli* strains with an M13KO7-TAG helper phage, which, as described above, carries a mutant allele of a pIII gene that comprises the selector codon TAG. Phage were produced by each *E. coli* strain for 18 hours and where then harvested.

To determine whether it is possible to isolate phage-displayed Fabs comprising bipyridyl alanine from the libraries, a previously described model system for the selection of metal binding antibodies comprising only natural amino acids was used (Trisler, et al. (2007) "A Metalloantibody That Irreversibly Binds a Protein Antigen." *Journal of Biological Chemistry*. 282: 26344-26353). The phage produced by the *E. coli* transformed with the second and third phagemid libraries were incubated with a nickel resin (Qiagen) for 5 minutes and then washed with five column volumes of TBST (20 mM Tris pH=8, 150 mM NaCl, 0.025% tween-20), then eluted in one column volume (0.2 ml) step gradients of imidazole at 10 mM, 50 mM, 100 mM, 150 mM, 200 mM, 300 mM, and 500 mM. The eluted phage were used to infect *E. coli*, which were then plated on agar media supplemented with ampicillin. Colonies were picked and cultured, and each phagemid DNA harvested from each colony was sequenced.

Figure 6:
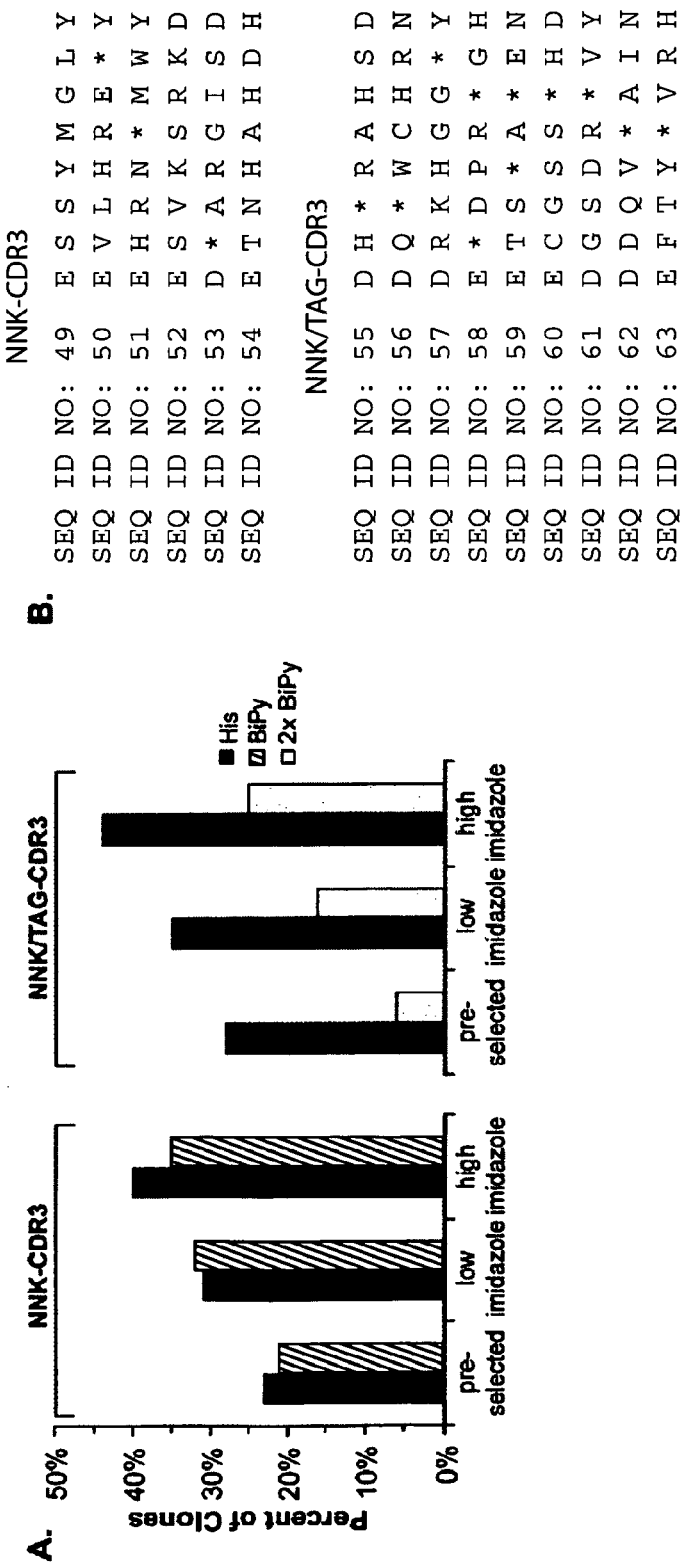
FIG. 6 depicts the results of a screen to isolate Fabs that bind nickel resin. The amino acid sequences of multiple clones were determined (SEQ ID NOs: 49-63), and the frequency of TAG was determined compared to the preselected library.

Several colonies from each imidazole elution fraction were sequenced. Even after only one round of selection, several Fab variants comprising at least one bipyridyl alanine residue, e.g., encoding at least one TAG codon, in CDR3 were isolated from each library. Multiple clones (SEQ ID NOs: 49-63) from each library were sequenced, and the frequency of TAG was determined and compared to the preselected library (see, e.g., FIG. 6). Since all members of the NNK-TAG-CDR3 library contain a TAG, the frequency of clones with two TAGs was enumerated. The frequency of TAG codons in CDR3 increased with increasingly stringent imidazole elutions (see, e.g., FIG. 6).

Histidine is a known metal binding amino acid that is naturally incorporated into polypeptides. As an internal positive control, the frequency of hisitidine codons in CD3 was also monitored, and it was found that the number of histidine codons in CDR3 of isolated clones (SEQ ID NOs: 49-63) also increased with increasingly stringent imidazole elutions (see, e.g., FIG. 6b; UAA positions are indicated by an asterisk).

Example 2

The Generation of Normalized Multivalent Phage Display Libraries

This Example describes, e.g., compositions and methods for the generation of an example normalized multivalent phage display library. The approaches described herein can also be adapted for use to screen any of a variety of classes of polypeptides in a variety of polypeptide library screening systems. Further details regarding these approaches are elaborated in Liu, et al. (2008) "Protein Evolution with and Expanded Genetic Code." *Proc Natl Acad Sci USA*, In press, which is incorporated herein by reference.

A previously described phagemid (see, e.g., Rondot, et al. (2001) "A helper phage to improve single-chain antibody presentation in phage display." *Nature Biotech.* 19: 75-78) was constructed to encode an scFv comprising the selector codon TAG. This phagemid was transformed into an *E. coli* strain carrying a plasmid that encodes six copies of an orthogonal tRNA (O-tRNA) capable of being charged with an unnatural amino acid, e.g., para-acetylphenylalanine, bipyridyl-alanine, sulfotyrosine, or 4-boronophenylalanine, and an orthogonal aminoacyl-tRNA (O-RS) capable of charging the O-tRNAs with an unnatural amino acid, e.g., para-acetylphenylalanine, bipyridyl-alanine, sulfotyrosine, or 4-boronophenylalanine. Further details regarding the genetic incorporation of boronic amino acids are described in Brustad, et al. (2008) "A Genetically Encoded Boronate-Containing Amino Acid." *Agnew Chem* 120: 8344-8347, which is incorporated herein by reference. Experiments were performed (as described in Methods) to characterize phage production in media supplemented with unnatural amino acid, e.g., para-acetylphenylalanine, bipyridyl-alanine, sulfotyrosine, or 4-boronophenylalanine, vs. media to which unnatural amino acid was not added. Phage were harvested and titered (as described hereinbelow), and it was found that cultures grown in media supplemented with unnatural amino acid produced 300-fold more phage than cultures grown in the absence of UAA.

A phagemid library of germline antibody variants was produced wherein the CDR3 loop of each variant carries an insertion comprising six random NNK codons. This phagemid library was used to transform an appropriate *E. coli* strain carrying a plasmid encoding six copies of the O-tRNA and the O-RS specific for the unnatural amino acid sulfotyrosine, and the transformed strain was grown in media supplemented with 15 mM sulfotyrosine. Multivalent phage that display the antibody variant-pIII fusion proteins were prepared by infecting the phagemid-transformed *E. coli* strains with a hyperphage in which the gene encoding pIII has been deleted (see, e.g., Rondot, et al. (2001) "A helper phage to improve single-chain antibody presentation in phage display." *Nature Biotech.* 19: 75-78). Phage were produced by the *E. coli* strain for 18 hours and where then harvested. Western blots were performed as described in Example 1 and confirmed that the antibody variants are displayed appropriately on phage particles.

The harvested phage were then screened via ELISA to identify and isolate those phage that display an antibody variant capable of binding gp120, an HIV envelope glycoprotein that binds sulfated receptors. fThe antibody variants that were isolated during this assay were found to be enriched for TAG codons, indicating that sulfated antibody variants, e.g., antibody variants comprising the unnatural amino acid sulfotyrosine, were preferentially selected in the assay. Further details are elaborated below.

Protein Evolution with an Expanded Genetic Code

We have devised a phage display system in which an expanded genetic code is available to protein evolution. This allows for the evolution of protein sequences containing unnatural ammo acids should such sequences functionally outperform ones containing only the 20 canonical amino acids. We have optimized this system for functional evolution with several unnatural amino acids and provide a demonstration of its utility through the selection of anti-gp120 antibodies. One such antibody, selected from a naïve germline scFv antibody library in which six residues in $V_H$CDR3 were randomized, contains sulfotyrosine and binds gp120 with higher affinity than a known sulfated antibody isolated from human serum. An expanded "synthetic" genetic code can confer an advantage in the directed evolution of proteins with specific properties.

With few exceptions, the genetic codes of organisms specify only the 20 canonical amino acids for protein synthesis. Yet it is quite possible that additional amino acids and the chemical functionalities represented therein would be evolutionarily advantageous, especially since nature's choice of 20 could have been arbitrarily fixed at the point of transition between communal and Darwinian evolution paradigms and subsequently sustained by the code's inertia (1). Furthermore, in the limited scope of laboratory directed evolution, which concerns only one or few specific functions over a short time rather than general organismal fitness over thousands of years, one can easily envision a selective advantage of additional amino acids. Recent developments in our lab allow us to explore this possibility. Specifically, orthogonal tRNA/ aminoacyl-tRNA synthetase (aaRS) pairs capable of incorporating various unnatural amino acids into proteins in response to unique nonsense and frameshift codons have been added to the translational machinery of *E. coli* (2). These *E. coli* (X-*E. coli*) can now be used for evolution of protein function wherein 21 building blocks rather than the common 20 are available.

Several unnatural amino acids were initially chosen, on the basis of their unique chemistries, for use in our system. For example, X-*E. coli* genetically encoding the bidentate metal-chelating amino acid bipyridyl-alanine (3, U.S. patent application Ser. No. 11/665,083, entitled "Orthogonal translation components for the in vivo incorporation of unnatural amino acids, by Schultz, et al., filed Apr. 10, 2007; see also WO/2006/110182, filed Oct. 26, 2005) are well suited for the evolution of redox and hydrolytic catalysts since metal ion binding would not require preorganized primary and secondary ligand shells. Similarly, X-*E. coli* encoding the reactive 4-borono-phenylalanine (4, U.S. Provisional Patent Applications Nos. 61/137,689, filed Aug. 1, 2008; and 61/189,739, filed Aug. 22, 2008) are well-suited for evolution of antibodies specific to glycoproteins or serine proteases since the boronate group can form high-affinity complexes with diols or reactive serine residues. In addition, X-*E. coli* genetically encoding otherwise post-translationally modified amino acids such as sulfotyrosine (5, U.S. patent application Ser. No. 11/903,499, entitled "Genetically programmed expression of selectively sulfated proteins in Eubacteria," by Liu, et al., filed Sep. 20, 2007; see also WO/2008/036392, filed Sep. 20, 2007) can be used for evolution of properties that exploit the unique chemical characteristics of the given post-translational modification, but without any of the host organism and sequence constraints normally limiting such modifications (6). And finally, X-*E. coli* using keto amino acids such as para-acetylphenylalanine can be advantageous in the evolution of catalysts for reactions involving iminiumuin intermediates (e.g. addition, isomerization, or decarboxylation reactions) (7). With this framework in mind, we have developed a system for protein evolution in which unnatural amino acids encoded by X-*E. coli* are included in phage-displayed libraries. This system is designed such that sequences with unnatural amino acids can be selected based on function from populations containing both sequences with unnatural amino acids and sequences with only the 20 common amino acids. We then used this system for the evolution of anti-gp120 antibodies and find that specific sequences containing sulfotyrosine emerge as winners over all other sequences represented in the population, including those that contain only canonical amino acids. These studies demonstrate, for the first time, that an expanded genetic code can confer a selective advantage through the functional contribution of an unnatural amino acid.

Proteins Containing Unnatural Amino Acids are Correctly Displayed on Phage Coat in a Phagemid Format Phage display can be a versatile platform for the directed evolution of a wide variety of protein functions (8-13). Under the constraints of phage display evolution, functional evolution entails two basic criteria. First, the phage produced by *E. coli* must properly and effectively display the protein undergoing evolution; and second, selective advantage (e.g. enrichment) should be as closely linked to functional performance as possible. This requires the mitigation of any systematic biases against certain classes of sequences that are not based on function. Although unnatural amino acids have been displayed on wild-type M13 phage as single peptides (14), such a system was not amenable to directed evolution experiments under these constraints. We therefore turned to phagemid display, specifically multivalent hyperphage phagemid display (15, 16), which we felt would fulfill these two criteria for both the canonical and unnatural amino acids.

Figure 7F:
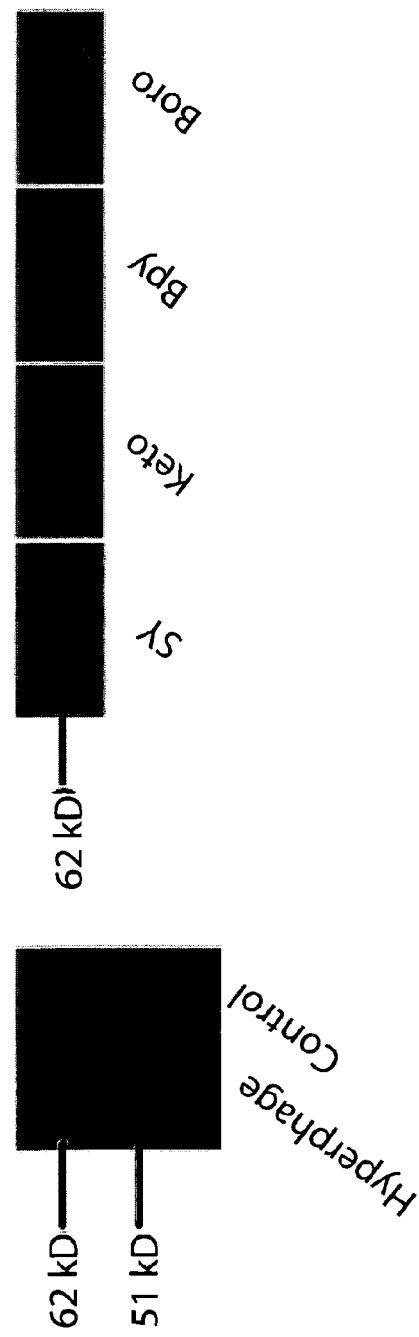

To test whether a phagemid-encoded protein sequence containing an unnatural amino acid can be displayed on the surface of phage, pIII was fused to the C-terminal end of an scFv derived from the common human $V_H3$-23 and $V_LA27$ germline sequences. An amber codon was substituted at position 111 in the $V_H$CDR3 loop, and this construct was inserted into the pSEX phagemid to create pSEX-GermTAG. This plasmid was subsequently transformed into four different X-*E. coli*, one encoding sulfotyrosine (SY-X-*E. coli*) (5), one encoding para-acetylphenylalanine (Keto-X-*E. coli*) (7), one encoding bipyridyl-alanine (Bpy-X-*E. coli*) (3), and one encoding 4-borono-phenylalanine (Boro-X-*E. coli*) (4), all in response to the amber codon. Since the only source of pIII for phage packing is phagemid-encoded antibody-pIII fusion (16), phage should be produced only if the amber codon upstream of pIII is suppressed. Hyperphage was then used to generate the respective phage-displayed scFvs from these clones. Phage yield was determined in the presence and absence of the respective unnatural amino acid (FIG. 7*a-d*). The addition of the corresponding unnatural amino acid to the growth media resulted in phage yields over 1000-fold greater than yields in the absence (FIG. 7*e*), confirming that protein sequences containing unnatural amino acids can be displayed in this system. SDS-PAGE and western blot analysis of precipitated whole phage was used to confirm that the full scFv-pIII fusion was effectively presented (FIG. 7*f*).

Phage Yield Bias Against Sequences Containing Unnatural Amino Acids can be Minimized to Allow Directed Evolution Although the display of sequences containing unnatural amino acids on phage coat was successful, early experiments gave low overall phage yields from pSEX-GermTAG when compared to display of sequences from pSEX-GermTAT in which the amber codon was replaced by one specifying tyrosine (See Table 1a below). This was expected since the suppression efficiency of unnatural amino acids using engineered aaRS/tRNA pairs is lower than suppression with the common amino acids using endogenous machinery. Yet in order to evolve proteins with unnatural amino acids, one must be able to compete sequences containing unnatural amino acids against those containing only the canonical 20 amino acids over multiple rounds of selection, a scenario that does not tolerate large systematic expression biases against sequences containing unnatural amino acids. Therefore, we optimized growth conditions (phage production temperature, expression time, and plasmid encoding tRNA/aaRS pairs) and unnatural amino acid concentrations for several X-*E. coli* (Table 1a) such that yield of phage displaying unnatural amino acids was similar to yield of phage displaying natural sequences. We suspected that optimization could be achieved through growth conditions and amino acid concentrations alone since it requires only an increase in the rate of full-length fusion-pIII protein expression relative to the rate of the other steps in the phage packaging and assembly process; it does not entail increasing amber codon suppression efficiency. As shown in Table 1b (below), under optimized conditions, the yield/expression bias in favor of sequences containing only the common amino acids was <3-fold for the four X-*E. coli* tested. This means that if a sequence containing an unnatural amino acid functionally outperforms the most competitive sequence containing only natural amino acids by at least ~3-fold, it will be enriched despite bias against.

Table 1a below shows the conditions that were tested to optimize phage yield based on a model scFv. "Strain used" refers to the strain containing the unnatural amino acid and synthetase specific to that strain. Unnatural amino acid was added directly to the media at the listed concentrations during phage expression. The yield ratio was taken as the titer of phage expressed from pSEX-GermTAG (unnatural phage) divided by the titer of phage expressed from pSEX-GermTAT (natural phage). We hypothesize that our optimization procedure increased the total production of unnatural amino acid containing pIII-fusion protein and at the same time decreased the rate of another step of the phage production process such as assembly or packaging.

TABLE 1a

| Synthetase plasmid backbone | Temperature (degrees ° C.) | Phage growth time (hr) | Strain used | Unnatural amino acid concentration (mM) | (Unnatural phage yield)/(Natural phage yield)* |
|---|---|---|---|---|---|
| pSup | 37 | 12 | SY-X-*E. coli* | 5 | 0.02 |
| pSup | 37 | 12 | Keto-X-*E. coli* | 5 | 0.02 |
| pCDF | 37 | 12 | SY-X-*E. coli* | 5 | 0.08 |
| pCDF | 37 | 12 | Keto-X-*E. coli* | 5 | 0.09 |
| pCDF | 30 | 12 | Keto-X-*E. coli* | 5 | 0.18 |
| pCDF | 30 | 18 | Keto-X-*E. coli* | 5 | 0.25 |
| pCDF | 30 | 18 | SY-X-*E. coli* | 10 | 0.24 |
| pCDF | 30 | 18 | Keto-X-*E. coli* | 8 | 0.4 ± 0.031 |
| pCDF | 30 | 18 | SY-X-*E. coli* | 15 | 0.33 ± 0.057 |
| pCDF | 30 | 18 | Bpy-X-*E. coli* | 1.5 | 0.34 ± 0.072 |
| pCDF | 30 | 18 | Boro-X-*E. coli* | 6.5 | 0.90 ± 0.149** |

*For the final set of conditions, ratios were determined in triplicate where cultures were split into three sets of two samples (natural and unnatural phage) for phage expression. (±standard deviations reported.)
**The addition of NaOH required to solubilize 4-borono-phenylalanine resulted in lower growth. Therefore, determination of natural phage yield was done in the presence of NaOH and 4-borono-phenylalanine in this case. In all other cases, addition of the unnatural amino acid did not noticeably affect natural phage yield.

Table 1b shows the final optimized conditions and yield bias in favor of phage expressing the test scFv-pIII with a TAT codon in place of the TAG codon (natural phage).

TABLE 1b

| Strain | Synthetase plasmid backbone | Temperature (degrees ° C.) | Phage growth time (hr) | Unnatural amino acid concentration (mM) | Bias for natural phage |
|---|---|---|---|---|---|
| SY-X-*E. coli* | pCDF | 30 | 18 | 15 | 3x |
| Keto-X-*E. coli* | pCDF | 30 | 18 | 8 | 2.5x |
| Bpy-X-*E. coli* | pCDF | 30 | 18 | 1.5 | 2.9x |
| Boro-X-*E. coli* | pCDF | 30 | 18 | 6 | 1.5x |

Table 1c shows the number of clones containing a TAG codon after phage expression from the pSEX-GermNNK library in Keto-X-*E. coli*, SY-X-*E. coli*, Bpy-X-*E. coli*, or Boro-X-*E. coli* (n=50 or 100) and associated $\chi^2$ values to show that bias on the population level is typified by bias of individual clone. Before phage expression entry refers to the clones found in the original library prior to phage production.

TABLE 1c

| Strain | # of clones sequenced (n) | # containing at least 1 TAG (measured) | # containing at least 1 TAG (expected from bias) | Expected standard deviation from binomial distribution* | $\chi^2$ (using binomial distribution standard deviation)** |
|---|---|---|---|---|---|
| SY-X-*E. coli* | 100 | 7 | 5.71 | 2.32 | 0.62 |
| Keto-X-*E. coli* | 100 | 10 | 6.92 | 1.79 | 2.94 |
| Bpy-X-*E. coli* | 100 | 7 | 5.88 | 1.66 | 1.62 |
| Boro-X-*E. coli* | 100 | 16 | 15.56 | 3.63 | 0.03 |
| Before phage expression | 50 | 9 | 8.65 | 2.67 | 0.03 |

Figure 8:
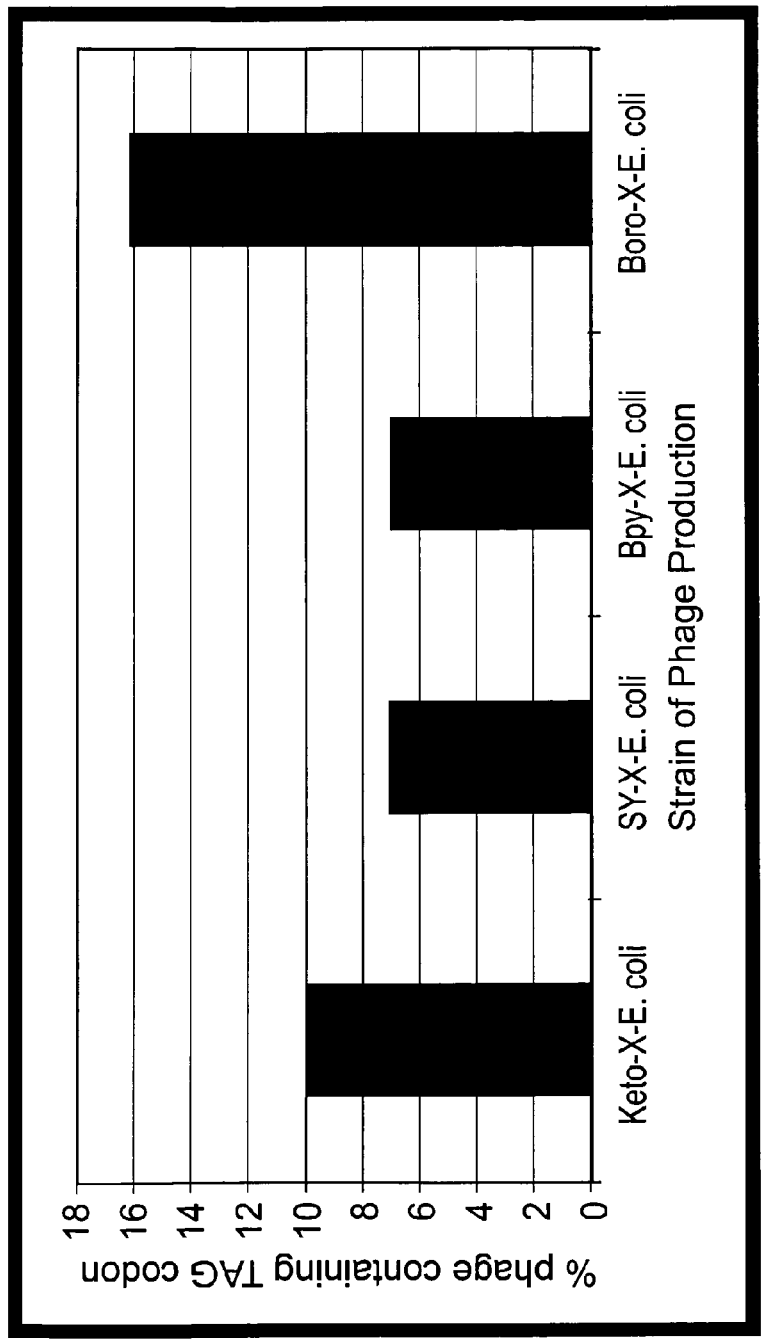
FIG. 8 depicts the results of experiments performed to determine the percent of phage clones containing a TAG codon after phage expression from the pSEX-GermNNK library in Keto-X-*E. coli*, SY-X-*E. coli*, Bpy-X-*E. coli*, or Boro X-*E. coli*.

*$[np(1-p)]^{(1/2)}$ where n is # of clones sequenced and p = (unnatural phage yield)/(natural phage yield) ×0.173
**values under 3.84 (corresponding to 5% probability) are accepted as consistent with the expected bias determined on an individual clone These optimized conditions were then tested with a phagemid library of antibodies in order to ensure that biases determined for the individual clones extend to the population level. Six consecutive residues completely randomized by site-saturation mutagenesis using NNK were therefore placed into the $V_H$ 3-23 CDR3 loop replacing residues 101-106, by overlap PCR using a randomized primer. This was subsequently cloned into the pSEX-GermTAT vector to create library pSEX-GermNNK (see Methods). After transformation into Top10 F' a maximal complexity of $5 \times 10^8$ was experimentally achieved, and sequencing revealed that approximately 18% of clones (n=50, 17.3% expected by the binomial distribution using the 1/32 probability of finding TAG at any NNK randomized site) contained the amber codon before phage production. After phage production in SY-X-*E. coli*, Keto-X-*E. coli*, Bpy-X-*E. coli*, or Boro-X-*E. coli*, the resulting phage population had between 7 and 16 percent of clones containing the amber codon as revealed by sequencing (n=100). On a population level, this represents a 1.1- to 2.5- fold expression bias in favor of sequences containing only the canonical amino acids, which is consistent with the bias typified by individual clones (FIG. 8). FIG. 8 shows the percent phage clones containing one or more TAG codons after phage expression from the pSEX-GermNNK library in Keto-X-*E. coli*, SY-X-*E. coli*, Bpy-X-*E. coli*, or Boro-X-*E. coli* (n=100). Expected value is 17.3%; deviation represents a bias in favor of sequences containing only the 20 canonical amino acids. Phage were produced under optimized conditions. $\chi^2$ tests suggest that these values are consistent with the bias typified by individual clones (Table 1c). This mild expression bias should be easily overcome by functional performance.

A Known Sulfotyrosine-Containing Anti-Gp120 Antibody can be Selected Out from a Doped Randomized Library Using SY-X-*E. Coli*

It is known that HIV infection requires gp120 binding to the CCR5 coreceptor, that sulfation of CCR5 is obligatory for this interaction to be productive, and that neutralizing anti-gp120 sulfated human antibodies isolated from serum exploit this feature (17, 18). In fact, the recent crystal structure of one such antibody, 412d, bound to gp120 reveals that its two sulfotyrosines contribute to approximately 20% of the total buried surface with one of the two accounting for almost 100 $Å^2$ (19). We reasoned, therefore, that high affinity anti-gp120 antibodies could be evolved in SY-X-*E. coli* since sulfated tyrosine, otherwise a result of post-translational modification in complex eukaryotes, could be incorporated into any sequence as an unnatural amino acid in *E. coli*.

We first conducted a test evolution experiment to see whether antibody 412d containing the two sulfotyrosines (residues 100 and 100c) could be selected from a randomized library based on affinity for gp120. To adapt 412d for phage, the scFv 412d-2SY with two amber codons introduced at the two sites of human 412d tyrosine sulfation (residues 104 and 107 of the scFv form) was cloned into the pSEX backbone to create pSEX-412d2TAG. 412d-2SY was then displayed on phage using SY-X-*E. coli*. To generate a 412d library, the 412d scFv-pIII coding sequence was randomized by site-saturation mutagenesis with NNK at residues in close proximity to the sulfotyrosines-Pro101, Asn105, Ala108, Pro109, Gly112, Met113—as well as the two locations where sulfation occurs—residues 104 and 107 (see Methods) (20). The resulting phagemid library (experimental maximal complexity of $2\times10^8$) was transformed into SY-X-*E. coli* from which phage were then produced. This phage population was spiked with phage displaying 412d-2SY at a ratio of one 412d-2SY phage to 2000 library phage and panned against gp120 immobilized on a microtiter plate. After four rounds of selection in which phage amplification was conducted in SY-X-*E. coli* after each round, the population converged onto one sequence, 412d-2SY (SEQ ID NO: 64), demonstrating that evolution for gp120 binding in SY-X-*E. coli* can yield a sequence containing unnatural amino acids. In fact, the population after the third round (nearly complete convergence occurred after the fourth) also had sulfotyrosine-containing sequences that originated from library rather than spiked phage (Table 2 below). This shows that new sequences containing an unnatural amino acid, e.g., SEQ ID NOs: 65-69, and not just 412d-2SY (SEQ ID NO: 64), are also evolved to bind gp120. Table 2 shows a list of sequences (SEQ ID NOs: 65-69) selected from a 412d-based library doped with 412d-2SY (SEQ ID NO: 64). Underlined are the positions that were randomized with NNK.

TABLE 2

| Sequence of doped 412d-2SY |
|---|
| . . . YP<u>ND*ND*A</u>PEEGM . . . (SEQ ID NO: 64) |

| Selected sequences |
|---|
| . . . YTNDLND*GEEEHG . . . (SEQ ID NO: 65) |
| . . . YNNDDNDLRLGE*S . . . (SEQ ID NO: 66) |
| . . . YDNDNDDGTAEE*Y . . . (SEQ ID NO: 67) |
| . . . YPND*ND*APEEGS . . . (SEQ ID NO: 68) |
| . . . YPND*ND*APEEGM . . . (SEQ ID NO: 69) (~75% of population) |

Figure 9:
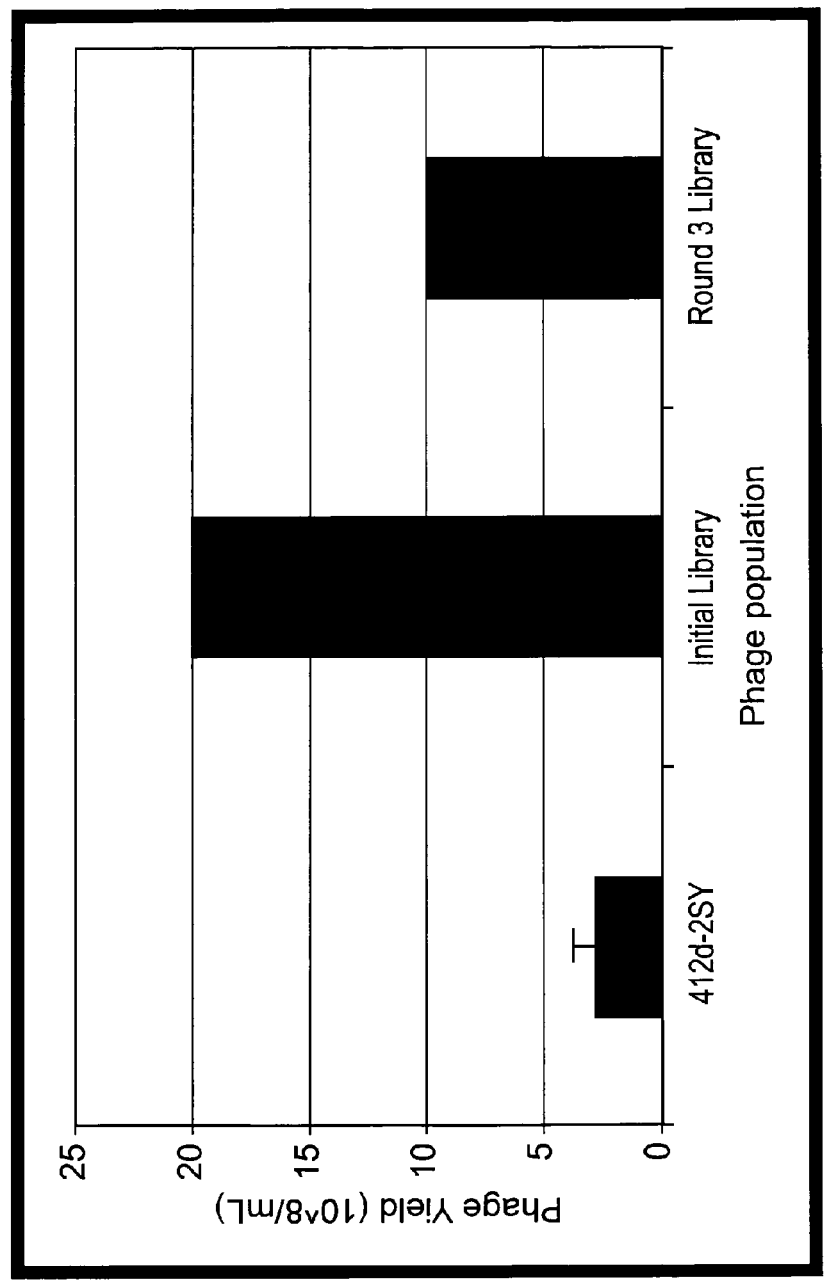
FIG. 9 depicts the results of experiments performed to determine the yield of phage/mL culture of 412d-2SY in comparison with phage yield from the initial library and the library at the third round of selection.
Figure 10:
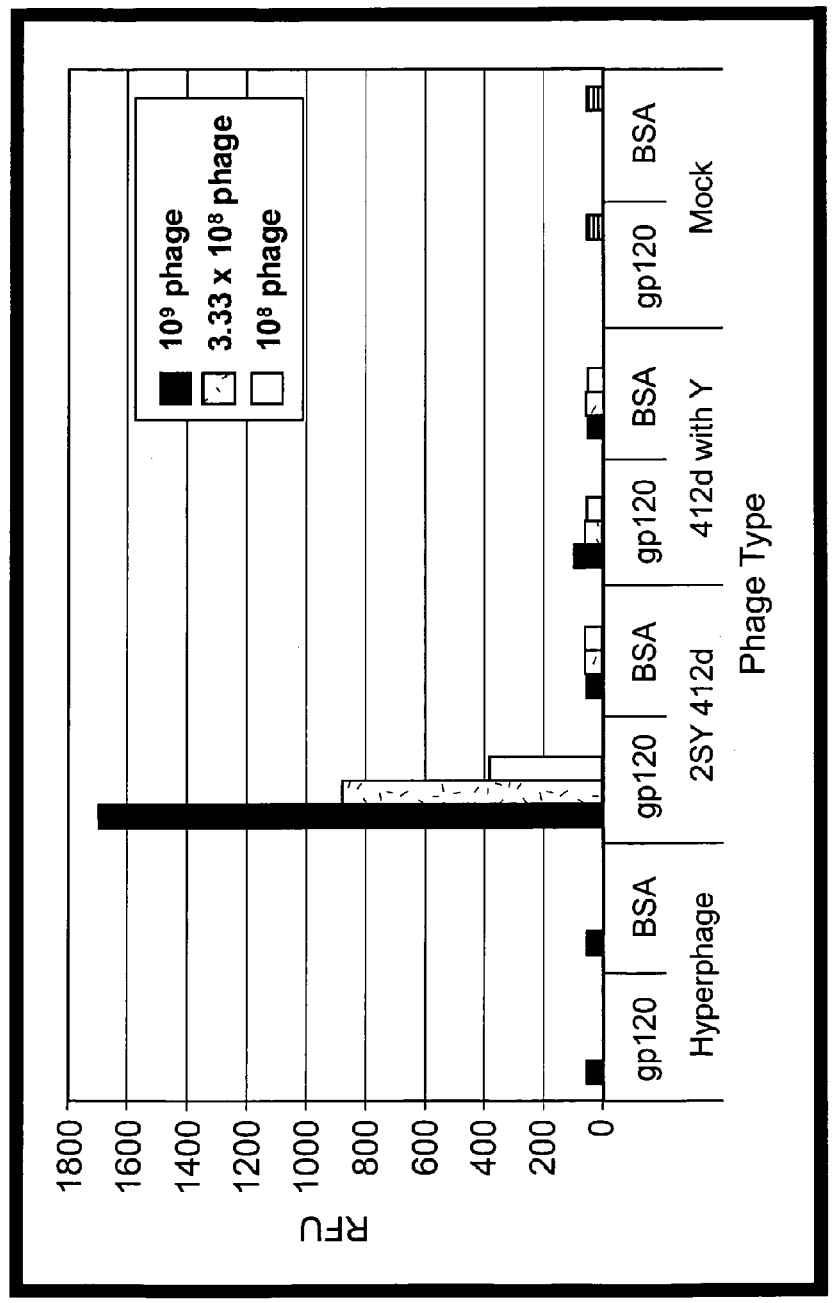
FIG. 10 depicts the results Phage ELISA for gp120 binding with 412d-2SY selected from a doped 412d library compared with 412d-Y where sulfotyrosines were replaced by tyrosines.

To ensure that 412d-2SY (SEQ ID NO: 64) was selected based on its functional merit, we characterized the expression level of phage displaying 412d-2SY and compared it to the expression level of the initial library phage and the library phage at round 3, both of which contained some to many sequences that had no unnatural amino acids. This comparison revealed that phage displaying 412d-2SY were produced at lower yields than the library phage (FIG. 9); therefore, the enrichment for 412d-2SY phage must have been due to a functional advantage rather than any general expression advantage. FIG. 9 depicts the yield of phage per mL culture of 412d-2SY in comparison with phage yield from initial phage library and library at round 3. All phage were produced using SY-X-*E. coli*. For 412d-2SY, titers from three separate phage preparations were averaged and error bar represents+standard deviation. For 412d-2SY, when sulfotyrosine was omitted from the media, phage yield was ~1×106 per mL. 412d-2SY phage were also isolated to test for gp120-binding by enzyme-linked immunosorbent assays (ELISAs). As a natural comparison, phage displaying 412d from pSEX-412d2TAT, in which the two sulfotyrosines are replaced by tyrosines (412d-Y), were produced and similarly tested. As FIG. 10 shows, 412d-2SY effectively binds gp120 over BSA control. Furthermore, the ELISA signal is ~10-fold higher for gp120 binding by 412d-2SY than by 412d-Y. Thus, 412d-2SY was selected based on its binding affinity resulting directly from the two sulfotyrosine residues.

Selection for Anti-Gp120 Antibodies from a Naïve Germline Library in SY-X-*E. coli* Yields a Sulfated Antibody We next performed an evolution experiment for gp120-binding in which a completely naïve germline antibody library, instead of one based on any known gp120-binding sequence, was subjected to selection for binding gp120. Because we did not want to bias this library towards any target, a mixture of human germline heavy chain variable regions were amplified from human genomic DNA and assembled with the A27 germline light chain, using overlap PCR, into scFvs with 6 consecutive residues in the CDR3 loop region completely randomized by site-saturation mutagenesis by NNK (see Methods). Two partially randomized residues flanking these 6 residues were inserted to mimic the natural junctional diversity since $V_H$ gene regions do not end in frame. The library was then cloned into a phagemid vector, yielding an experimental maximal complexity of $2\times10^9$. DNA sequencing revealed that an expected ~17% of clones contained at least one amber codon.

Figure 11A:
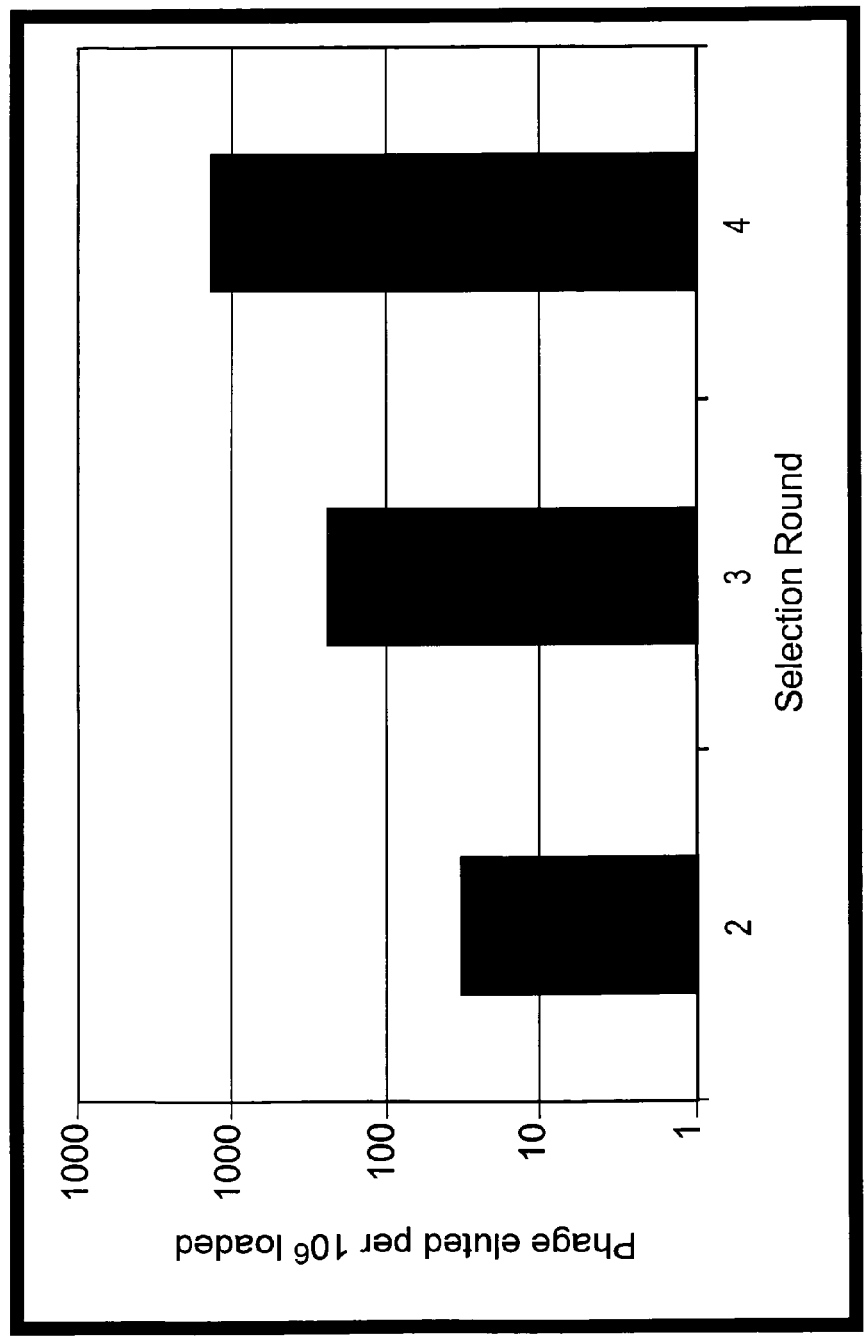
FIG. 11a-b depicts the results of experiments performed to show that clones capable of binding gp120 were enriched in each succeeding round of selection and that clones comprising the unnatural amino acid sulfotyrosine were enriched in each succeeding round of selection.
Figure 11B:
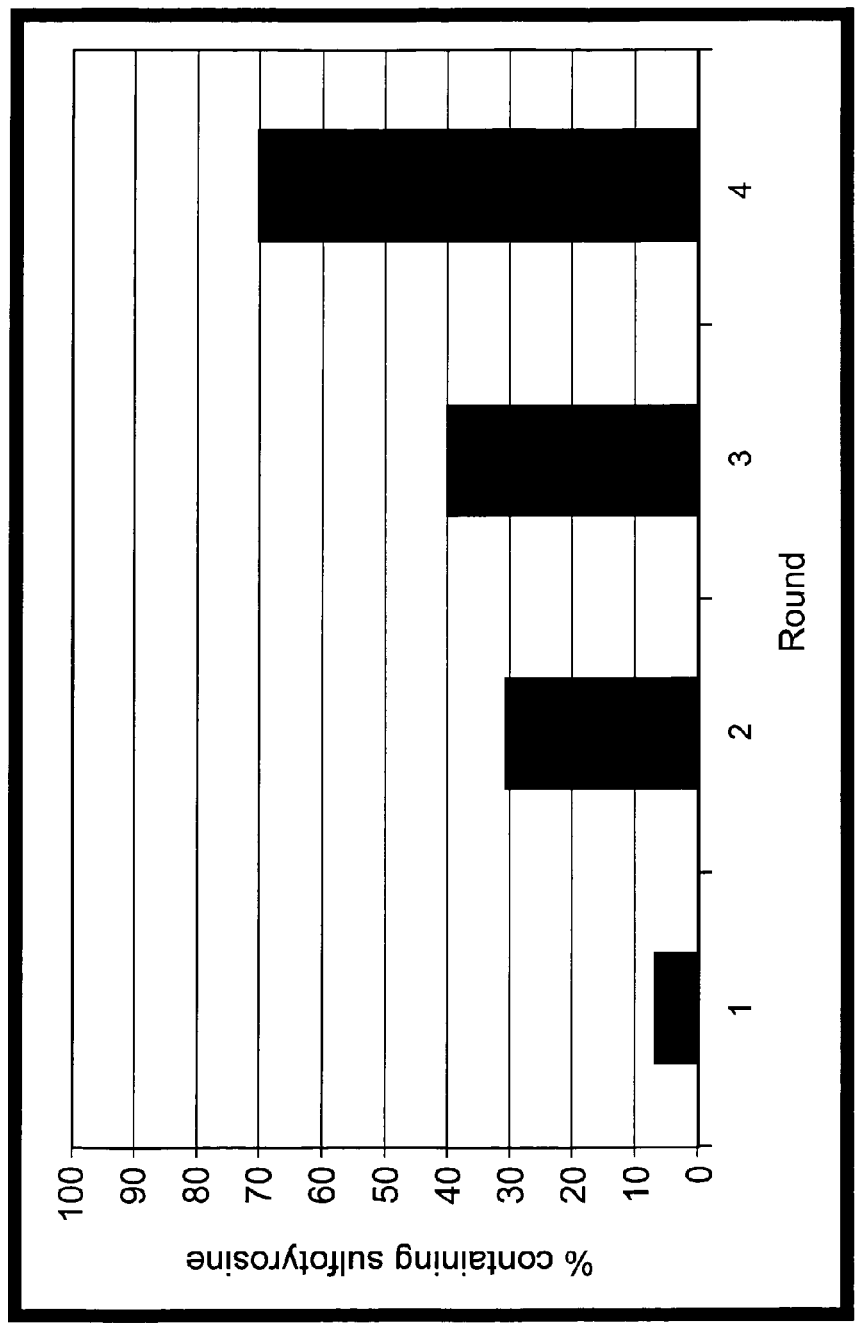

SY-X-*E. coli* were then used to generate phage from this library, which were subsequently panned against gp120. Bound phage were amplified in SY-X-*E. coli* and this process was repeated for a total of four rounds where each additional round conducted under the same stringency had enrichment for gp120 binding over the previous (FIG. 11a). Sequencing revealed a concurrent enrichment for sulfotyrosine in sequenced clones (FIG. 11b). FIG. 11a shows the enrichment for gp120 binding as judged by the eluted phage amount after each round. Round 1 selection was done with much lower stringency than with subsequent rounds (see Methods) in order to minimize arbitrary loss of potential hits when few copies of each clone were present. FIG. 11b shows the increase in the percent clones containing sulfotyrosine after each round as determined by sequencing (n=15-30).

Figure 12:
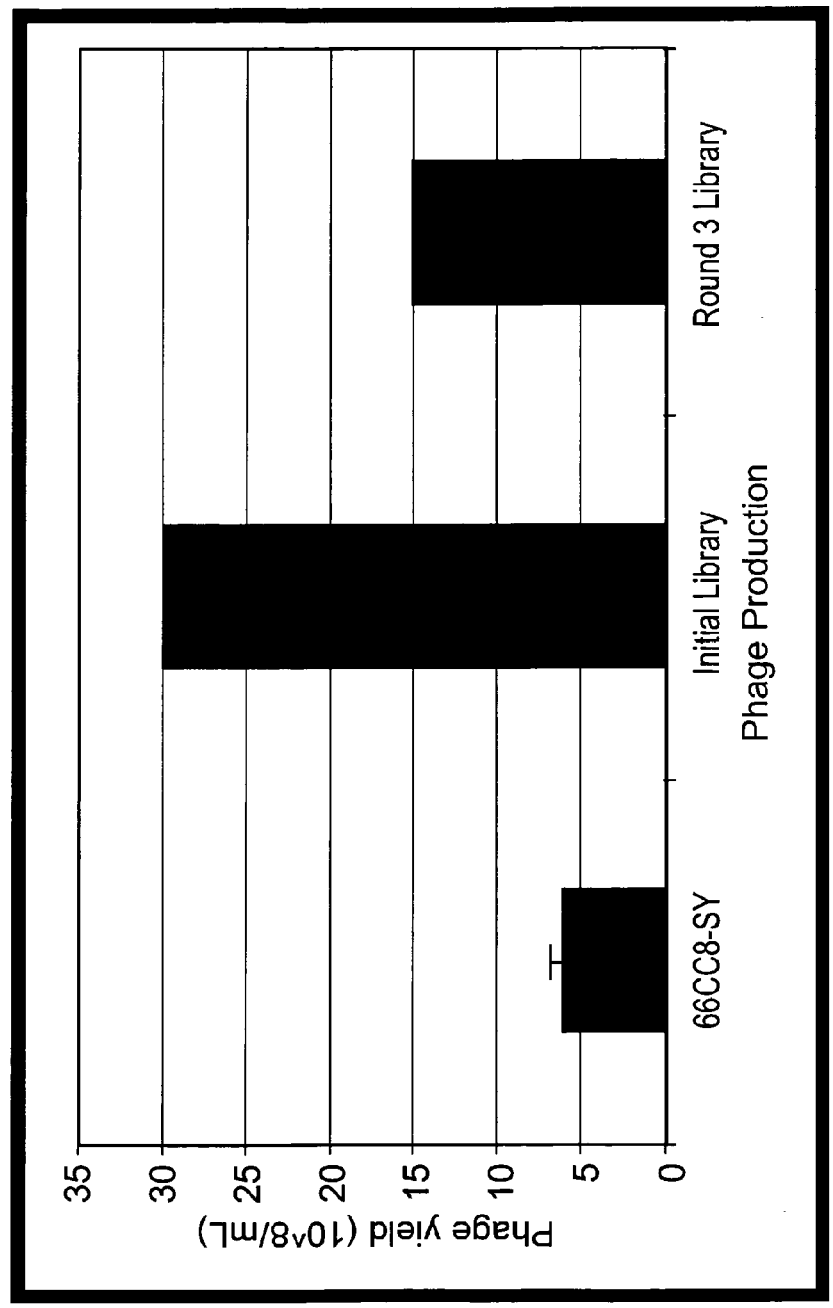
FIG. 12 depicts the results of experiments performed to determine the yield of phage/mL culture displaying 66CC8-SY, in comparison with phage yield from the initial phage library and the library at the third round of selection.

After three rounds, ~40% of the phage population contained a sulfotyrosine; after the fourth round, the library converged primarily on one of these sulfotyrosine-containing antibodies with the sequence . . . E sYGSPRGY . . . , e.g., SEQ ID NO: 70, (sY=sulfotyrosine; amino acids corresponding to the locations of partial randomization are italicized; amino acids corresponding to the locations of full randomization are underlined) and heavy chain V region $V_3$-38. This clone represented 60% of the population (n=20). Yield of phage displaying this scFv (66CC8-SY) in the presence of sulfotyrosine was >100-fold higher than yield of phage in the absence of sulfotyrosine, confirming specific incorporation of sulfotyrosine (5). Yield of phage displaying 66CC8-SY was also compared to yield of phage displaying the initial library and that from round 3, and in both cases phage displaying 66CC8-SY was produced in lower amounts (FIG. 12), as expected from the fact that 66CC8-SY contains an unnatural amino acid. FIG. 12 shows the yield of phage per mL culture of 66CC8-SY in comparison with phage yield from initial phage library and library at round 3. All phage were produced in SY-X-*E. coli*. For 66CC8-SY, titers from three separate phage preparations were averaged and error bar represents+standard deviation. For 66CC8-SY, when unnatural amino acid was omitted from the media, phage yield was ~5×106. Thus, 66CC8-SY was selected over other sequences, including ones containing only canonical amino acids, based on binding affinity. This result demonstrates that evolution with an unbiased, naïve library in a strain encoding sulfotyrosine yields a sulfated antibody as a solution to gp120 binding.

Figure 13A:
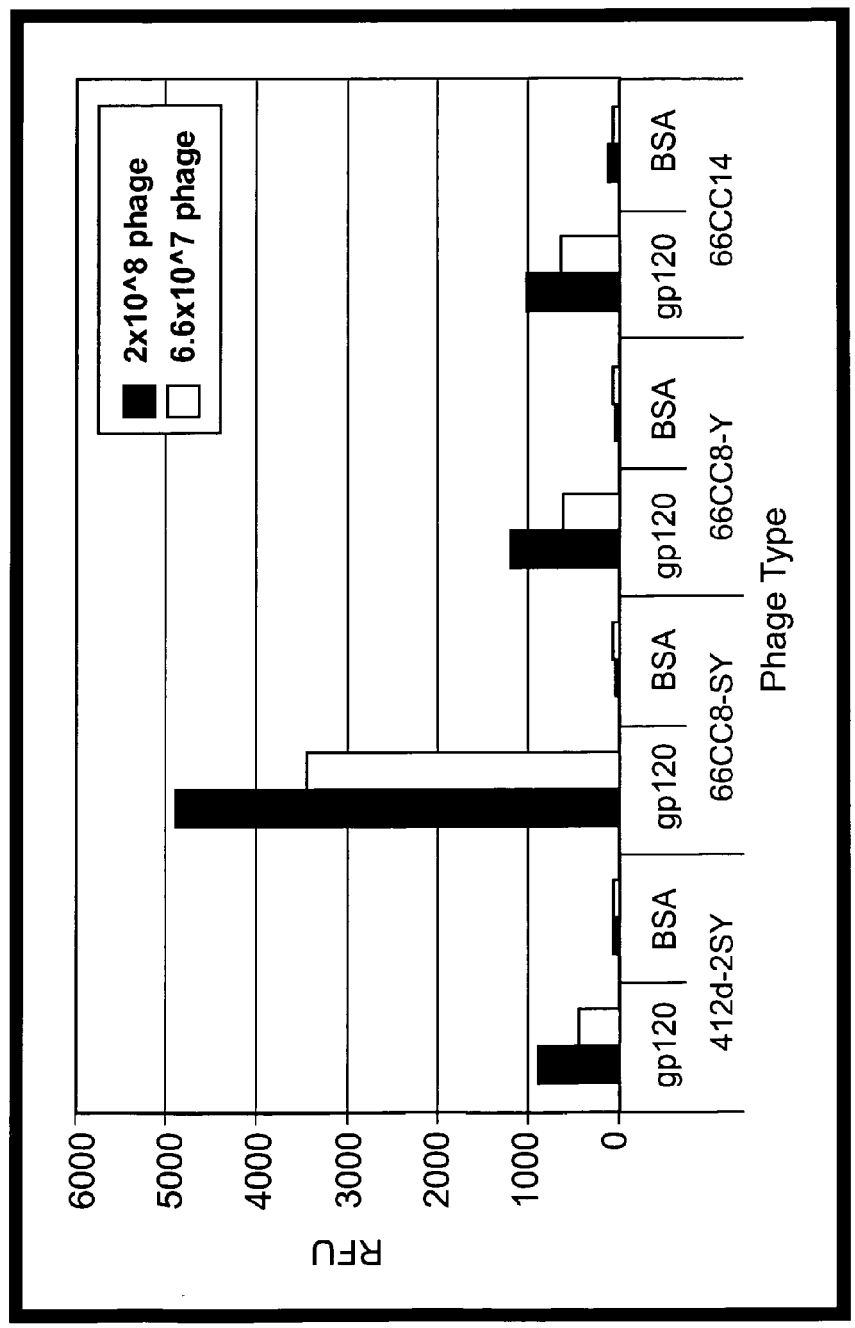
FIG. 13 depicts the results of ELISA experiments performed to determine the affinity of 66CC8-SY, 66CC8-Y, 66CC14, and 412d-2SY for gp120.
Figure 13B:
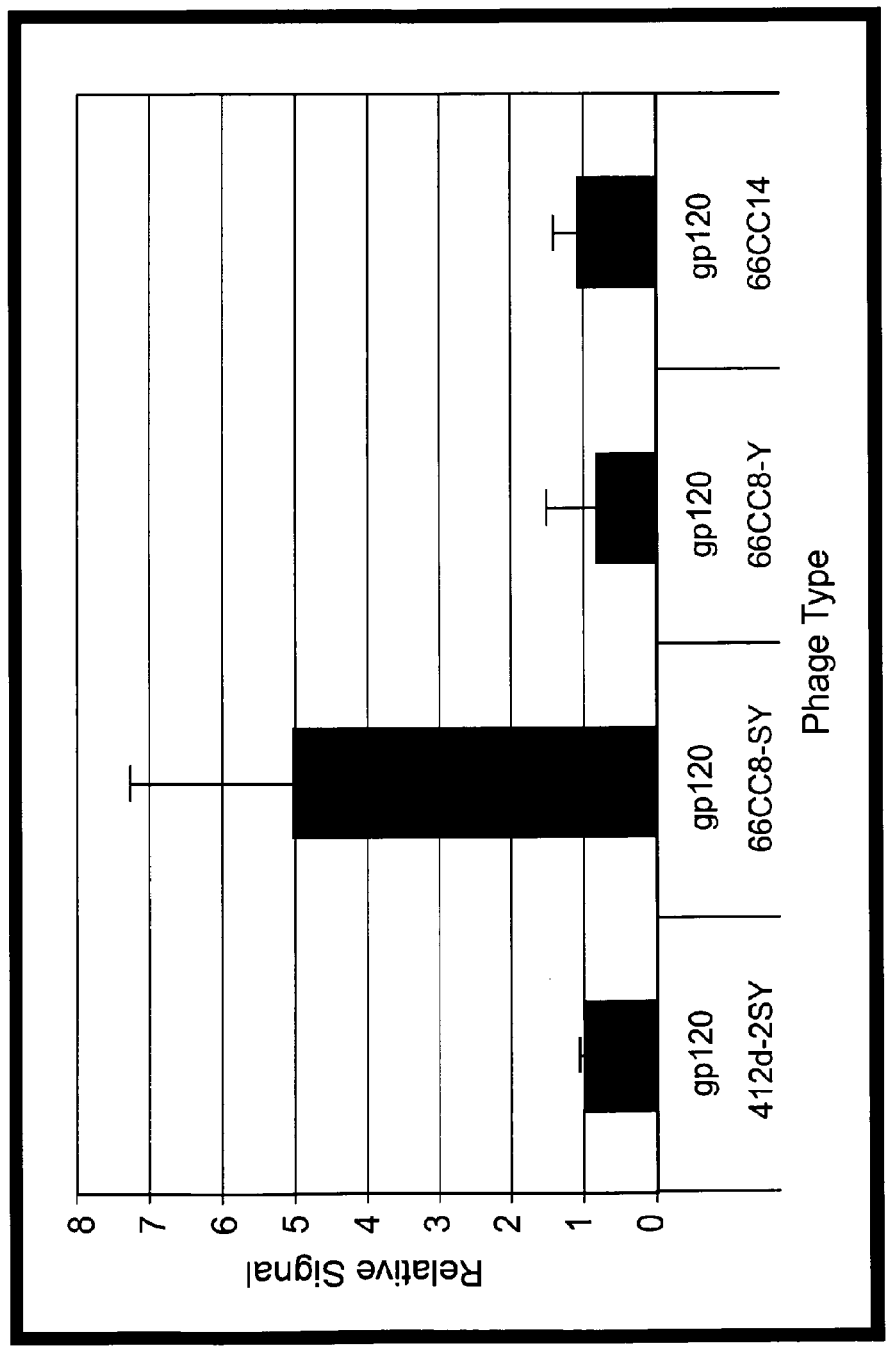

Gp120-binding by 66CC8-SY was then characterized by ELISA. As FIG. 13 shows, 66CC8-SY binds gp120 specifically over BSA control and also outperforms, by approximately 5-fold, the known antibody 412d-2SY. When compared to the most enriched antibody that contained only natural amino acids from the same selection (antibody 66CC14 with the sequence . . . E RRGREGH . . . (e.g., SEQ ID NO: 71) and which represented 20% of the population after round 4, n=20), 66CC8-SY had roughly 4-fold higher affinity (FIG. 13). In fact, 66CC14 shows an appreciable amount of BSA binding and thus its presence in the population can be partly due to non-specific interactions. We also compared 66CC8-SY with its analog where tyrosine replaces sulfotyrosine (66CC8-Y) in order to show that the sulfate residue specifically contributes to the affinity of 66CC8-SY. 66CC8-Y was produced using an aaRS encoding tyrosine in response to TAG and the resulting phage were tested for gp120-binding by ELISA in comparison with phage displaying 66CC8-SY. As FIG. 13 shows, phage-displayed 66CC8-SY produces a ~5-fold higher ELISA signal for gp120 binding than does 66CC8-Y, indicating that sulfotyrosine was properly displayed on phage and demonstrating that the sulfate residue specifically contributes to the affinity of 66CC8-SY. This result is expected since 66CC8-Y and many related sequences should have been present in the starting library population from which 66CC8-SY emerged. We note that in all these cases, the display level of scFv on phage is consistent across clones because of the enforced multivalency of hyperphage, making comparison across samples straightforward.

Figure 14A:
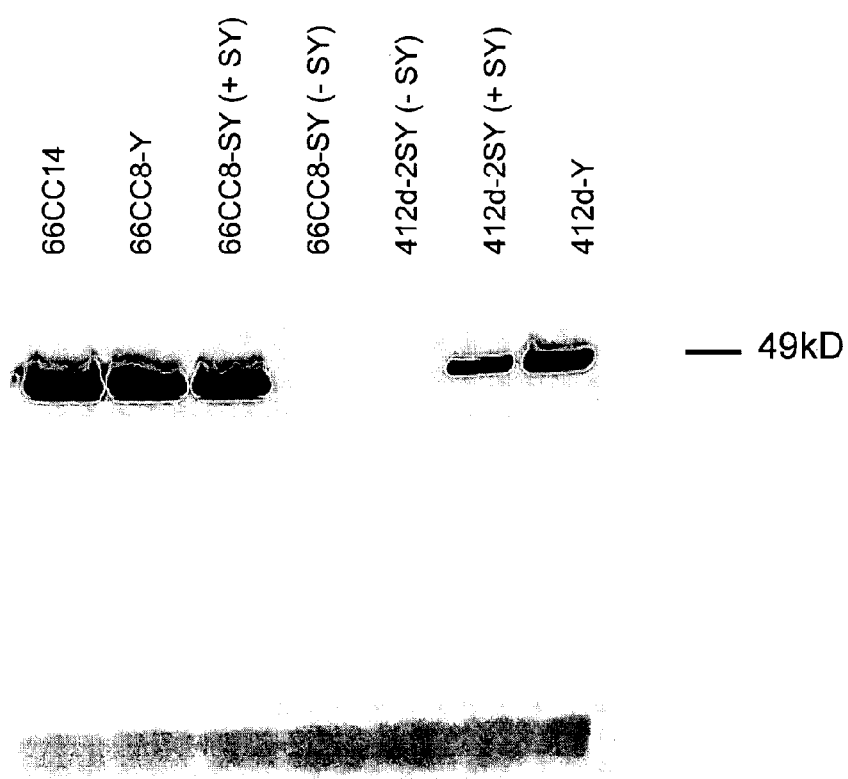
FIG. 14a depicts the Western Blot analysis of protein G purified Fabs using antihuman kappa light chain HRP antibody developed with metal-enhanced DAB kit (Pierce). Samples were run on a denaturing PAGE gel (Invitrogen NuPAGE 4-12% Bis-Tris). For 66CC8-SY and 412d-SY, lanes corresponding to expression in the absence of sulfotyrosine are also presented to show dependence of sulfated antibody expression on the presence of sulfotyrosine.
Figure 14B:
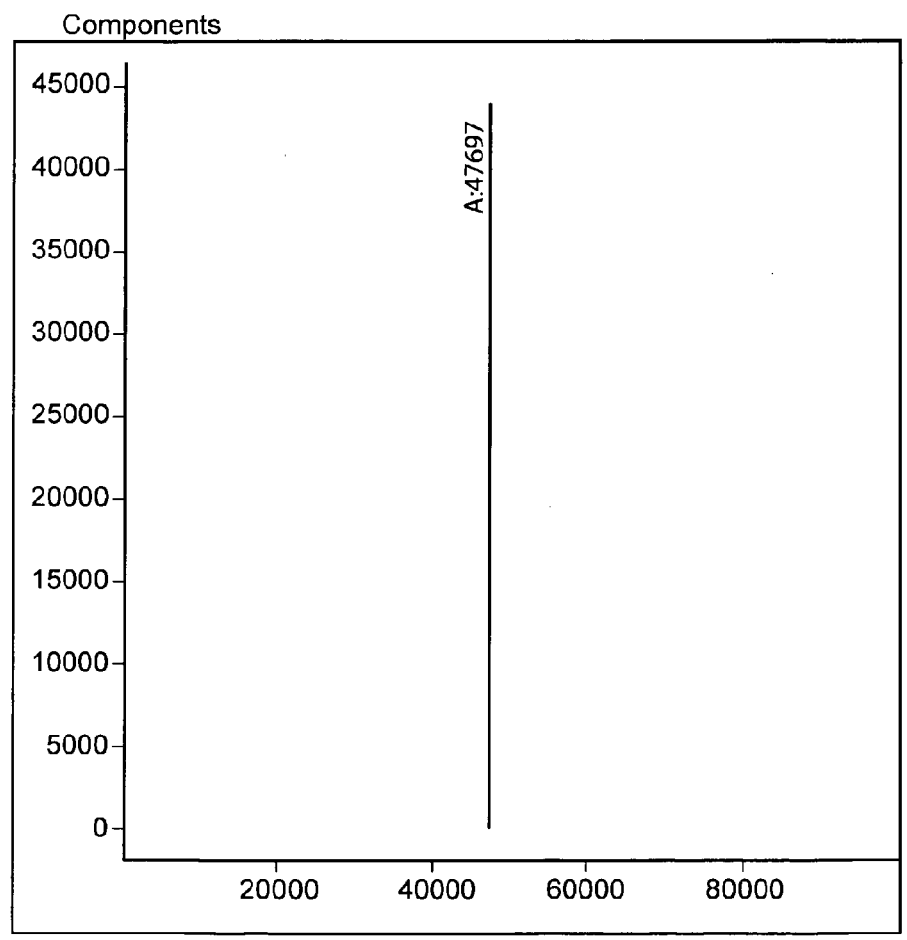
FIGS. 14b-f depict LCMS (ESI-positive) spectra of Fabs 66CC14, 66CC8-SY, 66CC8-Y, 412d-SY, and 412d-Y, respectively.
Figure 14C:
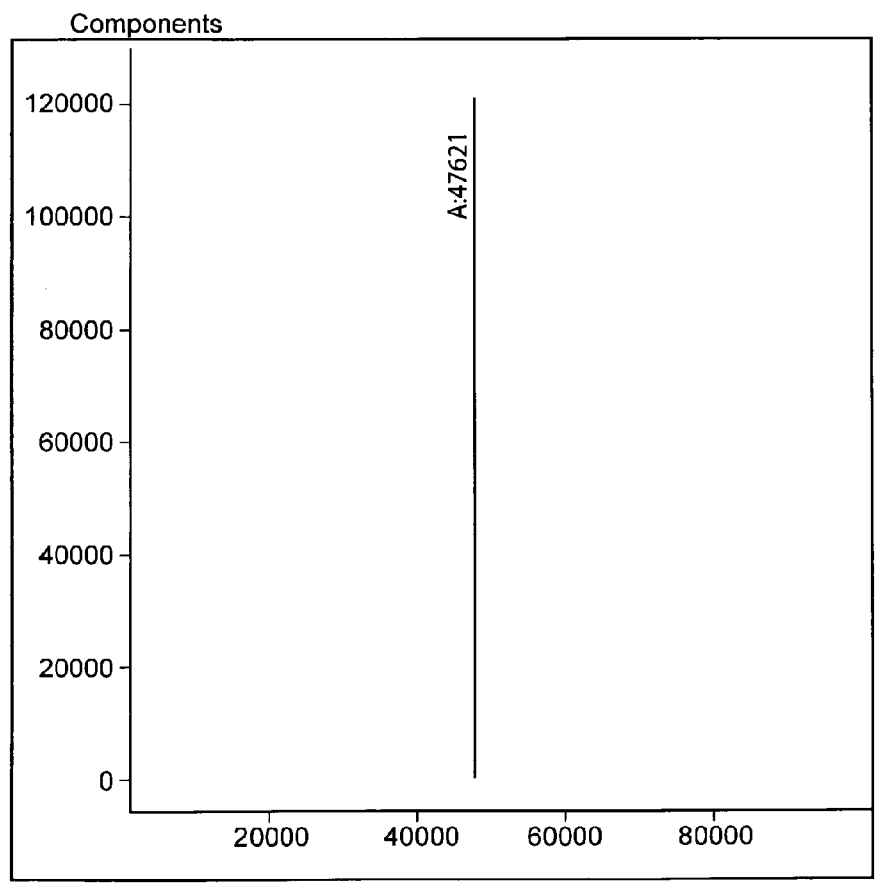
Figure 14D:
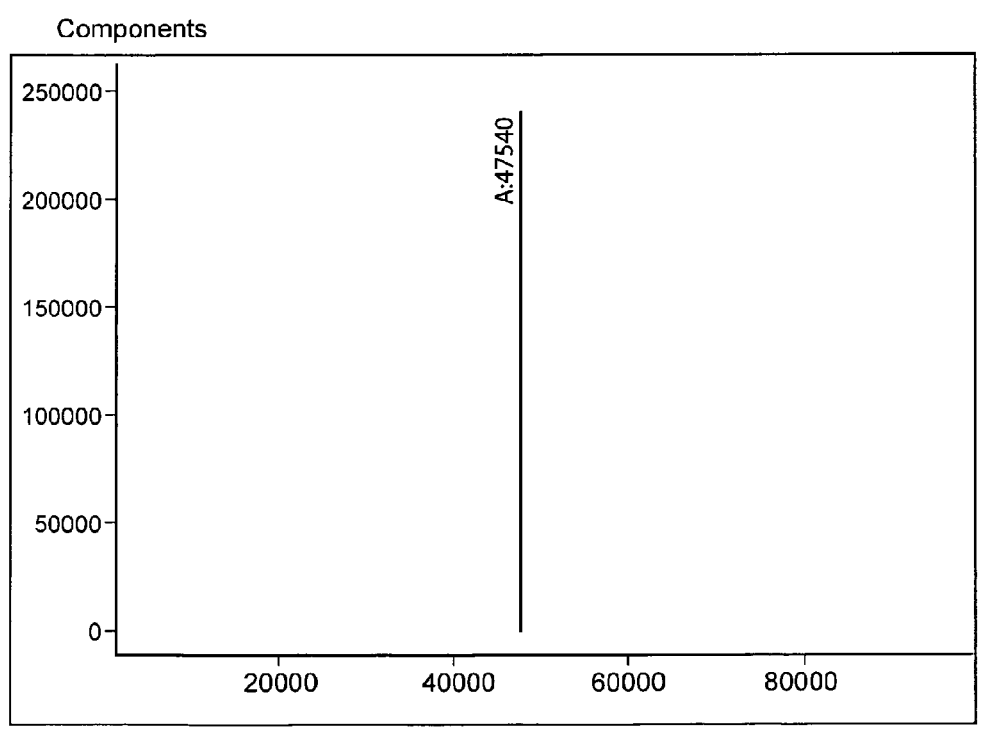
Figure 14E:
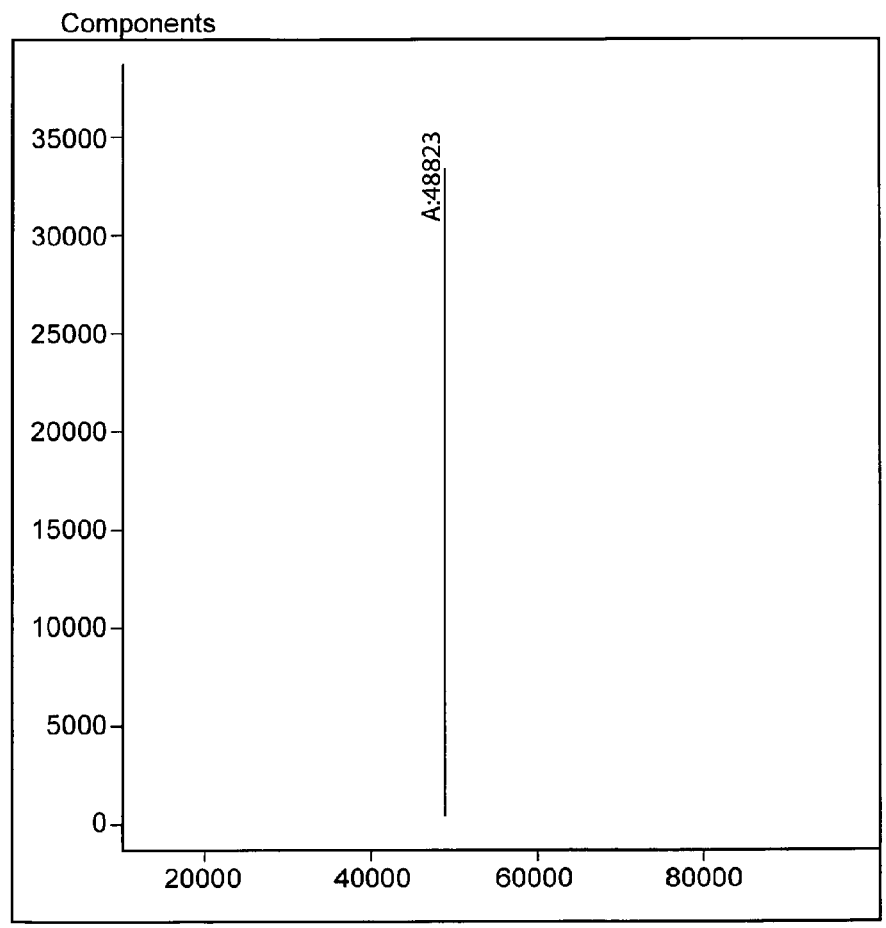
Figure 14F:
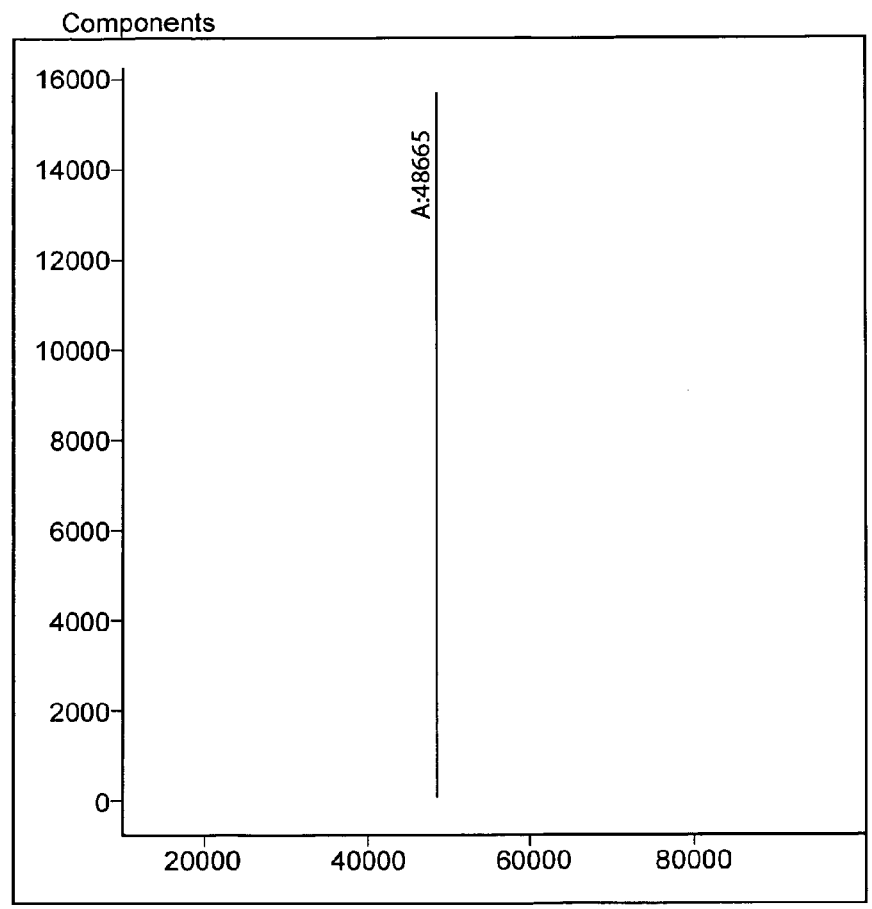
Figure 14G:
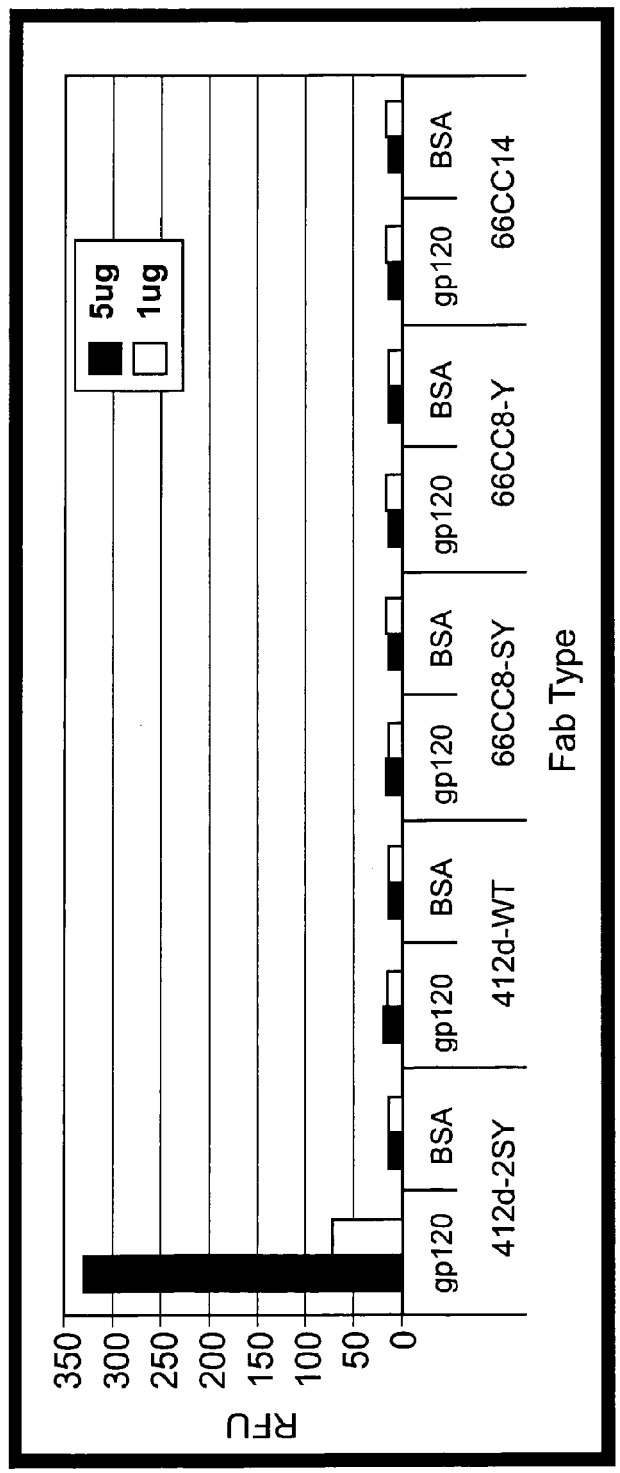
FIG. 14g shows results of ELISAs measuring binding of gp120 by purified Fabs 412d-2SY, 412d-Y, 66CC8-SY, 66CC8, and 66CC14.

We next attempted to express and characterize free scFvs without fusion to phage. Although expression of the scFv 66CC8-SY using an orthogonal tRNA/aaRS pair specific for sulfotyrosine gave yields comparable to expression of 66CC8-Y (~7 mg/L), all protein produced was insoluble and resisted multiple attempts at refolding. When converted to the Fab format, 66CC8-SY, 66CC8-Y, and 66CC14 (purified yields of 0.8, 1.0, and 1.0 mg/mL, respectively) lost activity for gp120 binding (FIG. 14). We believe that the germline variable regions corresponding to these selected antibodies are unstable and require the scFv linker, explaining both the loss of activity upon conversion to Fab format and the resistance to refolding in free scFv format. This is in contrast to expression of free 412d-2SY and 412d-Y (purified Fab yields of 0.25 and 0.7 mg/mL, respectively), both of which gave high yields of folded scFvs, and retained all activity for gp120 binding when converted to Fab format. Although there is no literature Kd value for comparison, Fab 412d-2SY bound gp120 effectively and in a sulfate-dependent manner, with >15-fold higher affinity than Fab 412d-Y by ELISA (FIG. 14). FIG. 14a depicts the Western Blot analysis of protein G purified Fabs using antihuman kappa light chain HRP antibody developed with metal-enhanced DAB kit (Pierce). Samples were run on a denaturing PAGE gel (Invitrogen NuPAGE 4-12% Bis-Tris). For 66CC8-SY and 412d-SY, lanes corresponding to expression in the absence of sulfotyrosine are also presented to show dependence of sulfated antibody expression on the presence of sulfotyrosine. FIGS. 14b-f depict LCMS (ESI-positive) spectra of Fabs 66CC14, 66CC8-SY, 66CC8-Y, 412d-SY, and 412d-Y. FIG. 14g shows results of ELISAs measuring binding of gp120 by purified Fabs 66CC14, 66CC8-SY, 66CC8-Y, 412d-2SY, and 412d-Y, respectively. This is analogous to mammalian sulfated 412d, which immunoprecipitates gp120 only when sulfated. Selection for stability or the use of libraries derived from Fabs rather than naïve germline scFvs can prevent such problems of folding and format conversion.

Discussion

We have developed a system for protein evolution in which unnatural amino acids beyond the canonical 20 are available in the exploration of protein function space. In contrast to previous attempts that include unnatural or non-canonical amino acids in directed evolution experiments (21, 22), unnatural amino acids in our system are genetically encoded and require only the unique codon, TAG, for site-specific incorporation. Therefore, translation with unnatural amino acids utilizes the same fundamental paradigm as translation with natural amino acids, resulting in unrestricted 21 amino acid protein evolution. There is, however, one qualification:

the yield bias favors sequences containing only natural amino acids. Our phage-based system is therefore optimized to mitigate this bias such that diversification strategies resulting in populations with sequences containing unnatural amino acids in conjunction with sequences containing only canonical amino acids can be subject to evolution for function. Since the yield bias is minimized but not completely removed, selections, including all those we have described, require that unnatural amino acids contribute to function for sequences containing them to be maintained in the population.

X-*E. coli* strains that incorporate four unnatural amino acids were optimized for phagemid-based directed evolution by manipulation of growth conditions, and one strain encoding the unnatural amino acid sulfotyrosine has been used to evolve gp120-binding antibodies from an unbiased, naïve germline antibody library. In this experiment, the antibody population converged on a novel clone that contains a sulfotyrosine, which directly contributes to gp120-binding affinity. The selection of this clone from a completely naïve library provides the first evidence that an expanded genetic code can confer a selective advantage through the functional contribution of an unnatural amino acid.

Optimization of this system to minimize bias was done with sequences that contain only one unnatural amino acid. Phage yield bias against sequences that contain more than one unnatural amino acid may therefore be greater, thus requiring a more pronounced functional advantage for such sequences to prevail across multiple rounds. Any such bias against selection of sequences containing multiple unnatural amino acids can be overcome by iterative selection experiments. For example, if the fittest sequences in a given selection contain a single unnatural amino acid, a second selection experiment can be done where the unnatural amino acid from the winning sequences is fixed and other surrounding amino acids are randomized. With this constrained library, the incorporation of a second unnatural amino acid would again experience only a minimized bias, as all members of the population would already contain a first unnatural amino acid. Naturally, this approach is optional if the functional advantage of having multiple unnatural amino acids overcomes the associated expression bias. For example, 412d-2SY, which contains two of the unnatural amino acid sulfotyrosine, is selected directly from a 412d-based library that is initially dominated by sequences containing only natural amino acids using our system.

Although this system was optimized to allow evolution with the four unnatural amino acids sulfotyrosine, bipyridyl-alanine, 4-borono-phenylalanine, and para-acetylphenylalanine, chosen on the basis of their unique chemical functionalities, phage-based evolution with expanded genetic codes can optionally be used with any unnatural amino acids incorporated by the orthogonal aaRS/tRNA pairs (approximately 45 so far) including ones yet to be fully characterized. This fact, combined with the versatility of phage display and the array of available library design and diversification strategies (13) can now allow for evolution of novel binding modes, catalytic activities, and structures where unnatural amino acids expand the range and type of function that can be achieved.

Methods

X-*E. coli* Plasmid Design and Construction tRNA/aaRS pairs were encoded on pCDF plasmids. The pCDF plasmid carries a replicon derived from CloDF13 (23) and encodes MjtRNA$^{Tyr}_{CUA}$ and a mutant MjTyrRS that specifically charges MjtRNA$^{Tyr}_{CUA}$ with an unnatural amino acid. To construct pCDF-Keto that encodes a mutant aaRS that charges MjtRNA$^{Tyr}_{CUA}$ with para-acetylphenylalanine, an insert gene bearing the CloDF13 replicon was amplified from vector pCDF-1b (Novagen) by PCR using primers:

MT01: (SEQ ID NO: 72)
5'-GTGTTGTTGTTGTTGTATACCAAATAGCTAGCTCACTCGGTC-3'
and

MT02: (SEQ ID NO: 73)
5'-GTTGTTGAGCTCGATAAATTGCACTGAAATCTAGAGCGGTTC-3'

The insert was then digested with restriction enzymes AccI and SacI, purified, and ligated into an AccI/SacI cut pSup vector (24). Sequencing revealed a G to A mutation in the proK promoter of the second tRNA cassette in the plasmid, which resulted in more viable clones that were functionally active. This mutation was therefore allowed to remain. Once pCDF-Keto was made, other synthetases were swapped in using the restriction sites NdeI and PstI to generate pCDF-Bpy, which incorporates bipyridyl-alanine; pCDF-SY, which incorporates sulfotyrosine; and pCDF-1BG11, which incorporates 4-borono-phenylalanine, all in response to the amber codon. Each of these pCDF plasmids were then transformed into Top10 F' (Invitrogen) to create Keto-X-*E. coli*, Bpy-X-*E. coli*, SY-X-*E. coli*, and Boro-X-*E. coli* and maintained on the antibiotics chloramphenicol (30 µg/mL) and tetracycline (30 µg/mL.

pSEX-GermTAG and pSEX-Germ2TAT Plasmid Construction

A Fab format antibody containing $V_H$ 3-23 and $V_L$ A27 with a TAG in the $V_H$ CDR3 loop was synthesized by Blue Heron. To construct pSEX-GermTAG, first the light chain gene was amplified from this synthetic Fab antibody gene with primers:

LC1:
5'-GCACGCGTAGAAATTGTGTTGACG-3' (SEQ ID NO: 74)
and

LC2:
5'-CTTTGGATCCAGCGGCCGCCCGTTTGATTTCCACCTTGGTCCCT
TGGCC-3' (SEQ ID NO: 75)

The light chain gene was then digested with Mlu and BamHI and subsequently inserted into a similarly digested pSEX81 (Progen) to create pSEX-GermA27. The heavy chain gene was then amplified from the synthetic Fab antibody gene with primers HC1:
5'-CGGCCATGGCTGAGGTGCAGCTGTTGGAGTCTGG-3' (SEQ ID NO: 76)
and HC2:
5'-CTTCAAGCTTTGGGGCGGATGCACTCCCTGAGGAGACGGTGACC
AGGGTTCCTTGG-3' (SEQ ID NO: 77)

and then digested with NcoI and HindIII. This sequence was inserted into a similarly digested pSEX-GermA27 to create pSEX-GermTAG. Quickchange (Stratagene) site-directed mutagenesis was used to create pSEX-GermTAT where the TAG codon in pSEX-GermTAG is replaced by a TAT codon.

In these pSEX plasmids, a trypsin site is present between the scFv and pIII, which allows for the removal of displayed scFvs to reveal infective pIII. This is important for elution and infection.

PSEX-GermNNK Library Construction

A heavy chain gene fragment containing $V_H$-23 was amplified from the synthetic Fab antibody gene with primers

```
VH-23-F:                                (SEQ ID NO: 78)
5'TCTCGAAATCCATGGCTGAGGTGCAGCTGTTGGAGTCTGG-3'
and

VH3-23-R:
5'-TCTTTCGCACAGTAATATACGG-3'.   (SEQ ID NO: 79)
```

To this fragment was added a randomized CDR3 loop using overlap PCR with primers

```
NNK1:
5'-CCGTATATTACTGTGCGAAAGANNNKNNKNNKNNKNNKNNK
NACTACTTTGACTACTGGGG-3' (SEQ ID NO: 80)
and NNK2:
5'-AGCCATCGCGGCCGCGCTAGCTGAGGAGACGGTGACCAGGG
TTCCTTGGCCCCAGTAGTCAAAG-3' (SEQ ID NO: 81)
``` where N=A, T, G, or C and K=G or T. The final gene product, which contains the full heavy chain library, was then amplified with primers

```
HC1:                                    (SEQ ID NO: 82)
5'-CGGCCATGGCTGAGGTGCAGCTGTTGGAGTCTGG-3'
and HC2:
5'-CTTCAAGCTTTGGGGCGGATGCACTCCCTGAGGAGACGGTGA
CCAGGGTTCCTTGG-3'.   (SEQ ID NO: 83)
```

The product was digested at restriction sites NcoI and HindIII and inserted into a similarly digested pSEX-GermTAT to create the library pSEX-GermNNK. The ligation mixture was precipitated and the product was transformed into electrocompetent Top 10 F' cells to afford $5 \times 10^8$ total transformants. After overnight growth in 2YT supplemented with 100 µg/mL ampicillin, 30 µg/mL tetracycline, and 1% glucose, the supercoiled DNA was isolated. This DNA was then transformed into Keto-X-*E. coli*, Bpy-X-*E. coli*, SY-X-*E. coli*, and Boro-X-*E. coli* for phage display studies on the population.

pSEX-412d2TAT and pSEX-412d2TAG Construction

The scFv coding region was amplified from a mammalian 412d expression vector (18) using primers

```
412dF:
5' CACGCCATGGCTGAGGTGCAGCTGGTGCAGTCTGGGGCTGAG
GTG-3' (SEQ ID NO: 84)
and 412dB:
5'-CTTTGGATCCAGCGGCCGCCCGTTTGATTTCCACCTTGGTCC
CCTGGCCAAA-3'.   (SEQ ID NO: 85)
```

The resulting scFv was digested with NcoI and BamHI and inserted into a similarly digested pSEX81 to yield pSEX-412d2TAT. Quickchange (Stratagene) site-directed mutagenesis was used to replace the two locations of mammalian tyrosine sulfation (residues 104 and 107) with amber codons to yield pSEX-412d2TAG.

Creation of a 412d Library

To create a 412d library with residues Pro101, Tys104, Asn105, Tys107, Ala108, Pro109, Gly112, and Met113 randomized, we first amplified a heavy chain fragment from pSEX-412d2TAG with the primers

```
412dLib1: 5'-CCGCTGGCTTGCTGCTGCTG-3'       (SEQ ID NO: 86)
and

412dLib2: 5'-GTAAGGGCTCGCACAGTAAAATACGGCC-3'. (SEQ ID NO: 87)
```

The resulting product was then extended with overlap PCR using the primers

```
412dLib3:
5'-GCCGTATTTTACTGTGCGAGCCCTTACNNKAATGACNNKNN
KGACNNKNNKNNKGAGGAGNNKNNKAGCTGGTACTTCGATCTCT
G-3'                                    (SEQ ID NO: 88)
and 412dLib4:
CAGAGATCGAAGTACCAGCT                    (SEQ ID NO: 89)
``` where N=A, T, G, or C and K=G or T. A second fragment was amplified from pSEX-412d2TAG using the primers

```
412dLib5:    AGCTGGTACTTCGATCTCTG (SEQ ID NO: 90)
and

412dLib6:    CTCTGATATCTTTGGATCCA (SEQ ID NO: 91)
``` and the two fragments were assembled by overlap PCR to give the 412d gene library. This library was then digested with NcoI and BamHI and inserted into a similarly digested pSEX81 vector. The ligation product was precipitated with tRNA assistance and transformed into Top 10 F' cells, affording $2 \times 10^8$ total transformants. After overnight growth in 2YT supplemented with 100 µg/mL ampicillin, 30 µg/mL tetracycline, and 1% glucose, the supercoiled DNA was isolated. This DNA was then transformed into SY-X-*E. coli* for phage display and selection of anti-gp120 antibodies.

Creation of a Naïve Germline Antibody Library for Selection of Anti-Gp120 Antibodies A mixture of germline $V_H$ fragments was amplified from human cDNA using primers

```
VH-Mix-F:
5'-TCTCGAAATCCATGGCTCAGGTGCAGCTGGTGCAGTCTGG-3' (SEQ ID NO:
 92)
and VH-Mix-R:
5'-TCTCTCGCACAGTAATACACGGCCG-           (SEQ ID NO: 93)
3'.
```

Annealing temperature for this PCR reaction was 56° C. To these fragments were added a randomized CDR3 loop using overlap PCR with primers

```
NNK1:
5'-CGGCCGTGTATTACTGTGCGAGAGANNNKNNKKNKNNKNNKNN
KNACTACTTTGACTACTGGGG-3'            (SEQ ID NO: 94)
and NNK2:
5'-AGCCATCGCGGCCGCGCTAGCTGAGGAGACGGTGACCAGGGTT
CCTTGGCCCCAGTAGTCAAAG-3'            (SEQ ID NO: 95)
``` where N=A, T, G, or C and K=G or T. The final gene products were then amplified with primers

```
VH66CC-F:
5'-CCGGCCATGGCTCAGGTGCAGCTGGTGCAGTCTGG-3' (SEQ ID NO: 96)
and

VH66CC-R:
5' CTTCAAGCTTTGGGGCGGATGCACTCCCTGAGGAGACGGTGAC
CAGGGTTCCT-3'.                      (SEQ ID NO: 97)
```

This PCR library was digested with NcoI and HindIII and inserted into a similarly digested pSEX-GermTAT to create a library of naïve germline scFvs. The ligation mixture was precipitated and the product was transformed into electro-competent Top 10 F' cells to obtain 2×10⁹ total transformants. After overnight growth in 2YT supplemented with 100 μg/mL ampicillin, 30 μg/mL tetracycline, and 1% glucose, the supercoiled DNA was isolated. This DNA was then transformed into SY-X-*E. coli* for phage display and selection of anti-gp120 antibodies.

Phage Production

In all experiments carried out under optimized conditions, the following phage expression protocol was used. First, an X-*E. coli* culture transformed with either phagemid library or single phagemid clone DNA is grown overnight in 2YT supplemented with 100 μg/mL ampicillin, 30 μg/mL tetracycline, 30 μg/mL chloramphenicol and 1% glucose. After saturation is reached, a total volume equal to 12.5% of the final phage expression volume is removed from the culture, spun down, and resuspended in a volume of 2YT equal to 25% of the final phage expression volume. The 2YT is supplemented with 100 μg/mL ampicillin, 30 μg/mL tetracycline, and 30 μg/mL chloramphenicol. To this culture is added hyperphage (Progen) at 20 MOI (MOI=multiplicity of infection). The resulting culture is then incubated at 100 rpm for 1 hour at 37° C., after which the cells are spun down and the media removed. The phage are then resuspended in the desired final phage expression volume of 2YT supplemented with 100 μg/mL ampicillin, 50 μg/mL kanamycin, and 30 μg/mL chloramphenicol. The unnatural amino acid corresponding to the X-*E. coli* used is added directly to the media and the phage culture is incubated at 280 rpm for 18 hours at 30° C. For Keto-X-*E. coli*, Bpy-X-*E. coli*, SY-X-*E. coli*, and Boro-X-*E. coli*, unnatural amino acids are added at 8 mM, 15 mM, 1.5 mM, and 6.5 mM (13 mM of the racemic mixture), respectively. For Bpy-X-*E. coli*, 20 mM $FeSO_4$ was also added to prevent toxicity associated with iron depletion. For Boro-X-*E. coli*, 25 mM NaOH was added to solubilize the amino acid. Para-acetylphenylalanine was synthesized by Synchem based on published procedures (7), sulfotyrosine was purchased from Senn Chemicals and Bachem, and 4-borono-phenylalanine was purchased from Aldrich as a mixture of D and L isomers. For the synthesis of bipyridyl-alanine, see below.

After phage production, the media was collected and cells were discarded. The media was then concentrated down to a convenient volume using 10 kD cutoff concentrators (Amicon). The concentrated phage was then precipitated by the addition of 5× phage precipitation buffer (20% PEG 8000, 2.5 mM NaCl) and dissolved in a convenient volume of phosphate buffered saline, pH 7 (PBS). Precipitation was done twice.

Synthesis of Bipyridyl-Alanine

5-Methyl-2,2'-bipyridine

A mixture of 2-bromo-5-methylpyridine (5.0 g, 29 mmol), 2-tributylstannylpyridine (10 g, 27 mmol) and $Pd(PPh_3)_4$ (2.0 g, 1.7 mmol) in dry toluene (250 mL) was stirred for 48 h at 110° C. The reaction mixture was filtered over Celite and evaporated under reduced pressure. The residue was dissolved in EtOAc and washed with saturated aqueous $NaHCO_3$ solution, and the organic layer was dried over $MgSO_4$ and concentrated under reduced pressure. Flash column chromatography (0.5% MeOH in $CH_2Cl_2$) afforded methyl-2,2'-bipyridine (3.5 g, 75%) as a colorless oil. $^1$H-NMR (500 MHz, $CDCl_3$): δ 2.47 (s, 3H), 7.35 (dd, 1H), 7.70 (dd, 1H), 7.87 (m, 1H), 8.36 (d, 1H), 8.43 (d, 1H), 8.58 (d, 1H), 8.74 (dd, 1H).

Diethyl 2-(2,2-bipyridine-5-ylmethyl)-2-acetamidomalonate

Methyl-2,2'-bipyridine (1.7 g, 10 mmol) in a mixed solvent (100 mL) of water and benzene (1:1) was irradiated and refluxed using a halogen lamp (150 W). Bromine (1.6 g, 10 mmol) was added and the mixture was heated to reflux for 30 min. The solution was concentrated under reduced ressure and dissolved in EtOAc. The organic layer was washed with saturated aqueous NaHCO$_3$ solution, dried over MgSO$_4$, and concentrated under reduced pressure to afford the crude brominated product. A mixture of diethyl acetamidomalonate (2.6 g, 12 mmol) and sodium hydride (0.48 g, 12 mmol, 60% in mineral oil) in dry DMF (50 mL) was stirred for 30 min at 0° C. To the solution was added the crude product in dry DMF (20 mL) at 0° C. and the mixture was stirred for 1 h at room temperature. The reaction mixture was diluted with EtOAc (200 mL) and washed with a 10% aqueous sodium thiosulfate solution (2×150 mL). The organic layer was dried over MgSO$_4$ and concentrated under reduced pressure. The crude product was purified by flash column chromatography (0.5% MeOH in CH$_2$Cl$_2$) to give diethyl 2-(2,2'-bipyridine-5-ylmethyl)-2-acetamidomalonate (2.5 g, 65%) as a white solid. $^1$H-NMR (500 MHz, CDCl$_3$): δ 1.38 (m, 6H), 2.15 (s, 3H), 3.81 (s, 2H), 4.35 (m, 4H), 6.68 (s, 1H), 7.36 (dd, 1H), 7.55 (dd, 1H), 7.87 (m, 1H), 8.36 (d, 1H), 8.41 (d, 1H), 8.42 (d, 1H), 8.74 (dd, 1H).

Bipyridyl-alanine:
3-(2,2'-Bipyridin-5-yl)-2-aminopropanoic acid

Diethyl 2-(2,2'-bipyridin-5-ylmethyl)-2-acetamidomalonate (2.5 g, 6.5 mmol) in 12 M HCl was heated to reflux for 6 h. The reaction mixture was concentrated under reduced pressure to give the product (2.3 g, 99%) as a white solid in HCl salt form. $^1$H-NMR (500 MHz, CDCl$_3$): δ 3.59 (m, 2H), 4.58 (t, 1H), 8.11 (m, 1H), 8.40 (dd, 1H), 8.67 (d, 1H), 8.70 (m, 1H), 8.83 (d, 1H), 8.99 (dd, 1H). LC-MS (ESI) for calculated C$_{13}$H$_{13}$N$_3$O$_2$ (M+1) 243.1, observed 243.1.

Phage Quantification

Two methods were used to titer phage (16). For applications such as selection where infective phage are the relevant population, phage was quantified by infection of Top 10 F' cells. Specifically, a small volume of phage was digested with 1.75 μg/mL trypsin (Worthington Biochemicals) and used to infect Top 10 F' cells. The amount of infected cells was then determined by plating dilutions on selective plates (ampicillin plates were used for pSEX-based phagemids). For applications such as ELISA where the total particles of phage is the relevant population, phage were coated onto ELISA plates, blocked with 2% milk in PBS, washed several times with PBST (PBS+0.025% Tween 20), bound by an anti-M13 polyclonal antibody (NEB) in 2% milk PBST, and detected with a QuantaBlu fluorogenic substrate (Pierce). This sample was compared to a standard curve where known amounts of hyperphage were adsorbed onto the plates and similarly treated. When multiple samples were being compared, samples were also standardized to all give the same titer signal.

Selection of gp120-Binding Phage 0.5 μg of soluble ADA gp120 was coated onto the surface of a MaxiSorp (Nunc) microtiter plate well in 100 μL PBS for 12 hours at 37° C. After blocking for 2 hours with 2% milk (Biorad) in PBS and washing 3× with 200 μL PBST, the concentrated phage library was added in 100 μL 2% milk PBST and incubated at 37° C. for 4 hours. Washing was done with PBST and PBS after which phage were eluted with 1.75 trypsin (Worthington Biochemicals) for 12 minutes. Eluted phage were used to infect 20 mL of a 0.4 O.D. culture of SY-X-E. coli in 2YT supplemented with 30 μg/mL chloramphenicol and 30 μg/mL tetracycline. Infection was allowed to occur for 1 hour at 37° C. after which a small aliquot of cells were plated to determine the number of eluted phage. The rest of the cells were spun down and resuspended in 25 mL 2YT supplemented with 30 μg/mL chloramphenicol, 30 μg/mL tetracycline, 100 μg/mL ampicillin, and 1% glucose. After overnight growth, the enriched library was used to produce phage for the subsequent round.

Determination of gp120-Binding Affinity by ELISA

Per sample, 0.33 μg as of soluble ADA gp120 was coated onto the surface of a MaxiSorp (Nunc) microtiter plate well in 100 μL PBS for 12 hours at 37° C. After blocking for 2 hours with 200 μL 2% milk (Bio-Rad) in PBS, Fab proteins, previously purified and quantified according to the procedures described above, were loaded in 100 μL 2% milk PBST and incubated at 37° C. for 2 hours. After washing 5× with PBST, an anti-human kappa light chain antibody (Sigma) was added in 110 μL of 2% milk in PBST and incubated at 37° C. for 2 hours. After washing 8× with PBST, QuantaBlu fluorogenic substrate (Pierce) was added and the ELISA signal was determined using a fluorescence plate reader (SpectraMax Gemini).

Gp120-Binding Selection Using a Doped Library

The general gp120-binding selection procedure was used (see above). Specifically for this selection, the following washing protocols were used.

Round 1: Washed 10× w/200 μL PBST per wash; ~1 minute per wash

Round 2: Washed 12× w/200 μL PBST per wash; ~1 minute per wash

Round 3: Washed 14× w/200 μL PBST per wash; ~1 minute per wash

Round 4: Washed 15× w/200 μL PBST per wash; ~1 minute per wash

For this selection, the amounts of loaded and eluted phage throughout the rounds are listed below. Also listed is the amount of phage present in the final wash before elution, if measured.

| Round | Amount Phage Loaded | Amount Phage Eluted | Amount Phage in final wash | Loaded/Eluted |
|---|---|---|---|---|
| 1 | $1.23 \times 10^9$ | 4000 | <40 | $3.08 \times 10^5$ |
| 2 | $4.5 \times 10^8$ | $1.08 \times 10^4$ | 40 | $4.17 \times 10^4$ |
| 3 | $6.3 \times 10^6$ | $1.7 \times 10^4$ | 220 | 370 |
| 4 | $3 \times 10^7$ | 7600 | ND | 3747 |

For this selection, the percent of phage containing at least 1 TAG and the percent of phage containing the 412d2TAG doped clone are listed below.

| Round | % phage containing at least one TAG | % phage containing the 412d2TAG doped clone |
|---|---|---|
| 1 | 17 (n = 40) | 2.2 (n = 45) |
| 2 | 14.5 (n = 55) | 10.9 (n = 55) |
| 3 | 86 (n = 50) | 74 (n = 50) |
| 4 | 100 (n = 20) | 100 (n = 20) |

Gp120-Binding Selection Using a Naïve Germline Library

The general gp120-binding selection procedure was used (see above). Specifically for this selection, the following washing protocols were used.

Round 1: Washed 2× w/200 μL PBST per wash; ~1 minute per wash

Round 2: Washed 10× w/200 μL PBST per wash and 1× w/200 μL PBS; ~1 minute per wash.

Round 3: Washed 10× w/200 μL PBST per wash and 1× w/200 μL PBS; ~1 minute per wash.

Round 4: Washed 10× w/200 μL PBST per wash and 1× w/200 μL PBS; ~1 minute per wash For this selection, the amounts of loaded and eluted phage throughout the rounds are listed below. Note that the stringency of round 1 was low and thus the amount of eluted phage was high. This ensures that no arbitrary loss of functional clones occurs when very few copies of each clone were present in the library.

| Round | Amount Phage Loaded | Amount Phage Eluted | Loaded/Eluted |
|---|---|---|---|
| 1 | $1.28 \times 10^9$ | $2.0 \times 10^5$ | 6400 |
| 2 | $2.72 \times 10^8$ | 9200 | $2.86 \times 10^4$ |
| 3 | $1 \times 10^9$ | $2.4 \times 10^5$ | 4166 |
| 4 | $2.5 \times 10^7$ | $3.5 \times 10^4$ | 714 |

Expression of Free scFv Proteins

To express scFvs as free proteins without fusion to phage, the coding regions for scFvs 66CC8, 412d-2SY, and 412d-Y were inserted into the pBAD expression vector containing a gin periplasmic signal sequence and a C-terminal 6×-histidine tag using standard methods. This yielded pBAD-66CC8, pBAD-412d-2SY, and pBAD-412d-Y.

To express 412d-Y as an scFv, Top10 F' cells containing pBAD-412d-Y were grown at 37° C. at 250 rpm in 2YT supplemented with 100 µg/mL ampicillin until the optical density reached 0.6, at which point scFv production was induced with 0.1% L-arabinose. The culture was then allowed to shake at 250 rpm at room temperature for 30 hours, after which cells were pelleted and lysed in 8M urea since no soluble scFv was produced. Refolding using the Protein Refolding Kit (Novagen) yielded soluble scFv.

To express 412d-2SY as an scFv, Top10 F' cells containing pBAD-412d-SY along with pSUPAR6-L3-3SY, an optimized plasmid adapted for expression with unnatural amino acids that, in this case, contains the sulfotyrosine-specific synthetase and the corresponding orthogonal tRNA (Cellitti, S., Jones, D., Lagpacan, L., Hao, X., Zhang, Q., Hu, H., Brittain, S., Brinker, A., Caldwell, J., Bursulaya, B., Spraggon, G., Brock, A., Ryu, Y., Uno, T., Schultz, P., Geierstanger, B. J. *Am. Chem. Soc.* (2008) 130, 9268-9281), were grown at 37° C. at 250 rpm in 2YT supplemented with 100 µg/mL ampicillin, 30 µg/mL chloramphenicol, and 10 mM sulfotyrosine (Bachem). When the optical density reached 0.6, both synthetase and scFv production were induced with 0.2% L-arabinose. The culture was then allowed to shake at 250 rpm at room temperature for 30 hours, after which cells were pelleted and lysed in 8M urea. Refolding using the Protein Refolding Kit (Novagen) yielded soluble scFv.

To express 66CC8-SY as an scFv, Top10 F' cells containing pBAD-66CC8 along with pSUPAR6-L3-3SY were grown at 37° C. at 250 rpm in 2YT supplemented with 100 µg/mL ampicillin, 30 µg/mL chloramphenicol, and 10 mM sulfotyrosine (Bachem). When the optical density reached 0.6, both synthetase and scFv production were induced with 0.2% L-arabinose. The culture was then allowed to shake at 250 rpm at room temperature for 30 hours, after which cells were pelleted and lysed in 8M urea. Refolding was unsuccessful as no soluble protein was recovered.

To express 66CC8-Y as an scFv, Top10 F' cells containing pBAD-66CC8 along with pCDF-JYRS, a plasmid that encodes tyrosine in response to TAG, were grown at 37° C. at 250 rpm in 2YT supplemented with 100 µg/mL ampicillin, 30 µg/mL chloramphenicol. When the optical density reached 0.6, both synthetase and scFv production were induced with 0.2% L-arabinose. The culture was then allowed to shake at 250 rpm at room temperature for 30 hours, after which cells were pelleted and lysed in 8M urea. Refolding was unsuccessful as no soluble protein was recovered.

Protein yield was determined by Western Blot analysis using an anti-6×His antibody (Sigma) and a standard 6×-histidine tagged protein of known concentration.

Expression and Purification of Free Fab Proteins

To convert phage-displayed scFvs into Fab format, the light chain and heavy chain variable regions for scFvs 66CC14, 66CC8, 412d-2SY, and 412d-Y were separately inserted into the pBC expression vector containing human heavy and light chain constant regions (synthesized by Blue Heron) using standard methods. This yielded pBC-66CC14Fab, pBC-66CC8Fab, pBC-412d-2SYFab, and pBC-412d-YFab for Fab expression from a bicistronic construct under the lac promoter.

To express 66CC14 and 412d-Y as Fabs, Top10 F' cells containing either pBC-66CC14Fab or pBC-412d-YFab were grown at 37° C. at 250 rpm in 2YT supplemented with 100 µg/mL ampicillin until the optical density reached 0.6, at which point Fab production was induced with 1 mM IPTG. The culture was then allowed to shake at 250 rpm at room temperature for 30 hours, after which cells were pelleted and lysed three times with 1/20 culture volume of periplasmic lysis buffer (20% sucrose, 30 mM Tris-HCl, 1 mM EDTA, 1 mg/mL lysozyme, pH 7.4). The periplasmic lysate was collected for purification on protein G resin.

To express 412d-2SY and 66CC8-SY as Fabs, Top10 F' cells containing pBC-412d-SYFab or pBC-66CC8-SYFab along with pSUPAR6-L3-3SY were grown at 37° C. at 250 rpm in 2YT supplemented with 100 µg/mL ampicillin, 30 µg/mL chloramphenicol, and 10 mM sulfotyrosine (Bachem). When the optical density reached 0.3, synthetase production was induced with 0.2% L-arabinose. When the optical density reached 0.6, Fab production was induced with 1 mM IPTG. The culture was then allowed to shake at 250 rpm at room temperature for 30 hours, after which cells were pelleted and lysed three times with 1/20 culture volume of periplasmic lysis buffer. The periplasmic lysate was collected for purification on protein G resin.

To express 66CC8-Y as an Fab, Top10 F' cells containing pBC-66CC8Fab along with pCDF-JYRS were grown at 37° C. at 250 rpm in 2YT supplemented with 100 µg/mL ampicillin and 30 µg/mL chloramphenicol. When the optical density reached 0.3, synthetase production was induced with 0.2% L-arabinose. When the optical density reached 0.6, Fab production was induced with 1 mM IPTG. The culture was then allowed to shake at 250 rpm at room temperature for 30 hours, after which cells were pelleted and lysed three times with 1/20 culture volume of periplasmic lysis buffer. The periplasmic lysate was collected for purification on protein G resin.

To purify periplasmic lysates using protein G, 1 mL of protein G resin (Pierce) was packed into a 1 mL polypropylene column (Qiagen). After equilibration of the column with 5 mL binding buffer (50 mM MES, 100 mM NaCl, pH 5.5), periplasmic lysate was loaded onto the column and allowed to pass through the resin by gravity flow. The column was then washed with 15 mL binding buffer and then eluted with 5 mL elution buffer (100 mM glycine, pH 2.8), which was immediately neutralized to pH 7.4. The eluted Fab was then dialyzed into PBS and concentrated for further use.

Fab yield was determined by UV absorbance at $\lambda = 280$.

REFERENCES

1. Vetsigian K, Woese C, & Goldenfeld N (2006) Collective evolution and the genetic code. *Proc Natl Acad Sci USA* 103(28):10696-10701.

2. Wang L, Xie J, & Schultz P G (2006) Expanding the genetic code. *Annual review of biophysics and biomolecular structure* 35:225-249.
3. Xie J, Liu W, & Schultz P G (2007) A genetically encoded bidentate, metal-binding amino acid. *Angewandte Chemie (International ed.)* 46(48):9239-9242.
4. Brustad E, et al. (2008) A genetically encoded boronic acid. *Angewandte Chemie(International ed.)* In Press.
5. Liu C C & Schultz P G (2006) Recombinant expression of selectively sulfated proteins in Escherichia coli. *Nature biotechnology* 24(11):1436-1440.
6. Liu C C, Brustad E, Liu W, & Schultz P G (2007) Crystal structure of a biosynthetic sulfohirudin complexed to thrombin. *Journal of the American Chemical Society* 129 (35):10648-10649.
7. Wang L, Zhang Z, Brock A, & Schultz P G (2003) Addition of the keto functional group to the genetic code of *Escherichia coli*. *Proc Natl Acad Sci USA* 100(1):56-61.
8. Xia G, et al. (2002) Directed evolution of novel polymerase activities: mutation of a DNA polymerase into an efficient RNA polymerase. *Proc Natl Acad Sci USA* 99(10):6597-6602.
9. Rebar E J & Pabo C O (1994) Zinc finger phage: affinity selection of fingers with new DNA-binding specificities. *Science* 263(5147):671-673.
10. Rader C & Barbas C F, 3rd (1997) Phage display of combinatorial antibody libraries. *Current opinion in biotechnology* 8(4):503-508.
11. Martin A, Sieber V, & Schmid F X (2001) In-vitro selection of highly stabilized protein variants with optimized surface. *Journal of molecular biology* 309(3):717-726.
12. Famm K & Winter G (2006) Engineering aggregation-resistant proteins by directed evolution. *Protein Eng Des Sel* 19(10):479-481.
13. Brakmann S & Johnsson K (2002) *Directed Molecular Evolution of Proteins* (Wiley-VCH, Weinheim).
14. Tian F, Tsao M L, & Schultz P G (2004) A phage display system with unnatural amino acids. *Journal of the American Chemical Society* 126(49):15962-15963.
15. Rondot S, Koch J, Breitling F, & Dubel S (2001) A helper phage to improve single-chain antibody presentation in phage display. *Nature biotechnology* 19(1):75-78.
16. Broders O, Breitling F, & Dubel S (2003) Hyperphage. Improving antibody presentation in phage display. *Methods in molecular biology* 205:295-302.
17. Farzan M, et al. (1999) Tyrosine sulfation of the amino terminus of CCR5 facilitates HIV-1 entry. *Cell* 96(5):667-676.
18. Choe H, et al. (2003) Tyrosine sulfation of human antibodies contributes to recognition of the CCR5 binding region of HIV-1 gp120. *Cell* 114(2):161-170.
19. Huang C C, et al. (2007) Structures of the CCR5 N terminus and of a tyrosine-sulfated antibody with HIV-1 gp120 and CD4. *Science* 317(5846):1930-1934.
20. Huang C C, et al. (2004) Structural basis of tyrosine sulfation and VH-gene usage in antibodies that recognize the HIV type 1 coreceptor-binding site on gp120. *Proc Natl Acad Sci USA* 101(9):2706-2711.
21. Yoo T H, Link A J, & Tirrell D A (2007) Evolution of a fluorinated green fluorescent protein. *Proc Natl Acad Sci USA* 104(35):13887-13890.
22. Love K R, Swoboda J G, Noren C J, & Walker S (2006) Enabling glycosyltransferase evolution: a facile substrate-attachment strategy for phage-display enzyme evolution. *Chembiochem* 7(5):753-756.
23. Nijkamp H J, et al. (1986) The complete nucleotide sequence of the bacteriocinogenic plasmid CloDF13. *Plasmid* 16(2):135-160.
24. Ryu Y & Schultz P G (2006) Efficient incorporation of unnatural amino acids into proteins in Escherichia coli. *Nature methods* 3(4):263-265.

ADDITIONAL INFORMATION ON FIGS. 7-14

FIG. 7. Phagemid-display of unnatural amino acids. (a) Structure of sulfotyrosine. (b) Structure of para-acetylphenylalanine. (c) Structure of bipyridyl-alanine. (d) Structure of 4-borono-phenylalanine. (e) Yield of phage under optimized conditions (see Methods) where +UAA corresponds to phage produced with the corresponding unnatural amino acid (UAA) supplemented in the media at optimized concentrations (see Methods) and −UAA corresponds to phage produced in the absence of the corresponding unnatural amino acid. Titers were determined in triplicate and error bars correspond to +standard deviations. (f) Detection of pIII-scFv fusion from whole phage produced using pSEX-GermTAG in the presence of unnatural amino acids. ~$10^8$ phage particles (corresponding to ~200 µL phage culture precipitated and concentrated to ~10 µL) per sample were run on a denaturing PAGE gel under reducing conditions and subsequently transferred to a membrane for western blotting with an anti-pIII antibody. When the same volume of phage similarly produced and prepared from pSEX-GermTAG in the absence of unnatural amino acid was run and western blotted for pIII, no bands were detected. Hyperphage corresponds to phage without displayed scFv. Control corresponds to phage displaying the pIII-scFv fusion from pSEX-GermTAT with only common amino acids—the 51 kD band is a result of non-specific proteolysis of the 62 kD band (pIII-scFv fusion).

FIG. 8. Percent phage clones containing a TAG codon after phage expression from the pSEX-GermNNK library in Keto-X-*E. coli*, SY-X-*E. coli*, Bpy-X-*E. coli*, or Boro-X-*E. coli* (n=100). Expected value is 17.3%; deviation represents a bias in favor of sequences containing only the 20 canonical amino acids. Phage were produced under optimized conditions.

FIG. 9. Yield of phage per mL culture of 412d-2SY in comparison with phage yield from initial phage library and library at round 3. All phage were produced using SY-X-*E. coli*. For 412d-2SY, titers from three separate phage preparations were averaged and error bar represents+standard deviation.

FIG. 10. Phage ELISA for gp120 binding with 412d-2SY selected from a doped 412d library compared with 412d-Y where sulfotyrosines were replaced by tyrosines. For each sample, 0.33 µg gp120 was coated onto a Maxisorp plate, blocked with 2% milk, and bound with the respective phage. Phage was detected with an anti-M13 antibody. BSA binding was used as a control to show specific gp120 binding. Mock refers to signal generated without any phage added.

FIG. 11. (a) Enrichment for gp120 binding as judged by the eluted phage amount after each round. Round 1 selection was done with much lower stringency than with subsequent rounds (see Methods) in order to minimize arbitrary loss of potential hits when few copies of each clone were present. (b) Increase in the percent clones containing sulfotyrosine after each round as determined by sequencing (n=15-30).

FIG. 12. Yield of phage per mL culture of 66CC8-SY in comparison with phage yield from initial phage library and library at round 3. All phage were produced in SY-X-*E. coli*. All phage were produced in SY-X-*E. coli*. For 66CC8-SY, titers from three separate phage preparations were averaged and error bar represents+standard deviation. For 66CC8-SY, when unnatural amino acid was omitted from the media, phage yield was ~5×106.

FIG. 13. Phage ELISA for gp120 binding with 66CC8-SY, 66CC8-Y, and 66CC14. For each sample, 0.3 μg gp120 was coated onto a microtiter plate well, blocked with 2% milk, and bound with the respective phage. Phage was detected with an anti-M13 antibody. BSA binding was used as a control to show specific gp120 binding. (a) ELISA for a representative gp120-binding experiment done with two phage concentrations. (b) Average ELISA signals representing 4 separate experiments done with two separate phage preparations. Each experiment utilized the same amount of phage across all samples. Averages were calculated from signals normalized to 412d-2SY's binding within the same experiment. Error bars represent+standard deviations. We note that this consolidated graph exaggerates variation because the separate ELISA experiments use different phage concentrations, and represent different incubation, washing, development, and detection times.

FIG. 14a depicts the Western Blot analysis of protein G purified Fabs using antihuman kappa light chain HRP antibody developed with metal-enhanced DAB kit (Pierce). Samples were run on a denaturing PAGE gel (Invitrogen NuPAGE 4-12% Bis-Tris). For 66CC8-SY and 412d-SY, lanes corresponding to expression in the absence of sulfotyrosine are also presented to show dependence of sulfated antibody expression on the presence of sulfotyrosine. FIG. 14b-f depict LCMS (ESI-positive) spectra of Fabs 66CC14, 66CC8-SY, 66CC8-Y, 412d-SY, and 412d-Y, respectively. FIG. 14g shows results of ELISAs measuring binding of gp120 by purified Fabs 412d-2SY, 412d-Y, 66CC8-SY, 66CC8, and 66CC14.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A nucleic acid expression library, comprising: a plurality of recombinant nucleic acid expression constructs, wherein a nucleic acid encoding a polypeptide product of at least one of the expression constructs comprises at least one selector codon such that at least one unnatural amino acid is incorporated into at least one of the polypeptide products; wherein the expression constructs are expressed such that polypeptide products comprising the at least one unnatural amino acid are present in the library at a ratio of 10:1 relative to polypeptide products comprising only natural amino acids; wherein the expression constructs encode polypeptide products that comprise:
   a) at least one antibody fragment variant comprising the at least one unnatural amino acid and exhibiting altered binding affinity for a ligand relative to a corresponding antibody fragment comprising only natural amino acids, and
   b) a packaging or specificity polypeptide comprising at least one same unnatural amino acid as the at least one antibody fragment variant, which packaging or specificity polypeptide is essential for viability of an expression vector.

2. The nucleic acid expression library of claim 1, wherein the selector codon comprises a stop codon, a four-base codon, a rare codon, or a non-coding codon.

3. The nucleic acid expression library of claim 1, wherein the at least one unnatural amino acid incorporated into at least one of the polypeptide products expressed by the recombinant nucleic acid expression constructs comprises O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; sulfotyrosine, 4-borono-phenylalanine, or a cyclic amino acid other than proline.

4. A vector packaging system, comprising:
a vector nucleic acid comprising or encoding a packaging site, which vector nucleic acid encodes a target polypeptide that is encoded by a subsequence of the vector nucleic acid, wherein the nucleic acid encoding the target polypeptide comprises at least one first selector codon, and wherein the target polypeptide encoded by the vector nucleic acid comprises an antibody fragment comprising at least one unnatural amino acid and exhibiting altered binding affinity for a ligand relative to a corresponding antibody fragment comprising only natural amino acids;
a complementation nucleic acid that encodes a packaging or specificity polypeptide, which packaging or specificity polypeptide encoded by the complementation nucleic acid is packaged with the vector nucleic acid or a copy or transcript thereof in the system, wherein the complementation nucleic acid comprises at least one second selector codon, wherein the first and second selector codons are the same; and wherein the packaging or specificity polypeptide is essential for vector viability; and,
an orthogonal tRNA that is charged with the at least one unnatural amino acid, which orthogonal tRNA recognizes the at least one first and at least one second codons, thereby permitting translation of the packaging or specificity polypeptide and the target polypeptide by the vector packaging system.

5. The vector packaging system of claim 4, wherein the target polypeptide encoded by a subsequence of the vector nucleic acid is a fusion protein.

6. The vector packaging system of claim 5, wherein the fusion protein comprises a ribosomally synthesized antibody fragment or derivative thereof.

7. The vector packaging system of claim 6, wherein the antibody fragment comprises a complementarity determining region (CDR).

8. The vector packaging system of claim 4, wherein the selector codon encoded by the vector nucleic acid or by the complementation nucleic acid is a stop codon, a 4-base codon, a rare codon, or a noncoding codon.

9. The vector packaging system of claim 4, wherein the packaging or specificity polypeptide encoded by the complementation nucleic acid comprises a viral capsid or envelope protein.

10. The vector packaging system of claim 9, wherein the capsid protein is a pIII.

11. The vector packaging system of claim 4, wherein the system comprises an in vitro translation system.

12. The vector packaging system of claim 4, wherein the system comprises a cell.

13. The vector packaging system of claim 12, wherein the cell comprises a mammalian cell, an insect cell, a bacterial cell, or an E. coli cell.

14. The vector packaging system of claim 4, wherein the system comprises an orthogonal aminoacyl-tRNA synthetase capable of charging the orthogonal tRNA with the at least one unnatural amino acid.

15. The vector packaging system of claim 14, wherein the system comprises the at least one unnatural amino acid.

16. The vector packaging system of claim 15, wherein the at least one unnatural amino acid comprises a bipyridyl alanine residue.

17. An E. coli cell comprising:
a phagemid comprising an M13 packaging sequence, which phagemid encodes a fusion protein comprising an antibody fragment, wherein the phagemid nucleic acid encoding the antibody fragment comprises at least one first selector codon;
a plasmid encoding a mutant pIII polypeptide, which mutant pIII polypeptide is packaged with a copy of the phagemid, wherein plasmid nucleic acid encoding the mutant pIII polypeptide comprises at least one second selector codon, wherein the at least one first selector codon and the at least one second selector codons are the same; and wherein the mutant pIII polypeptide is essential for phagemid viability; and,
an orthogonal tRNA that is charged with an unnatural amino acid, which orthogonal tRNA recognizes the at least one first selector codon and the at least one second selector codon, thereby permitting translation of the pIII polypeptide and of the antibody fragment fusion protein by a vector packaging system; which expressed antibody fragment fusion protein comprises the unnatural amino acid and exhibits altered binding affinity for a ligand relative to a corresponding antibody fragment fusion protein comprising only natural amino acids.

18. A vector comprising:
a packaged nucleic acid encoding a target polypeptide, wherein a subsequence of the packaged nucleic acid encoding the target polypeptide comprises at least one selector codon;
the target polypeptide encoded by the packaged nucleic acid, wherein the target polypeptide comprises an antibody fragment, which antibody fragment comprises at least one first unnatural amino acid and exhibits altered binding affinity for a ligand relative to a corresponding antibody fragment comprising only natural amino acids; and,
a specificity polypeptide that confers host cell specificity to the vector, which specificity polypeptide is essential for vector viability, wherein the specificity polypeptide comprises at least one second unnatural amino acid, and wherein the first unnatural amino acid and the second unnatural amino acid are the same.

19. The vector of claim 18, wherein the packaged nucleic acid comprises or encodes a packaging site.

20. The vector of claim 18, wherein the target polypeptide encoded by the packaged nucleic acid is a fusion protein.

21. The vector of claim 18, wherein the encoded target polypeptide is a fusion protein comprising an antibody fragment.

22. The vector of claim 21, wherein the antibody fragment comprises a complementarity determining region (CDR).

23. The vector of claim 18, wherein the specificity polypeptide comprises a capsid protein.

24. The vector of claim 23, wherein the capsid protein comprises a pIII protein.

25. The vector of claim 18, wherein the specificity polypeptide comprises an envelope protein.

26. The vector of claim 18, wherein the vector comprises a viral capsid.

27. The vector of claim 26, wherein the vector is derived from: a mammalian virus, an adenovirus, an adeno-associated virus, a retrovirus, a herpes virus, an insect virus, a baculovirus, or a bacteriophage.

28. The vector claim 27, wherein the bacteriophage is derived from M13.

29. The vector of claim 18, wherein the target polypeptide is displayed on an outer surface of the vector.

* * * * *

UNITED STATES PATENT AND TRADEMARK OFFICE
CERTIFICATE OF CORRECTION

PATENT NO. : 9,249,408 B2
APPLICATION NO. : 12/734416
DATED : February 2, 2016
INVENTOR(S) : Liu et al.

Page 1 of 1

It is certified that error appears in the above-identified patent and that said Letters Patent is hereby corrected as shown below:

In the Specification

Column 1, Lines 20-28, the paragraph STATEMENT AS TO RIGHTS TO INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant numbers GM062159 and GM056528 awarded by the National Institutes of Health. The government has certain rights in the invention. --

Signed and Sealed this
Seventh Day of April, 2020

Andrei Iancu
*Director of the United States Patent and Trademark Office*

SEQUENCE LISTING

```
<160> NUMBER OF SEQ ID NOS: 97

<210> SEQ ID NO 1
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 1
gcgaaagann ggtagarykg garckacnac tacttt                              36

<210> SEQ ID NO 2
<211> LENGTH: 42
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 2
```
gcgaaagann nknggtagar ykggarckac nnknactact tt                42

<210> SEQ ID NO 3
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 3
gcgaaagann ggtayarykg garctagnac tacttt                       36

<210> SEQ ID NO 4
<211> LENGTH: 42
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 4
gcgaaagann nknggtayar ykggarctag nnknactact tt                42

<210> SEQ ID NO 5
<211> LENGTH: 48
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 5
gcgaaagant agtaykatdd ywbkrskrgt tattaywmcn actacttt          48

<210> SEQ ID NO 6
<211> LENGTH: 54
<212> TYPE: DNA
<213> ORGANISM: Artificial Sequence
<220> FEATURE:

```
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 6
gcgaaagann nktagtayka tddywbkrsk rgttattayw mcnnknacta cttt            54

<210> SEQ ID NO 7
<211> LENGTH: 48
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 7
gcgaaagant attagkatdd ywbkrskrgt tattaywmcn actacttt                   48

<210> SEQ ID NO 8
<211> LENGTH: 54
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 8
gcgaaagann nktattagka tddywbkrsk rgttattayw mcnnknacta cttt            54

<210> SEQ ID NO 9
<211> LENGTH: 48
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
```

<222> LOCATION: (40)..(40)
<223> OTHER INFORMATION: n is a, c, g, or t

<400> SEQUENCE: 9
gcgaaagant attaykatdd ywbkrskrgt tagtaywmcn actacttt                48

<210> SEQ ID NO 10
<211> LENGTH: 54
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 10
gcgaaagann nktattayka tddywbkrsk rgttagtayw mcnnknacta cttt          54

<210> SEQ ID NO 11
<211> LENGTH: 48
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 11
gcgaaagant attaykatdd ywbkrskrgt tattagwmcn actacttt                48

<210> SEQ ID NO 12
<211> LENGTH: 54
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 12
gcgaaagann nktattayka tddywbkrsk rgttattagw mcnnknacta cttt          54

```
<210> SEQ ID NO 13
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 13
gcgaaagang actagrgtra ctmcnactac ttt                              33

<210> SEQ ID NO 14
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 14
gcgaaagann nkgactagrg tractmcnnk nactactttt                       39

<210> SEQ ID NO 15
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 15
gcgaaagang actacrgtra ctagnactac ttt                              33

<210> SEQ ID NO 16
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
```

```
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 16
gcgaaagann nkgactacrg tractagnnk nactactتt                    39

<210> SEQ ID NO 17
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 17
gcgaaagann gtrgatagrg ykryrrttac nactactتt                    39

<210> SEQ ID NO 18
<211> LENGTH: 45
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 18
gcgaaagann nkngtrgata grgykryrrt tacnnknact acttt             45

<210> SEQ ID NO 19
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
```

<400> SEQUENCE: 19
gcgaaagann gtrgakayrg ytagrrttac nactactttt          39

<210> SEQ ID NO 20
<211> LENGTH: 45
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 20
gcgaaagann nkngtrgaka yrgytagrrt tacnnknact actttt          45

<210> SEQ ID NO 21
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 21
gcgaaagann gtrgakayrg ykryrrttag nactactttt          39

<210> SEQ ID NO 22
<211> LENGTH: 45
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

```
<400> SEQUENCE: 22
gcgaaagann nkngtrgaka yrgykryrrt tagnnknact acttt                45

<210> SEQ ID NO 23
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 23
gcgaaagang rgtagagcag cagctsgtmc nactacttt                      39

<210> SEQ ID NO 24
<211> LENGTH: 45
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 24
gcgaaagann nkgrgtagag cagcagctsg tmcnnknact acttt               45

<210> SEQ ID NO 25
<211> LENGTH: 39
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 25
gcgaaagang rgtatagcag cagctsgtag nactacttt                      39

<210> SEQ ID NO 26
<211> LENGTH: 45
<212> TYPE: DNA
<213> ORGANISM: Artificial Sequence
<220> FEATURE:
<223> OTHER INFORMATION: Chemically synthesized degenerate
      oligonucleotide primer for PCR
```

```
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 26
gcgaaagann nkgrgtatag cagcagctsg tagnnknact acttt          45

<210> SEQ ID NO 27
<211> LENGTH: 27
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 27
gcgaaagant agnnknnkna ctacttt                              27

<210> SEQ ID NO 28
<211> LENGTH: 27
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 28
gcgaaagann nktagnnkna ctacttt                              27

<210> SEQ ID NO 29
<211> LENGTH: 27
<212> TYPE: DNA
<213> ORGANISM: Artificial Sequence
<220> FEATURE:
<223> OTHER INFORMATION: Chemically synthesized degenerate
      oligonucleotide primer for PCR
```

```
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 29
gcgaaagann nknnktagna ctacttt                                              27

<210> SEQ ID NO 30
<211> LENGTH: 30
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 30
gcgaaagant agnnknnknn knactacttt                                           30

<210> SEQ ID NO 31
<211> LENGTH: 30
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 31
gcgaaagann nktagnnknn knactacttt                                           30
```

```
<210> SEQ ID NO 32
<211> LENGTH: 30
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 32
gcgaaagann nknnktagnn knactacttt                                       30

<210> SEQ ID NO 33
<211> LENGTH: 30
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 33
gcgaaagann nknnknnkta gnactacttt                                       30

<210> SEQ ID NO 34
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
```

```
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 34
gcgaaagant agnnknnknn knnknactac ttt                              33

<210> SEQ ID NO 35
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 35
gcgaaagann nktagnnknn knnknactac ttt                              33

<210> SEQ ID NO 36
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 36
```
gcgaaagann nknnktagnn knnknactac ttt         33

<210> SEQ ID NO 37
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 37
gcgaaagann nknnknnkta gnnknactac ttt         33

<210> SEQ ID NO 38
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 38
gcgaaagann nknnknnknn ktagnactac ttt         33

<210> SEQ ID NO 39
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature

```
<222> LOCATION: (9)..(9)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 39
gcgaaagant agnnknnknn knnknnknac tacttt                             36

<210> SEQ ID NO 40
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 40
gcgaaagann nktagnnknn knnknnknac tacttt                             36

<210> SEQ ID NO 41
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
```

<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 41
gcgaaagann nknnktagnn knnknnknac tactttt                36

<210> SEQ ID NO 42
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 42
gcgaaagann nknnknnkta gnnknnknac tactttt                36

<210> SEQ ID NO 43
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

```
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 43
gcgaaagann nknnknnknn ktagnnknac tacttt                              36

<210> SEQ ID NO 44
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 44
gcgaaagann nknnknnknn knnktagnac tacttt                              36

<210> SEQ ID NO 45
<211> LENGTH: 27
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
```

```
<221> NAME/KEY: misc_feature
<222> LOCATION: (19)..(19)
<223> OTHER INFORMATION: n is a, c, g, or t

<400> SEQUENCE: 45
gcgaaagann nknnknnkna ctacttt                                          27

<210> SEQ ID NO 46
<211> LENGTH: 30
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 46
gcgaaagann nknnknnknn knactacttt                                       30

<210> SEQ ID NO 47
<211> LENGTH: 33
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 47
gcgaaagann nknnknnknn knnknactac ttt                                   33
```

```
<210> SEQ ID NO 48
<211> LENGTH: 36
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 48
gcgaaagann nknnknnknn knnknnknac tactttt                               36

<210> SEQ ID NO 49
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.

<400> SEQUENCE: 49

Glu Ser Ser Tyr Met Gly Leu Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (7)..(7)
<223> OTHER INFORMATION: X is sulfotyrosine

<400> SEQUENCE: 50

Glu Val Leu His Arg Glu Xaa Tyr
1               5

<210> SEQ ID NO 51
<211> LENGTH: 8
<212> TYPE: PRT
<213> ORGANISM: Artificial Sequence
```

```
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (5)..(5)
<223> OTHER INFORMATION: X is sulfotyrosine

<400> SEQUENCE: 51

Glu His Arg Asn Xaa Met Trp Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.

<400> SEQUENCE: 52

Glu Ser Val Lys Ser Arg Lys Asp
1               5

<210> SEQ ID NO 53
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (2)..(2)
<223> OTHER INFORMATION: Xaa is sulfotyrosine

<400> SEQUENCE: 53

Asp Xaa Ala Arg Gly Ile Ser Asp
1               5

<210> SEQ ID NO 54
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.

<400> SEQUENCE: 54

Glu Thr Asn His Ala His Asp His
1               5

<210> SEQ ID NO 55
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (3)..(3)
<223> OTHER INFORMATION: Xaa is sulfotyrosine

<400> SEQUENCE: 55
```

Asp His Xaa Arg Ala His Ser Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (3)..(3)
<223> OTHER INFORMATION: Xaa is sulfotyrosine

<400> SEQUENCE: 56

Asp Gln Xaa Trp Cys His Arg Asn
1               5

<210> SEQ ID NO 57
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (7)..(7)
<223> OTHER INFORMATION: Xaa is sulfotyrosine

<400> SEQUENCE: 57

Asp Arg Lys His Gly Gly Xaa Tyr
1               5

<210> SEQ ID NO 58
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (2)..(2)
<223> OTHER INFORMATION: Xaa is sulfotyrosine
<220> FEATURE:
<221> NAME/KEY: misc_feature
<222> LOCATION: (6)..(6)
<223> OTHER INFORMATION: Xaa is sulfotyrosine

<400> SEQUENCE: 58

Glu Xaa Asp Pro Arg Xaa Gly His
1               5

<210> SEQ ID NO 59
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (2)..(2)
<223> OTHER INFORMATION: Xaa is sulfotyrosine
<220> FEATURE:
<221> NAME/KEY: misc_feature

```
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is sulfotyrosine

<400> SEQUENCE: 59

Glu Thr Ser Xaa Ala Xaa Glu Asn
1               5

<210> SEQ ID NO 60
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (6)..(6)
<223> OTHER INFORMATION: Xaa is sulfotyrosine

<400> SEQUENCE: 60

Glu Cys Gly Ser Ser Xaa His Asp
1               5

<210> SEQ ID NO 61
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (6)..(6)
<223> OTHER INFORMATION: Xaa is sulfotyrosine

<400> SEQUENCE: 61

Asp Gly Ser Asp Arg Xaa Val Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
<221> NAME/KEY: misc_feature
<222> LOCATION: (5)..(5)
<223> OTHER INFORMATION: Xaa is sulfotyrosine

<400> SEQUENCE: 62

Asp Asp Gln Val Xaa Ala Ile Asn
1               5

<210> SEQ ID NO 63
<211> LENGTH: 8
<212> TYPE: PRT
<213> ORGANISM: Artificial Sequence
<220> FEATURE:
<223> OTHER INFORMATION: Partial amino acid sequence of heavy chain CDR3
      from mutant Fab isolated from screen to identify Fabs that bind
      nickel resin.
<220> FEATURE:
```

<221> NAME/KEY: misc_feature
<222> LOCATION: (5)..(5)
<223> OTHER INFORMATION: Xaa can be any naturally occurring amino acid

<400> SEQUENCE: 63

Glu Phe Thr Tyr Xaa Val Arg His
1               5

<210> SEQ ID NO 64
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (5)..(5)
<223> OTHER INFORMATION: Xaa is sulfotyrosine
<220> FEATURE:
<221> NAME/KEY: misc_feature
<222> LOCATION: (8)..(8)
<223> OTHER INFORMATION: Xaa is sulfotyrosine

<400> SEQUENCE: 64

Tyr Pro Asn Asp Xaa Asn Asp Xaa Ala Pro Glu Glu Gly Met
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (8)..(8)
<223> OTHER INFORMATION: Xaa is sulfotyrosine

<400> SEQUENCE: 65

Tyr Thr Asn Asp Leu Asn Asp Xaa Gly Glu Glu Glu His Gly
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (13)..(13)
<223> OTHER INFORMATION: Xaa is sulfotyrosine

<400> SEQUENCE: 66

Tyr Asn Asn Asp Asp Asn Asp Leu Arg Leu Gly Glu Xaa Ser
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (13)..(13)
<223> OTHER INFORMATION: Xaa is sulfotyrosine

<400> SEQUENCE: 67

Tyr Asp Asn Asp Asn Asp Asp Gly Thr Ala Glu Glu Xaa Tyr
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (5)..(5)
<223> OTHER INFORMATION: Xaa is sulfotyrosine
<220> FEATURE:
<221> NAME/KEY: misc_feature
<222> LOCATION: (8)..(8)
<223> OTHER INFORMATION: Xaa is sulfotyrosine

<400> SEQUENCE: 68

Tyr Pro Asn Asp Xaa Asn Asp Xaa Ala Pro Glu Glu Gly Ser
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Sequence of amino acids 100 - 114 of the human
      412d scFv derivative 412d-2SY
<220> FEATURE:
<221> NAME/KEY: misc_feature
<222> LOCATION: (5)..(5)
<223> OTHER INFORMATION: Xaa is sulfotyrosine
<220> FEATURE:
<221> NAME/KEY: misc_feature
<222> LOCATION: (8)..(8)
<223> OTHER INFORMATION: Xaa is sulfotyrosine

<400> SEQUENCE: 69

Tyr Pro Asn Asp Xaa Asn Asp Xaa Ala Pro Glu Glu Gly Met
1               5                   10

<210> SEQ ID NO 70
<211> LENGTH: 8
<212> TYPE: PRT
<213> ORGANISM: Artificial Sequence
<220> FEATURE:
<223> OTHER INFORMATION: Amino acid subsequence of an scFv isolated in
      phage display screen
<220> FEATURE:
<221> NAME/KEY: misc_feature
<222> LOCATION: (2)..(2)
<223> OTHER INFORMATION: Xaa is sulfotyrosine

<400> SEQUENCE: 70

Glu Xaa Gly Ser Pro Arg Gly Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: Amino acid subsequence of an scFv isolated in
      phage display screen

<400> SEQUENCE: 71

-continued

Glu Arg Arg Gly Arg Glu Gly His
1               5

<210> SEQ ID NO 72
<211> LENGTH: 42
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 72
gtgttgttgt tgttgtatac caaatagcta gctcactcgg tc                        42

<210> SEQ ID NO 73
<211> LENGTH: 42
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 73
gttgttgagc tcgataaatt gcactgaaat ctagagcggt tc                        42

<210> SEQ ID NO 74
<211> LENGTH: 24
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 74
gcacgcgtag aaattgtgtt gacg                                            24

<210> SEQ ID NO 75
<211> LENGTH: 49
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 75
ctttggatcc agcggccgcc cgtttgattt ccaccttggt cccttggcc                 49

<210> SEQ ID NO 76
<211> LENGTH: 34
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 76
cggccatggc tgaggtgcag ctgttggagt ctgg                                 34

<210> SEQ ID NO 77
<211> LENGTH: 56
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 77
cttcaagctt tggggcggat gcactccctg aggagacggt gaccagggtt ccttgg    56

<210> SEQ ID NO 78
<211> LENGTH: 40
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 78
tctcgaaatc catggctgag gtgcagctgt tggagtctgg    40

<210> SEQ ID NO 79
<211> LENGTH: 22
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 79
tctttcgcac agtaatatac gg    22

<210> SEQ ID NO 80
<211> LENGTH: 61
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (23)..(25)
<223> OTHER INFORMATION: N is A, C, G, or T
<220> FEATURE:
<221> NAME/KEY: misc_feature
<222> LOCATION: (26)..(26)
<223> OTHER INFORMATION: K = G or T
<220> FEATURE:
<221> NAME/KEY: misc_feature
<222> LOCATION: (27)..(28)
<223> OTHER INFORMATION: N is A, C, G, or T
<220> FEATURE:
<221> NAME/KEY: misc_feature
<222> LOCATION: (29)..(29)
<223> OTHER INFORMATION: K is G or T
<220> FEATURE:
<221> NAME/KEY: misc_feature
<222> LOCATION: (30)..(31)
<223> OTHER INFORMATION: N is A, C, G, or T
<220> FEATURE:
<221> NAME/KEY: misc_feature
<222> LOCATION: (32)..(32)
<223> OTHER INFORMATION: K is G or T
<220> FEATURE:
<221> NAME/KEY: misc_feature
<222> LOCATION: (33)..(34)
<223> OTHER INFORMATION: N is A, C, G, or T
<220> FEATURE:
<221> NAME/KEY: misc_feature
<222> LOCATION: (35)..(35)
<223> OTHER INFORMATION: K is G or T
<220> FEATURE:
<221> NAME/KEY: misc_feature
<222> LOCATION: (36)..(37)
<223> OTHER INFORMATION: N is A, C, G, or T
<220> FEATURE:
<221> NAME/KEY: misc_feature
<222> LOCATION: (38)..(38)
<223> OTHER INFORMATION: K is G or T
<220> FEATURE:
<221> NAME/KEY: misc_feature
<222> LOCATION: (39)..(40)

<223> OTHER INFORMATION: N is A, C, G, or T
<220> FEATURE:
<221> NAME/KEY: misc_feature
<222> LOCATION: (41)..(41)
<223> OTHER INFORMATION: K is G or T
<220> FEATURE:
<221> NAME/KEY: misc_feature
<222> LOCATION: (42)..(42)
<223> OTHER INFORMATION: N is A, C, G, or T

<400> SEQUENCE: 80
ccgtatatta ctgtgcgaaa gannnknnkn nknnknnknn knactacttt gactactggg    60
g    61

<210> SEQ ID NO 81
<211> LENGTH: 64
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 81
agccatcgcg gccgcgctag ctgaggagac ggtgaccagg gttccttggc cccagtagtc    60
aaag    64

<210> SEQ ID NO 82
<211> LENGTH: 34
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 82
cggccatggc tgaggtgcag ctgttggagt ctgg    34

<210> SEQ ID NO 83
<211> LENGTH: 56
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 83
cttcaagctt tggggcggat gcactccctg aggagacggt gaccagggtt ccttgg    56

<210> SEQ ID NO 84
<211> LENGTH: 45
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 84
cacgccatgg ctgaggtgca gctggtgcag tctggggctg aggtg    45

<210> SEQ ID NO 85
<211> LENGTH: 52
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 85
cttTggatcc agcggccgcc cgtttgattt ccaccttggt ccCctggcca aa    52

<210> SEQ ID NO 86
<211> LENGTH: 20
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 86
ccgctggctt gctgctgctg    20

<210> SEQ ID NO 87
<211> LENGTH: 28
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 87
gtaagggctc gcacagtaaa atacggcc    28

<210> SEQ ID NO 88
<211> LENGTH: 86
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (28)..(29)
<223> OTHER INFORMATION: N is A, C, G, or T
<220> FEATURE:
<221> NAME/KEY: misc_feature
<222> LOCATION: (30)..(30)
<223> OTHER INFORMATION: K is G or T
<220> FEATURE:
<221> NAME/KEY: misc_feature
<222> LOCATION: (37)..(38)
<223> OTHER INFORMATION: N is A, C, G, or T
<220> FEATURE:
<221> NAME/KEY: misc_feature
<222> LOCATION: (39)..(39)
<223> OTHER INFORMATION: K is G or T
<220> FEATURE:
<221> NAME/KEY: misc_feature
<222> LOCATION: (40)..(41)
<223> OTHER INFORMATION: N is A, C, G, or T
<220> FEATURE:
<221> NAME/KEY: misc_feature
<222> LOCATION: (42)..(42)
<223> OTHER INFORMATION: K is G or T
<220> FEATURE:
<221> NAME/KEY: misc_feature
<222> LOCATION: (46)..(47)
<223> OTHER INFORMATION: N is A, C, G, or T
<220> FEATURE:
<221> NAME/KEY: misc_feature
<222> LOCATION: (48)..(48)
<223> OTHER INFORMATION: K is G or T
<220> FEATURE:
<221> NAME/KEY: misc_feature
<222> LOCATION: (49)..(50)
<223> OTHER INFORMATION: N is A, C, G, or T
<220> FEATURE:
<221> NAME/KEY: misc_feature
<222> LOCATION: (51)..(51)
<223> OTHER INFORMATION: K is G or T
<220> FEATURE:

```
<221> NAME/KEY: misc_feature
<222> LOCATION: (52)..(53)
<223> OTHER INFORMATION: N is A, C, G, or T
<220> FEATURE:
<221> NAME/KEY: misc_feature
<222> LOCATION: (54)..(54)
<223> OTHER INFORMATION: K is G or T
<220> FEATURE:
<221> NAME/KEY: misc_feature
<222> LOCATION: (61)..(62)
<223> OTHER INFORMATION: N is A, C, G, or T
<220> FEATURE:
<221> NAME/KEY: misc_feature
<222> LOCATION: (63)..(63)
<223> OTHER INFORMATION: K is G or T
<220> FEATURE:
<221> NAME/KEY: misc_feature
<222> LOCATION: (64)..(65)
<223> OTHER INFORMATION: N is A, C, G, or T
<220> FEATURE:
<221> NAME/KEY: misc_feature
<222> LOCATION: (66)..(66)
<223> OTHER INFORMATION: K is G or T

<400> SEQUENCE: 88
gccgtatttt actgtgcgag cccttacnnk aatgacnnkn nkgacnnknn knnkgaggag    60
nnknnkagct ggtacttcga tctctg                                        86

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 89
cagagatcga agtaccagct                                               20

<210> SEQ ID NO 90
<211> LENGTH: 20
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 90
agctggtact tcgatctctg                                               20

<210> SEQ ID NO 91
<211> LENGTH: 20
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 91
ctctgatatc tttggatcca                                               20

<210> SEQ ID NO 92
<211> LENGTH: 40
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 92
```

```
tctcgaaatc catggctcag gtgcagctgg tgcagtctgg                            40
```

<210> SEQ ID NO 93
<211> LENGTH: 25
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 93

```
tctctcgcac agtaatacac ggccg                                            25
```

<210> SEQ ID NO 94
<211> LENGTH: 64
<212> TYPE: DNA
<213> ORGANISM: Artificial Sequence
<220> FEATURE:
<223> OTHER INFORMATION: Chemically synthesized degenerate
      oligonucleotide primer for PCR
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(33)
<223> OTHER INFORMATION: k is g or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (44)..(44)
<223> OTHER INFORMATION: k is g or t
<220> FEATURE:
<221> NAME/KEY: misc_feature
<222> LOCATION: (45)..(45)
<223> OTHER INFORMATION: n is a, c, g, or t

<400> SEQUENCE: 94

```
cggccgtgta ttactgtgcg agagannnkn nkknknnknn knnknactac tttgactact      60
gggg                                                                   64

<210> SEQ ID NO 95
<211> LENGTH: 64
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 95
agccatcgcg gccgcgctag ctgaggagac ggtgaccagg gttccttggc cccagtagtc      60
aaag                                                                   64

<210> SEQ ID NO 96
<211> LENGTH: 35
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 96
ccggccatgg ctcaggtgca gctggtgcag tctgg                                 35

<210> SEQ ID NO 97
<211> LENGTH: 53
<212> TYPE: DNA
<213> ORGANISM: Artificial Sequence
<220> FEATURE:
<223> OTHER INFORMATION: Chemically synthesized oligonucleotide primer
      for PCR

<400> SEQUENCE: 97
cttcaagctt tggggcggat gcactccctg aggagacggt gaccagggtt cct             53
```